United States Patent
Koike et al.

(10) Patent No.: US 9,478,750 B2
(45) Date of Patent: Oct. 25, 2016

(54) ANTHRACENE DERIVATIVE AND ORGANIC ELECTROLUMINESCENT ELEMENT USING THE SAME

(71) Applicant: JNC CORPORATION, Tokyo (JP)

(72) Inventors: Toshihiro Koike, Chiba (JP); Yohei Ono, Chiba (JP)

(73) Assignee: JNC CORPORATION, Tokyo (JP)

( * ) Notice: Subject to any disclaimer, the term of this patent is extended or adjusted under 35 U.S.C. 154(b) by 293 days.

(21) Appl. No.: 14/375,243

(22) PCT Filed: Jan. 15, 2013

(86) PCT No.: PCT/JP2013/050550
§ 371 (c)(1),
(2) Date: Jul. 29, 2014

(87) PCT Pub. No.: WO2013/114941
PCT Pub. Date: Aug. 8, 2013

(65) Prior Publication Data
US 2015/0014671 A1 Jan. 15, 2015

(30) Foreign Application Priority Data

Feb. 3, 2012 (JP) .................. 2012-021657
May 9, 2012 (JP) .................. 2012-107229

(51) Int. Cl.
*H01L 51/50* (2006.01)
*H01L 51/00* (2006.01)
(Continued)

(52) U.S. Cl.
CPC ......... *H01L 51/0058* (2013.01); *C07D 213/06* (2013.01); *C07D 213/16* (2013.01);
(Continued)

(58) Field of Classification Search
CPC .. C09K 11/06; C07D 213/06; C07D 213/16; C07D 401/10; H01L 51/0052; H01L 51/0058; H01L 51/0072; H01L 51/0096; H01L 51/5072; H01L 51/5092; Y02E 10/549
See application file for complete search history.

(56) References Cited

U.S. PATENT DOCUMENTS

2007/0106103 A1   5/2007   Ikeda et al.

FOREIGN PATENT DOCUMENTS

| CN | 101364636 | 2/2009 |
|---|---|---|
| CN | 101407493 | 4/2009 |

(Continued)

OTHER PUBLICATIONS

Machine translation for CN 101407493 A (publication date: Apr. 2009).*

(Continued)

*Primary Examiner* — Dawn Garrett
(74) *Attorney, Agent, or Firm* — Wenderoth, Lind & Ponack, L.L.P.

(57) ABSTRACT

This organic electroluminescent element is manufactured by using an anthracene derivative having a pyridyl aryl group substituted with an alkyl represented by formula (1) as an electron transport material, and satisfies characteristics such as the following in an adequate and well-balanced manner: improves the external quantum efficiency of the light-emitting element, which is generally required by the electron transport material; reduces the drive voltage of the light-emitting element; and increases the life of the element. (In formula (1), Ar is a divalent or trivalent benzene or naphthalene; R is hydrogen or an alkyl with a carbon number of 1 to 6, but all of the Rs never simultaneously form hydrogen; and $R^1$ to $R^4$ are, individually, hydrogen, an alkyl with a carbon number of 1 to 6, a cycloalkyl with a carbon number of 3 to 6, or an aryl with a carbon number of 6 to 20.)

16 Claims, 1 Drawing Sheet (1)

(51) Int. Cl.
*C09K 11/06* (2006.01)
*C07D 213/06* (2006.01)
*C07D 401/10* (2006.01)
*C07D 213/16* (2006.01)

(52) U.S. Cl.
CPC ............ *C07D401/10* (2013.01); *C09K 11/06* (2013.01); *H01L 51/0052* (2013.01); *H01L 51/0072* (2013.01); *H01L 51/0096* (2013.01); *H01L 51/5072* (2013.01); *H01L 51/5092* (2013.01); *Y02E 10/549* (2013.01)

(56) References Cited

FOREIGN PATENT DOCUMENTS

| | | |
|---|---|---|
| CN | 101452997 | 6/2009 |
| CN | 101898996 | 12/2010 |
| CN | 102208431 | 10/2011 |
| JP | 2003-146951 | 5/2003 |
| JP | 2003-282270 | 10/2003 |
| JP | 2005-170911 | 6/2005 |
| JP | 2009-173642 | 8/2009 |
| JP | 2010-168363 | 8/2010 |
| WO | 2007/086552 | 8/2007 |
| WO | 2010/137678 | 12/2010 |
| WO | 2012/005214 | 1/2012 |
| WO | 2012/060374 | 5/2012 |

OTHER PUBLICATIONS

Taiwanese Office Action issued Feb. 18, 2016 in corresponding Taiwanese Patent Application No. 102102972.
International Search Report issued Apr. 9, 2013 in International (PCT) Application No. PCT/JP2013/050550.
Chinese Office Action issued Dec. 9, 2015 in corresponding Chinese Patent Application No. 201380004113.2.
Decision to Grant a Patent issued Jun. 23, 2016 in corresponding Taiwanese Patent Application No. 102102972.

* cited by examiner

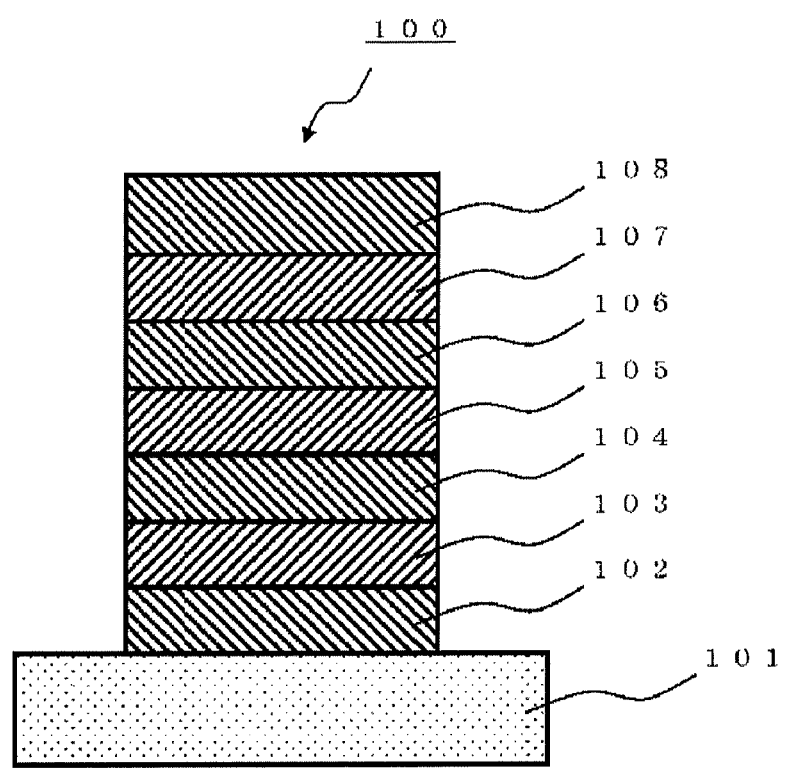

ANTHRACENE DERIVATIVE AND ORGANIC ELECTROLUMINESCENT ELEMENT USING THE SAME

TECHNICAL FIELD

The present invention relates to an anthracene derivative as well as an organic electroluminescent element, a display device and a lighting device using the same.

BACKGROUND ART

Conventionally, since a display device using a luminescent element which is electroluminescent enables power saving and thinning, the device has been variously studied and, further, since an organic electroluminescent element including an organic material facilitates weight saving and increase in size, the device has been actively studied. Particularly, exploitation of an organic material having luminescence property including blue which is one of three primary colors of light, and exploitation of an organic material having the ability to transport a charge such as a hole and an electron (having the probability that the material becomes a semiconductor or a superconductor) have been conventionally studied actively whether it is a high-molecular compound or a low-molecular compound.

For example, a method of synthesizing a compound having a pyridylphenyl structure in a molecule and an organic electroluminescent element using the compound in an organic compound layer have been reported (JP 2003-282270 A (Patent Literature 1)). The Patent Literature 1 reports an organic electroluminescent element using a compound having a pyridylphenyl structure in a molecule, particularly, as an electron transport material. An organic electroluminescent element using a compound substituted with an aryl group and a heteroaryl group such as a pyridyl group and a phenyl group in a central skeleton of anthracene (JP 2005-170911 A (Patent Literature 2), JP 2003-146951 A (Patent Literature 3)), and an example of use of a compound substituted with a pyridyl group via benzene or naphthalene in a central skeleton of anthracene, particularly, as an electron transport material have been also reported (JP 2009-173642A (Patent Literature 4), JP 2010-168363 A (Patent Literature 5)).

CITATION LIST

Patent Literature

Patent Literature 1: JP 2003-282270 A
Patent Literature 2: JP 2005-170911 A
Patent Literature 3: JP 2003-146951 A
Patent Literature 4: JP 2009-173642 A
Patent Literature 5: JP 2010-168363 A

SUMMARY OF INVENTION

Technical Problem

Although some electron transport materials of a compound having a pyridylphenyl structure or a pyridylnaphthyl structure in a molecule, and some materials for a luminescent element of a compound having an anthracene skeleton are known as described above, these known materials do not sufficiently and well-balancedly satisfy properties that an external quantum efficiency of a luminescent element is improved, a driving voltage of a luminescent element is reduced, and a device life is prolonged, which are generally required for an electron transport material (materials for an electron transport layer and an electron injection layer). Under such the circumstances, exploitation of an electron transport material excellent in an external quantum efficiency, a driving voltage and a device life of a luminescent element is desired. Furthermore, in a blue luminescent element, an electron transport material exerting excellent property has not been obtained, and exploitation of an electron transport material suitable for improvement in property of the blue luminescent element is desired.

Solution to Problem

In order to solve the problems, the present inventors intensively studied, and as a result, found out that it is effective that an electron transport material is equipped with an organic layer containing a compound represented by the following general formula (1), in order to obtain an organic electroluminescent element which is excellent in an external quantum efficiency and a device life, and is also excellent in balance with a driving voltage, resulting in completion of the present invention.

[1] An anthracene derivative represented by the following formula (1):

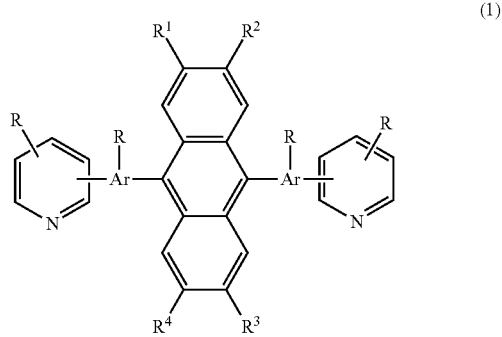

(1)

wherein
Ars are each independently divalent or trivalent benzene or naphthalene,
Rs are each independently hydrogen or an alkyl having a carbon number of 1 to 6, with which Ar or pyridine is substituted, and not all Rs are hydrogen simultaneously, and
$R^1$, $R^2$, $R^3$ and $R^4$ are each independently hydrogen, an alkyl having a carbon number of 1 to 6, a cycloalkyl having a carbon number of 3 to 6 or an aryl having a carbon number of 6 to 20.

[2] The anthracene derivative according to [1], wherein moieties consisting of Ar and pyridine are each independently a group represented by any of the following formula (Py-1) to formula (Py-12):

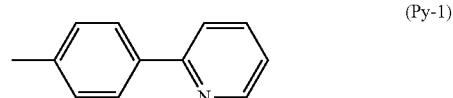

(Py-1)

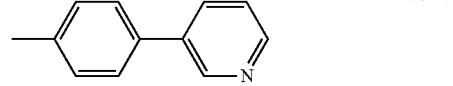

(Py-2)

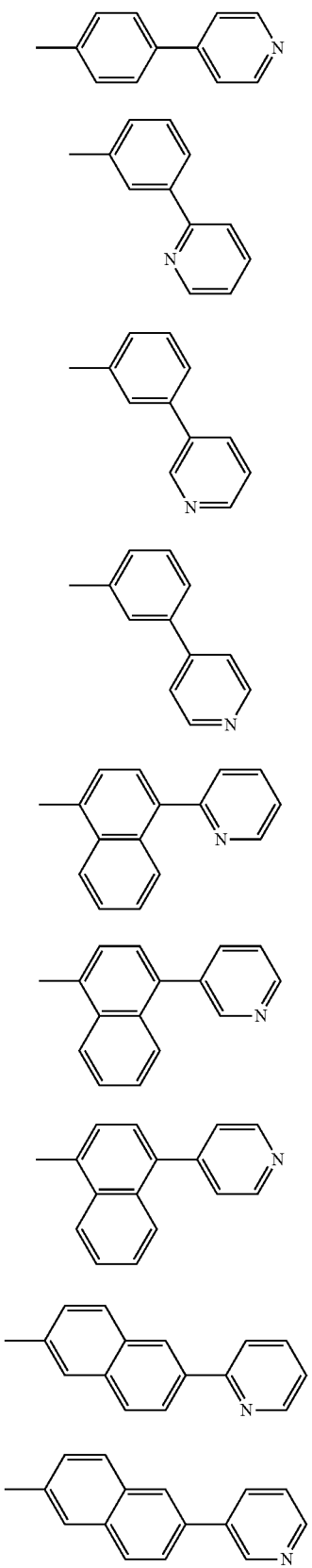

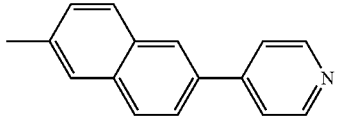

wherein

Rs are each independently hydrogen or an alkyl having a carbon number of 1 to 4, with which a group represented by any of the formula (Py-1) to formula (Py-12) is substituted, and not all Rs are hydrogen simultaneously, and $R^1$ is hydrogen, an alkyl having a carbon number of 1 to 6 or an aryl having a carbon number of 6 to 20, and $R^2$, $R^3$ and $R^4$ are hydrogen.

[3] The anthracene derivative according to [1], wherein moieties consisting of Ar and pyridine are both a group represented by any of the formula (Py-1) to formula (Py-9), two Rs binding to Ar are both hydrogen and two Rs binding to pyridine are both an alkyl having a carbon number of 1 to 4, or two Rs binding to Ar are both an alkyl having a carbon number of 1 to 4 and two Rs binding to pyridine are both hydrogen, and $R^1$ is hydrogen, an alkyl having a carbon number of 1 to 4, phenyl, biphenylyl, terphenylyl or naphthyl, and $R^2$, $R^3$ and $R^4$ are hydrogen.

[4] The anthracene derivative according to [1], wherein moieties consisting of Ar and pyridine are both a group represented by any of the formula (Py-1) to formula (Py-9), two Rs binding to Ar are both hydrogen, and one of two Rs binding to pyridine is an alkyl having a carbon number of 1 to 4 and the other is hydrogen, and $R^1$ is hydrogen, an alkyl having a carbon number of 1 to 4, phenyl, biphenylyl, terphenylyl or naphthyl, and $R^2$, $R^3$ and $R^4$ are hydrogen.

[5] The anthracene derivative according to [1], wherein moieties consisting of Ar and pyridine are both a group represented by any of the formula (Py-1) to formula (Py-6), two Rs binding to Ar are both hydrogen, and two Rs binding to pyridine are both an alkyl having a carbon number of 1 to 4, and $R^1$ is hydrogen, phenyl, terphenylyl or naphthyl, and $R^2$, $R^3$ and $R^4$ are hydrogen.

[6] The anthracene derivative according to [1], wherein moieties consisting of Ar and pyridine are both a group represented by any of the formula (Py-1) to formula (Py-6), two Rs binding to Ar are both an alkyl group having a carbon number of 1 to 4, and two Rs binding to pyridine are both hydrogen, and $R^1$ is hydrogen or phenyl, and $R^2$, $R^3$ and $R^4$ are hydrogen.

[7] The anthracene derivative according to [1], wherein moieties consisting of Ar and pyridine are both a group represented by any of the formula (Py-1) to formula (Py-6), two Rs binding to Ar are both hydrogen, and one of two Rs binding to pyridine is an alkyl having a carbon number of 1 to 4 and the other is hydrogen, and $R^1$ is hydrogen or phenyl, and $R^2$, $R^3$ and $R^4$ are hydrogen.

[8] The anthracene derivative according to [1], which is represented by the following formula (1-34), formula (1-35), formula (1-38), formula (1-39), formula (1-40), formula (1-41), formula (1-50) or formula (1-51):

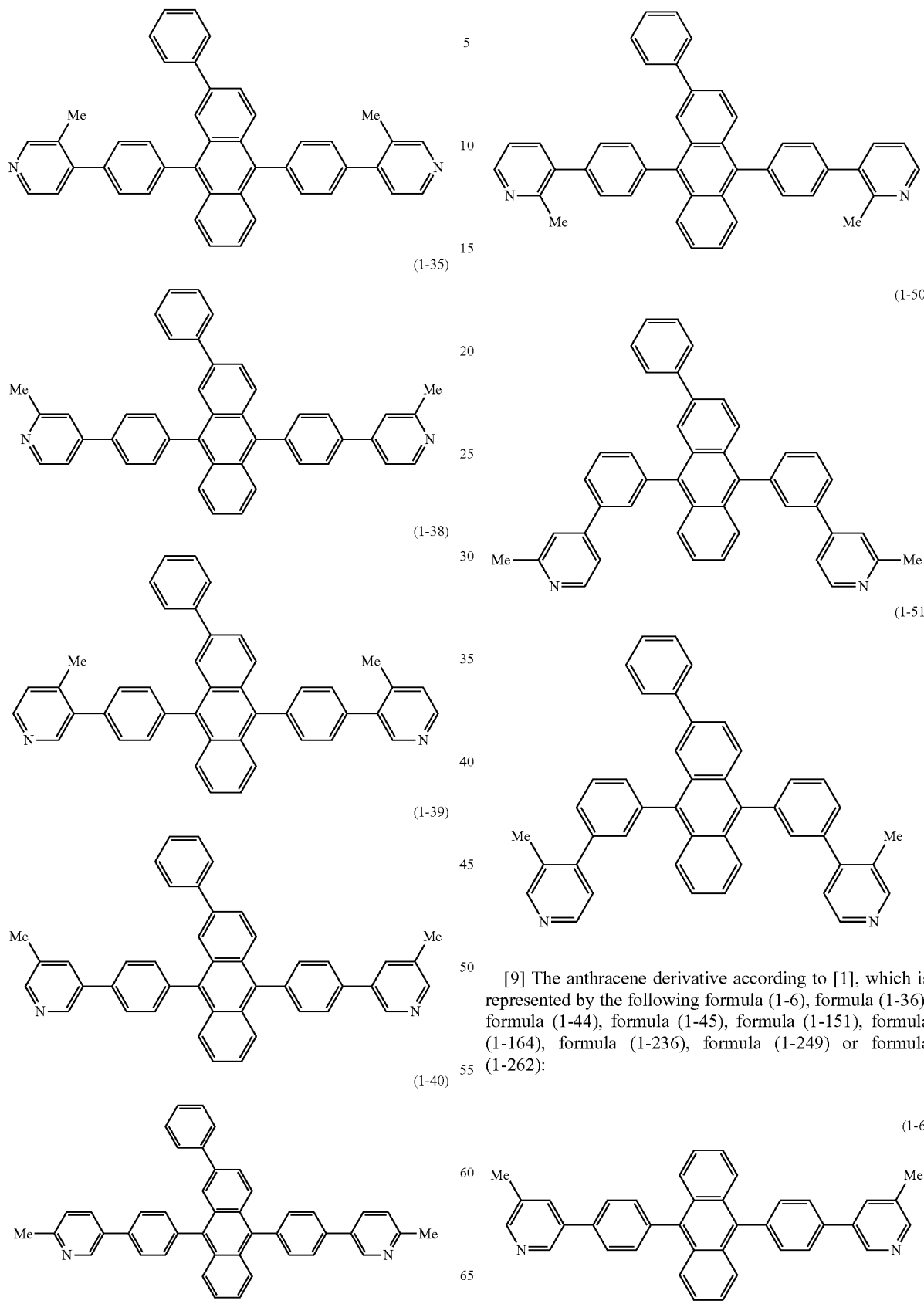
[9] The anthracene derivative according to [1], which is represented by the following formula (1-6), formula (1-36), formula (1-44), formula (1-45), formula (1-151), formula (1-164), formula (1-236), formula (1-249) or formula (1-262):

(1-36)
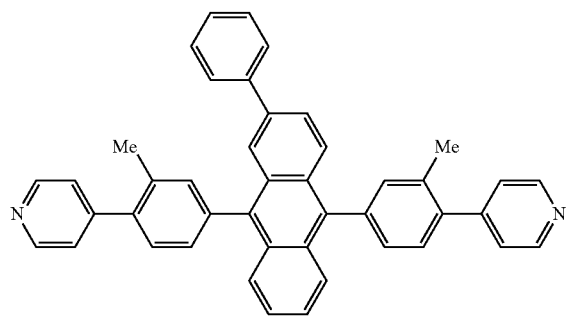
(1-44)
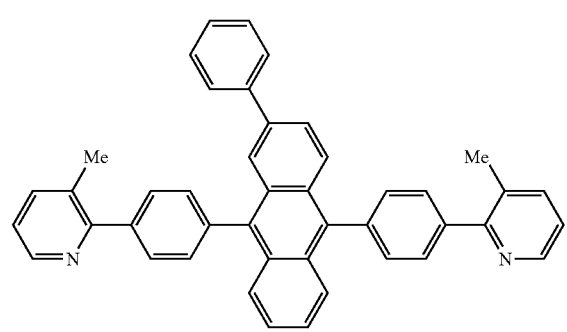
(1-45)
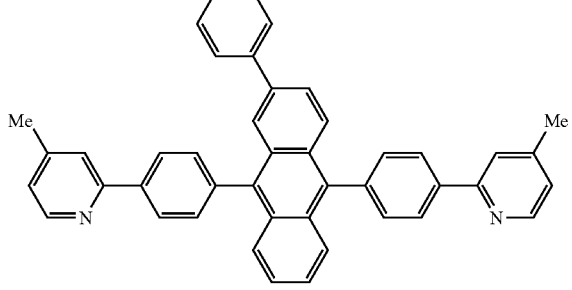
(1-151)
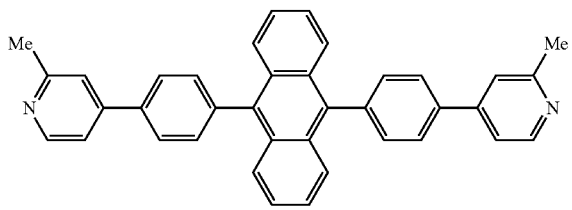
(1-164)
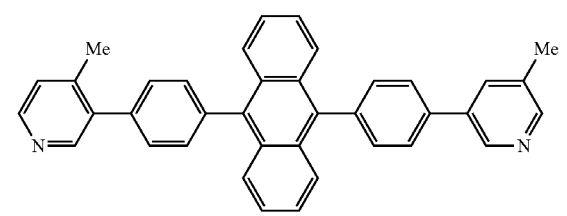
(1-236)
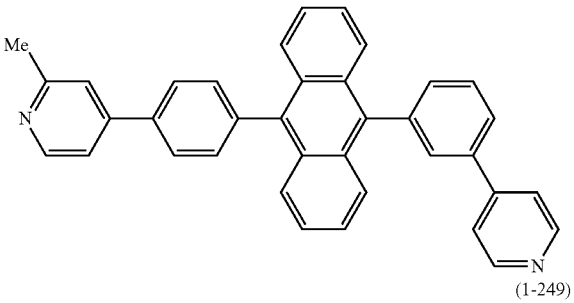
(1-249)
(1-262)
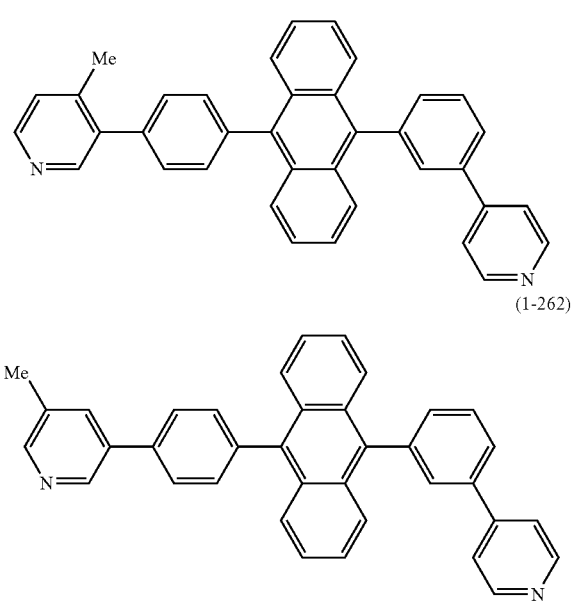
[10] The anthracene derivative according to [1], which is represented by the following formula (1-46), formula (1-68), formula (1-71), formula (1-72) or formula (1-110):
(1-46)
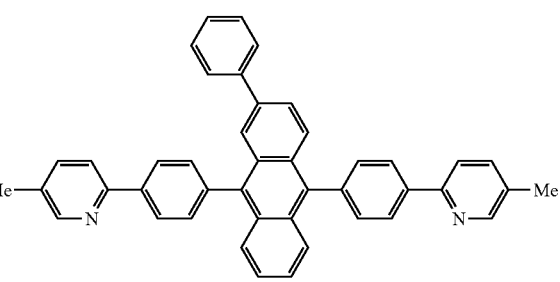
(1-68)
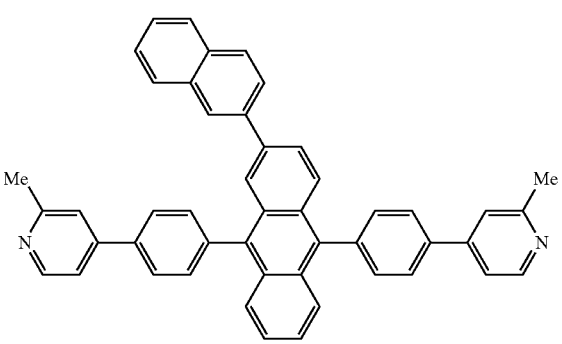

-continued (1-71)

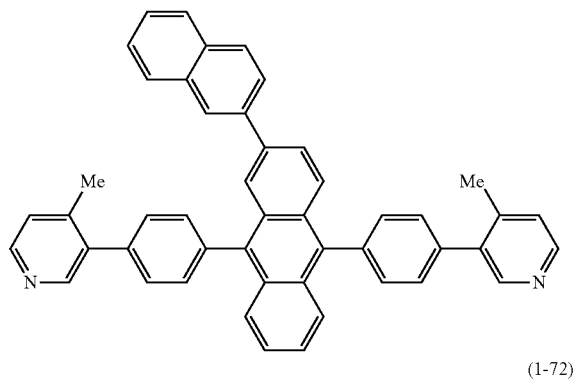

(1-72)

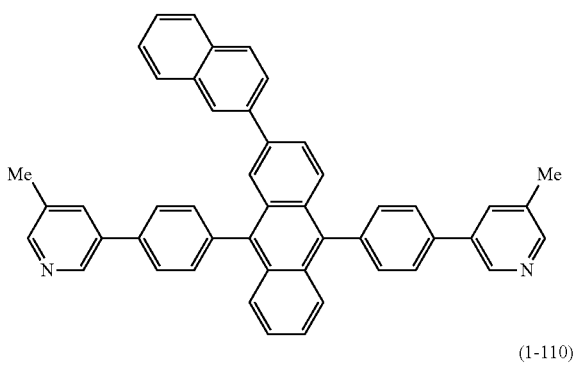

(1-110)

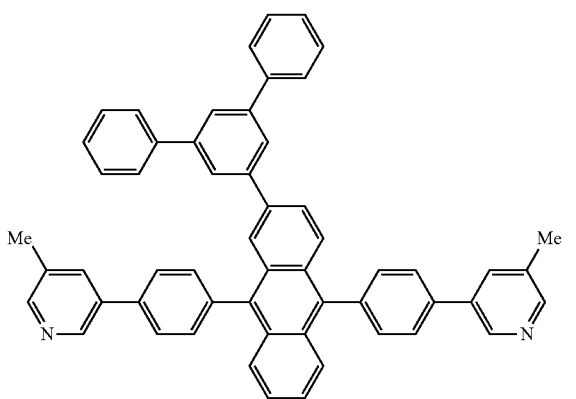

[11] An electron transport material containing the anthracene derivative according to any of [1] to [10].

[12] An organic electroluminescent element having a pair of electrodes consisting of an anode and a cathode, a luminescent layer arranged between the pair of electrodes, and an electron transport layer and/or an electron injection layer, which are arranged between the cathode and the luminescent layer, and contain the electron transport material according to [11].

[13] The organic electroluminescent element according to [12], wherein at least one of the electron transport layer and the electron injection layer contains further at least one selected from the group consisting of a quinolinol metal complex, a pyridine derivative, a bipyridine derivative, a phenanthroline derivative, a borane derivative and a benzimidazole derivative.

[14] The organic electroluminescent element according to [12] or [13], wherein at least one of the electron transport layer and the electron injection layer contains further at least one selected from the group consisting of an alkali metal, an alkaline earth metal, a rare earth metal, an oxide of an alkali metal, a halide of an alkali metal, an oxide of an alkaline earth metal, a halide of an alkaline earth metal, an oxide of a rare earth metal, a halide of a rare earth metal, an organic complex of an alkali metal, an organic complex of an alkaline earth metal and an organic complex of a rare earth metal.

[15] A display device equipped with the organic electroluminescent element according to any of [12] to [14].

[16] A lighting device equipped with the organic electroluminescent element according to any of [12] to [14].

Advantageous Effects of Invention

According to a preferable aspect of the present invention, an organic electroluminescent element excellent in property, particularly, of an external quantum efficiency and a device life can be obtained. A preferable electron transport material of the present invention can be equivalent to, or excellent over the previous material also regarding a driving voltage. Therefore, according to a preferable aspect of the present invention, not only excellent external quantum efficiency and device life can be realized, but also balance between a driving voltage can be made to be excellent. A preferable electron transport material of the present invention is suitable for, particularly, a blue luminescent element, and according to this electron transport material, a blue luminescent element having a device life comparable to that of a red or green luminescent element can be produced. Furthermore, by using this organic electroluminescent element, a high performance display device of full color displaying or the like can be obtained.

BRIEF DESCRIPTION OF DRAWINGS

FIG. 1 is a schematic cross-sectional view showing the organic electroluminescent element according to the present embodiment.

BEST MODE FOR CARRYING OUT THE INVENTION

1. Compound Represented by Formula (1)

The anthracene derivative of the present invention will be explained in detail. The anthracene derivative of the present invention is a compound represented by the following formula (1).

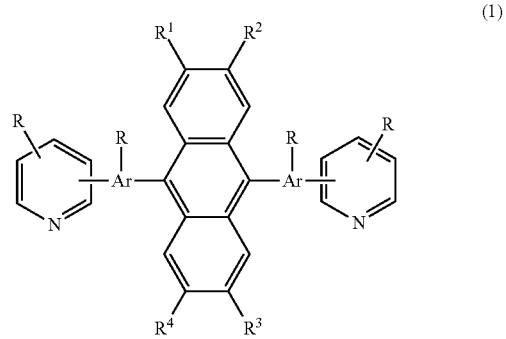

(1)

Ars in the formula (1) can be each independently selected as appropriate from divalent or trivalent benzene or naphthalene, two Ars may be different or the same, and from a view point of easiness of synthesis of the anthracene derivative, two Ars are preferably the same. In addition, "divalent" in "divalent or trivalent benzene or naphthalene" means that in the case where a substituent R with which Ar is substituted is hydrogen, Ar binds to anthracene and pyridine, and "trivalent" means that in the case where a substituent R with which Ar is substituted is an alkyl, Ar binds to anthracene, pyridine and an alkyl.

Ar binds to pyridine to form a "moiety consisting of Ar and pyridine", and this moiety binds to anthracene, for example, as a group represented by any of the following formula (Py-1) to formula (Py-12).

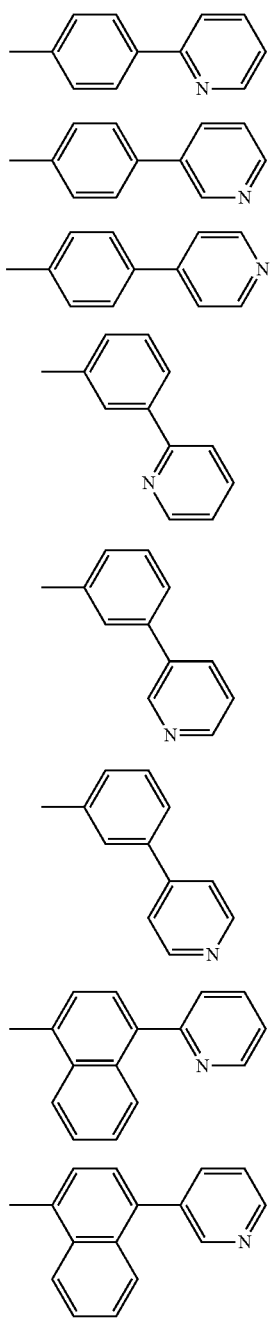

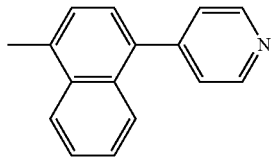

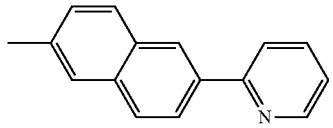

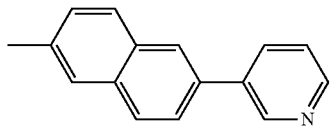

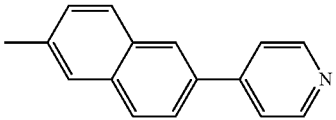

Among these groups, a group represented by any of the above formula (Py-1) to formula (Py-9) is preferable, and a group represented by any of the above formula (Py-1) to formula (Py-6) is more preferable. Two "moieties consisting of Ar and pyridine" which bind to anthracene may have the same or different structures, and from a view point of easiness of synthesis of the anthracene derivative, the two moieties have the same structure. However, from a view point of device property, it is also preferable that two "moieties consisting of Ar and pyridine" have the same or different structures.

The alkyl having a carbon number of 1 to 6 in R in the formula (1) may be either straight or branched. That is, the alkyl is a straight alkyl having a carbon number of 1 to 6 or a branched alkyl having a carbon number of 3 to 6. More preferably, the alkyl is an alkyl having a carbon number of 1 to 4 (branched alkyl having a carbon number of 3 to 4). Examples thereof include methyl, ethyl, n-propyl, isopropyl, n-butyl, isobutyl, s-butyl, t-butyl, n-pentyl, isopentyl, neopentyl, t-pentyl, n-hexyl, 1-methylpentyl, 4-methyl-2-pentyl, 3,3-dimethylbutyl and 2-ethylbutyl. Methyl, ethyl, n-propyl, isopropyl, n-butyl, isobutyl, s-butyl or t-butyl is preferable, methyl, ethyl or t-butyl is more preferable, and methyl is particularly preferable.

Four Rs binding to Ar and pyridine may be each independently either hydrogen or an alkyl having a carbon number of 1 to 6, but not all Rs are hydrogen simultaneously. In addition, an aspect may be either an aspect in which two Rs binding to Ar are both hydrogen and two Rs binding to pyridine are both an alkyl having a carbon number of 1 to 6, or an aspect in which two Rs binding to Ar are both an alkyl having a carbon number of 1 to 6 and two Rs binding to pyridine are both hydrogen, and the former is preferable (that is, a position which is substituted with R may be either Ar or pyridine, and is preferably pyridine). Furthermore, an aspect may be an aspect in which two Rs binding to Ar are both hydrogen, and one of two Rs binding to pyridine is an alkyl having a carbon number of 1 to 4, and the other is hydrogen. In addition, regarding an entire structure of a "moiety consisting of Ar and pyridine" including a substituent R, structures on left and right sides of anthracene may be the same or different, and from a view point of easiness of synthesis of the anthracene derivative, those structures are preferably the same. However, from a view point of device property, it is also preferable that structures on left and right sides of anthracene are the same or different.

$R^1$, $R^2$, $R^3$ and $R^4$ in the formula (1) (also referred to as "$R^1$ to $R^4$" hereinbelow) can be each independently selected as appropriate from hydrogen, an alkyl having a carbon number of 1 to 6, a cycloalkyl having a carbon number of 3 to 6 or an aryl having a carbon number of 6 to 20.

The alkyl having a carbon number of 1 to 6 in $R^1$ to $R^4$ in the formula (1) may be either straight or branched. That is, the alkyl is a straight alkyl having a carbon number of 1 to 6 or a branched alkyl having a carbon number of 3 to 6. More preferably, the alkyl is an alkyl having a carbon number of 1 to 4 (branched alkyl having a carbon number of 3 to 4). Examples thereof include methyl, ethyl, n-propyl, isopropyl, n-butyl, isobutyl, s-butyl, t-butyl, n-pentyl, isopentyl, neopentyl, t-pentyl, n-hexyl, 1-methylpentyl, 4-methyl-2-pentyl, 3,3-dimethylbutyl and 2-ethylbutyl. Methyl, ethyl, n-propyl, isopropyl, n-butyl, isobutyl, s-butyl or t-butyl is preferable, and methyl, ethyl or t-butyl is more preferable.

Examples of the cycloalkyl having a carbon number of 3 to 6 in $R^1$ to $R^4$ in the formula (1) include cyclopropyl, cyclobutyl, cyclopentyl, cyclohexyl, methylcyclopentyl, cycloheptyl, methylcyclohexyl, cyclooctyl and dimethylcyclohexyl.

The aryl having a carbon number of 6 to 20 in $R^1$ to $R^4$ in the formula (1) is preferably an aryl having a carbon number of 6 to 16, more preferably an aryl having a carbon number of 6 to 12, and particularly preferably an aryl having a carbon number of 6 to 10.

Examples of the "aryl having a carbon number of 6 to 20" include phenyl, (o-, m-, p-) tolyl, (2,3-, 2,4-, 2,5-, 2,6-, 3,4-, 3,5-) xylyl, mesityl(2,4,6-trimethylphenyl) and (o-, m-, p-) cumenyl which are a monocyclic aryl, (2-, 3-, 4-) biphenylyl which is a dicyclic aryl, (1-, 2-)naphthyl which is a fused dicyclic aryl, terphenylyl(m-terphenyl-2'-yl, m-terphenyl-4'-yl, m-terphenyl-5'-yl, o-terphenyl-3'-yl, o-terphenyl-4'-yl, p-terphenyl-2'-yl, m-terphenyl-2-yl, m-terphenyl-3-yl, m-terphenyl-4-yl, o-terphenyl-2-yl, o-terphenyl-3-yl, o-terphenyl-4-yl, p-terphenyl-2-yl, p-terphenyl-3-yl, p-terphenyl-4-yl) which is a tricyclic aryl, anthracene-(1-, 2-, 9-)yl, acenaphthylene-(1-, 3-, 4-, 5-)yl, fluorene-(1-, 2-, 3-, 4-, 9-)yl and phenalene-(1-, 2-)yl, (1-, 2-, 3-, 4-, 9-) phenanthryl which are a fused tricyclic aryl, triphenylene-(1-, 2-)yl, pyrene-(1-, 2-, 4-)yl and tetracene-(1-, 2-, 5-)yl which are a fused tetracyclic aryl, and perylene-(1-, 2-, 3-)yl which is a fused pentacyclic aryl.

The "aryl having a carbon number of 6 to 20" is preferably phenyl, biphenylyl, terphenylyl or naphthyl, more preferably phenyl, biphenylyl, 1-naphthyl, 2-naphthyl or m-terphenyl-5'-yl, further preferably phenyl, biphenylyl, 1-naphthyl or 2-naphthyl, and most preferably phenyl.

Examples of the anthracene derivative represented by the above formula (1) include, for example, anthracene derivatives represented by the following formula (1-1) to formula (1-329).

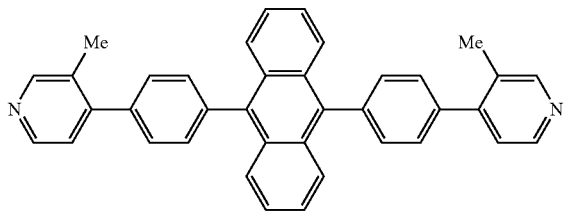
(1-1)

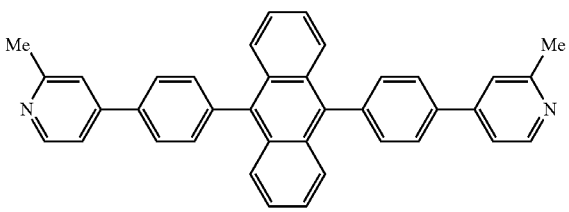
(1-2)

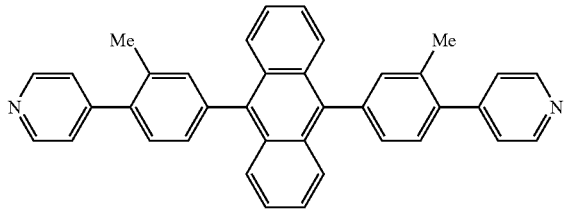
(1-3)

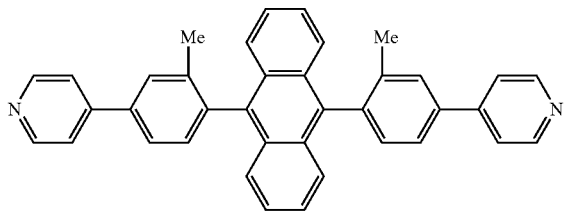
(1-4)

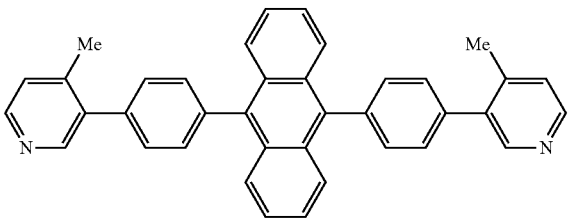
(1-5)

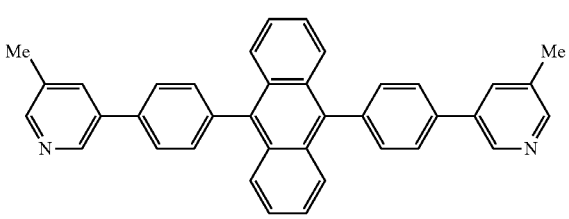
(1-6)

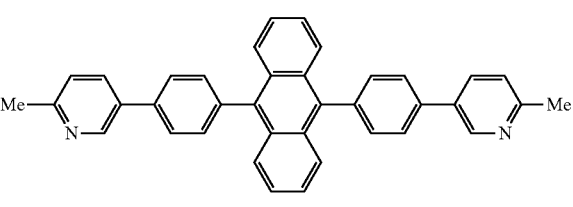
(1-7)

(1-8)
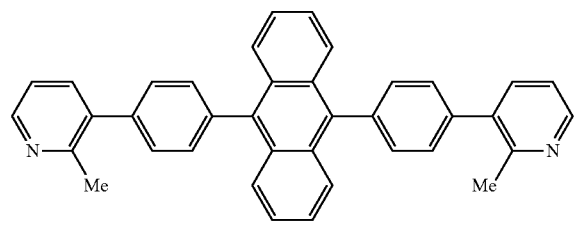
(1-9)
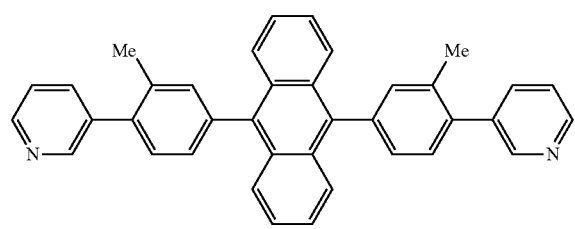
(1-10)
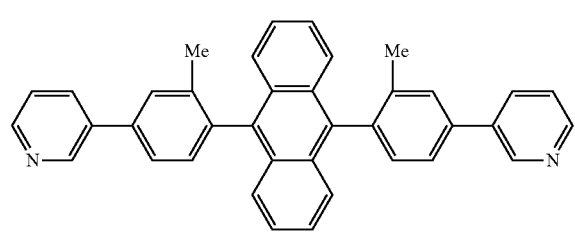
(1-11)
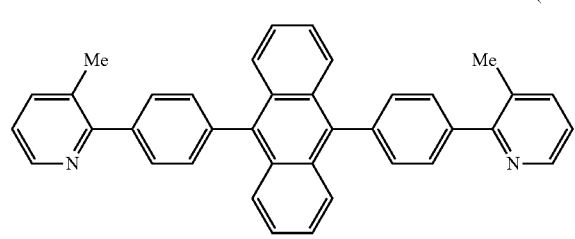
(1-12)
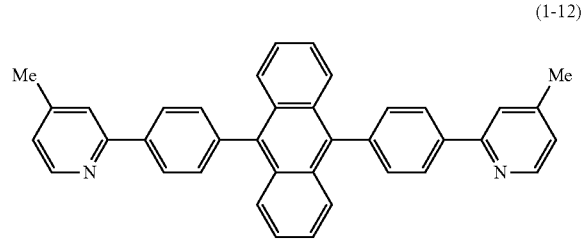
(1-13)
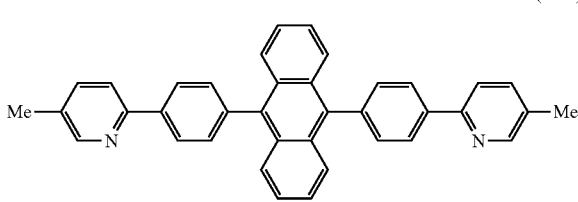
(1-14)
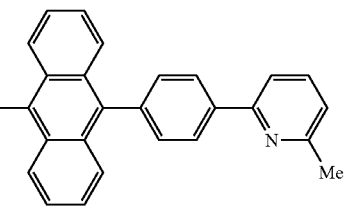
(1-15)
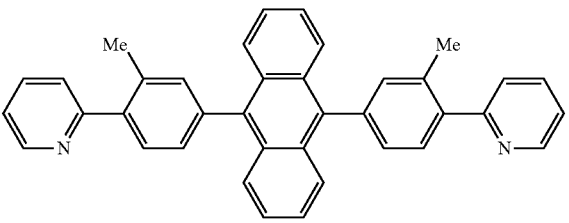
(1-16)
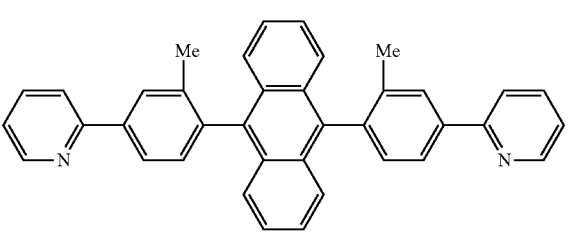
(1-17)
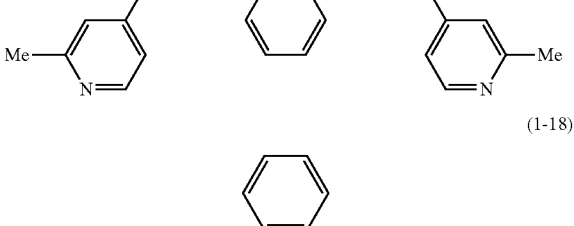
(1-18)
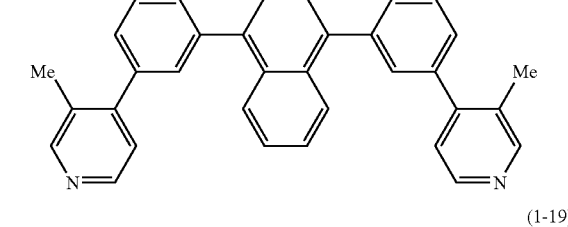
(1-19)
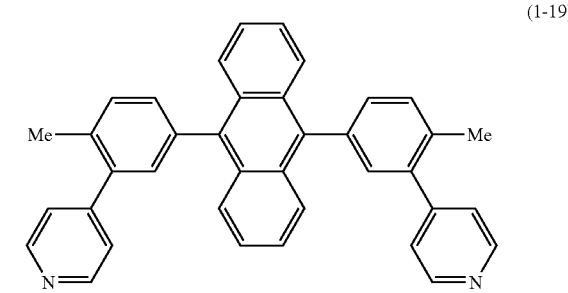

(1-20)
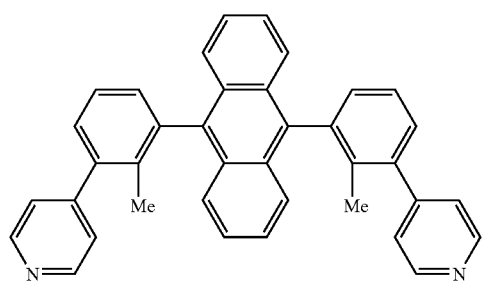
(1-21)
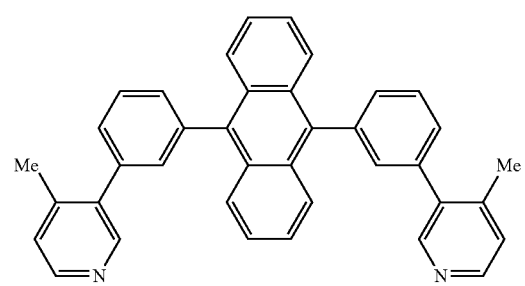
(1-22)
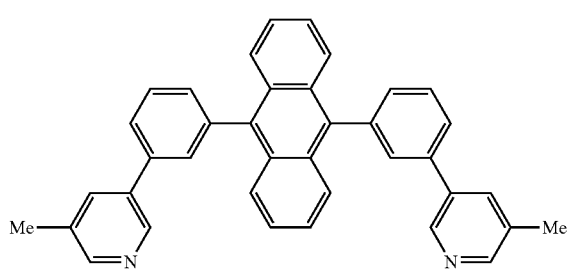
(1-23)
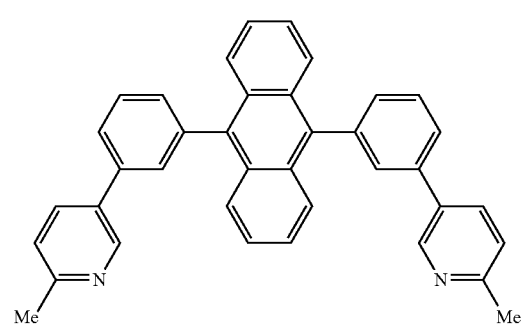
(1-24)
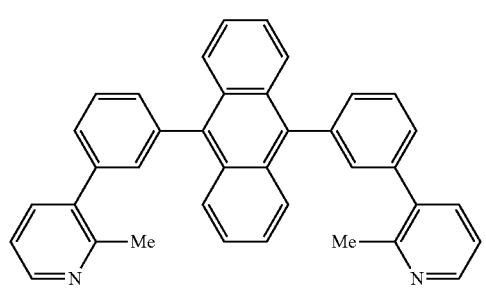
(1-25)
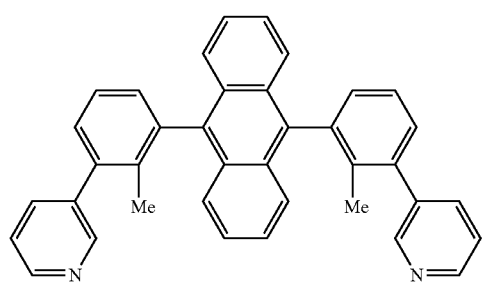
(1-26)
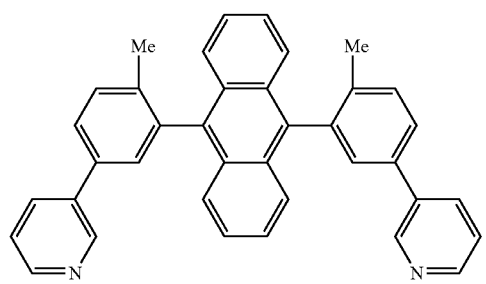
(1-27)
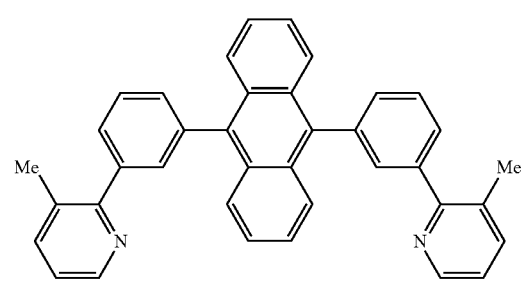
(1-28)
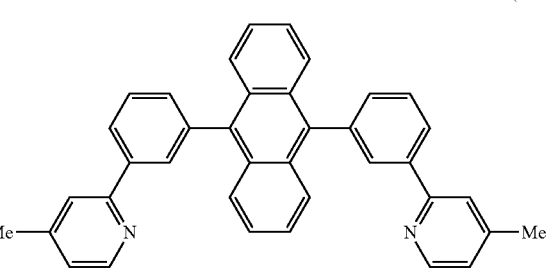
(1-29)
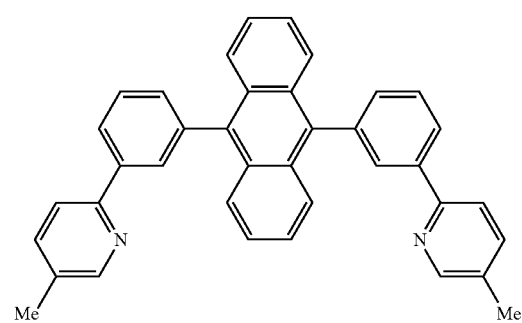

-continued
(1-30)
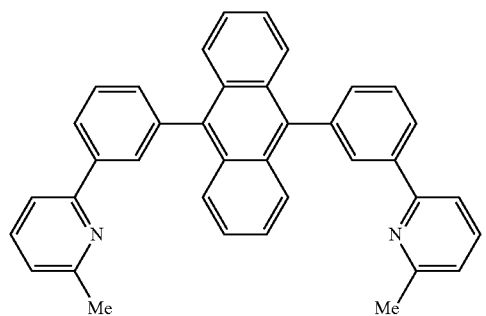
(1-31)
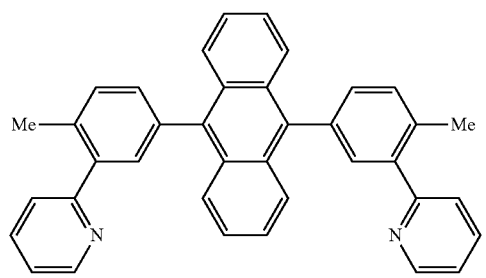
(1-32)
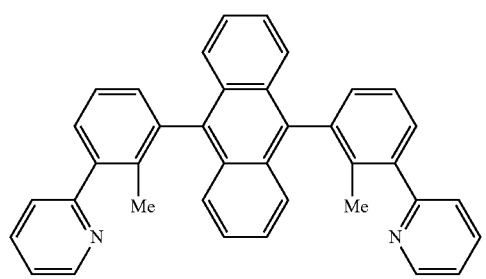
(1-33)
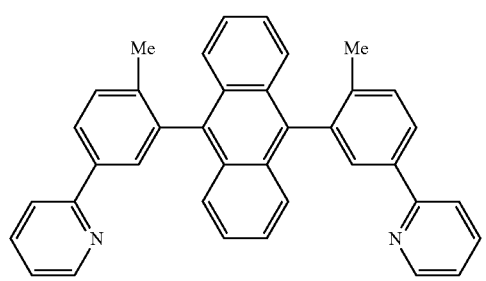
(1-34)
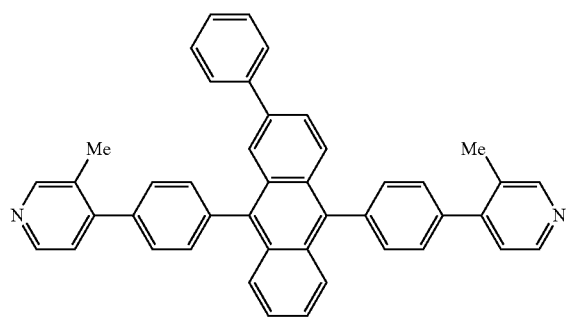
(1-35)
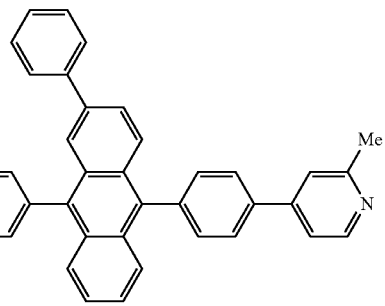
(1-36)
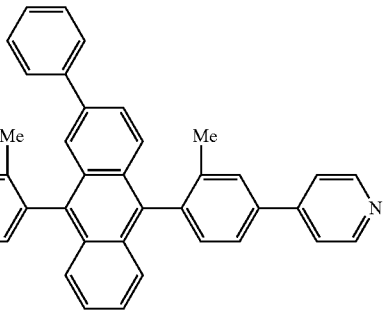
(1-37)
(1-38)
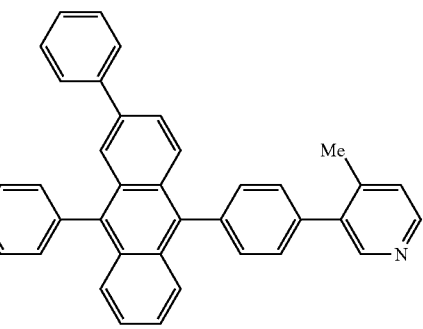

(1-39)
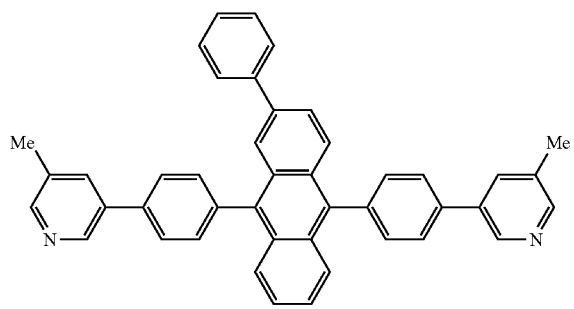
(1-40)
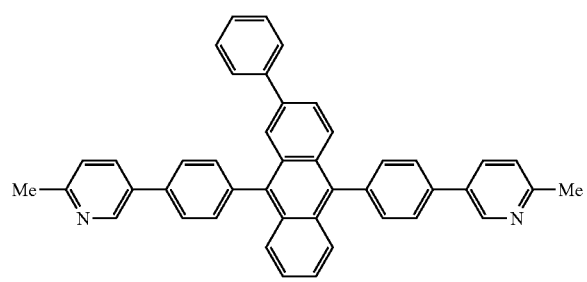
(1-41)
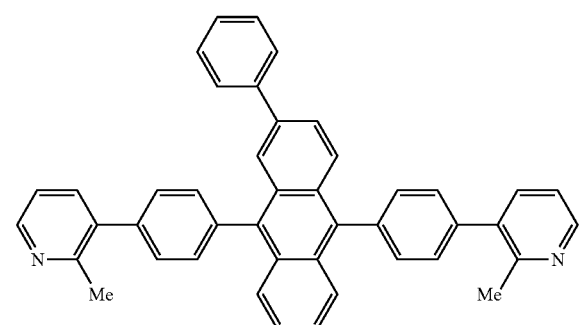
(1-42)
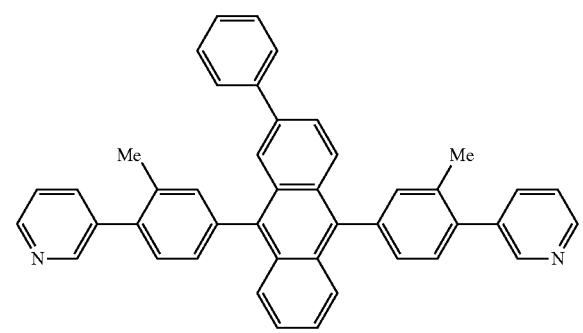
(1-43)
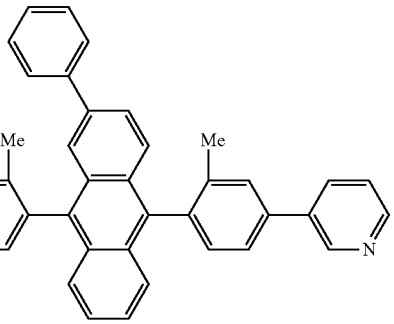
(1-44)
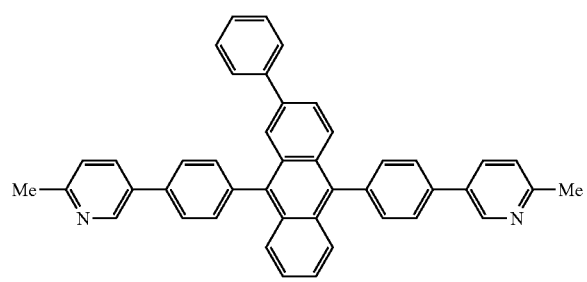
(1-45)
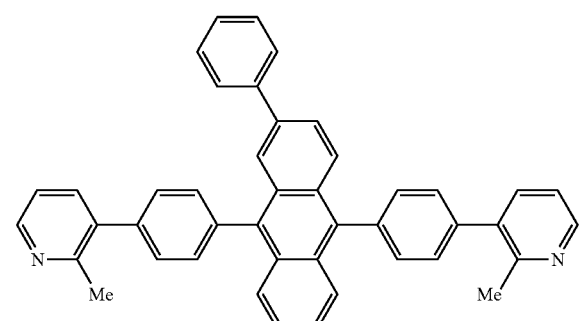
(1-46)
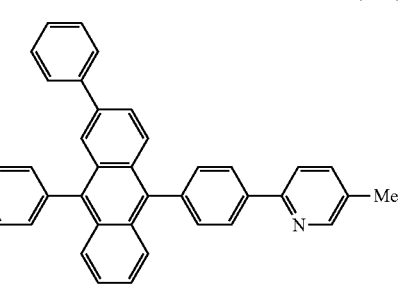
(1-47)
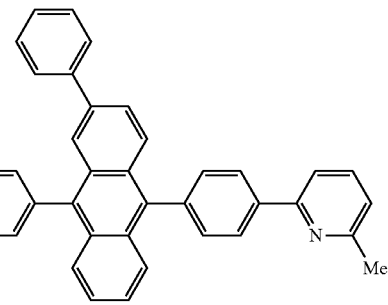

(1-48)
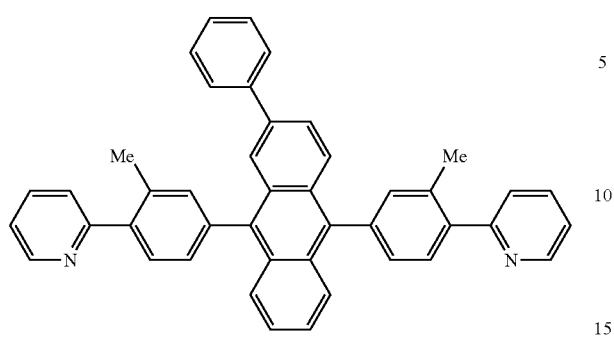
(1-49)
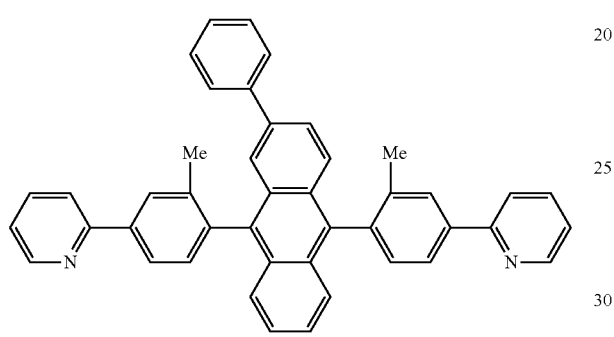
(1-50)
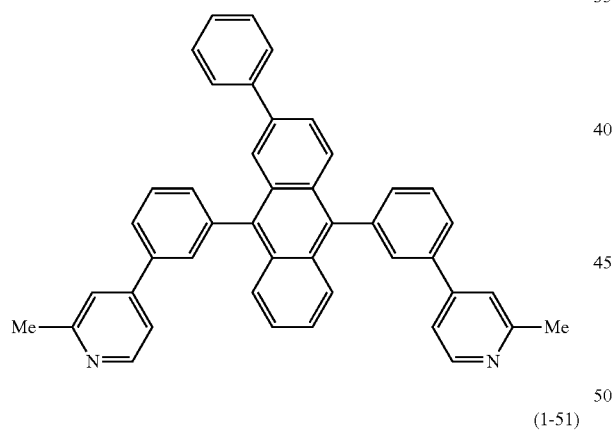
(1-51)
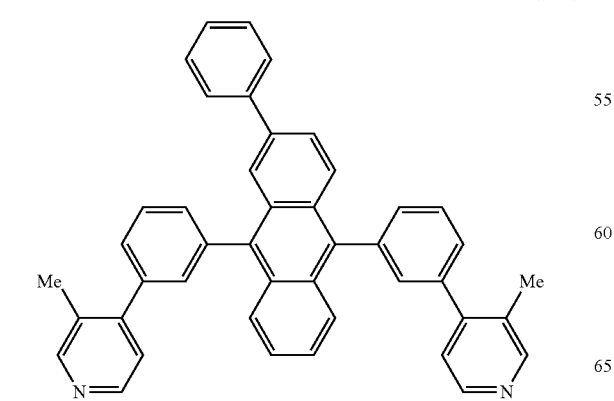
(1-52)
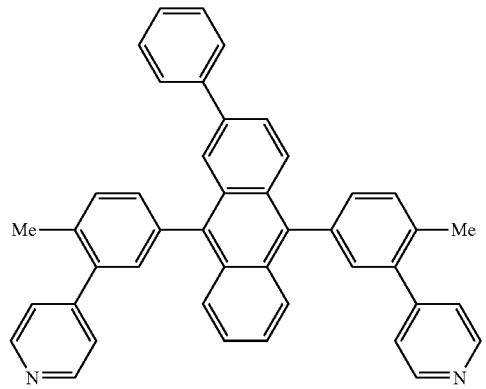
(1-53)
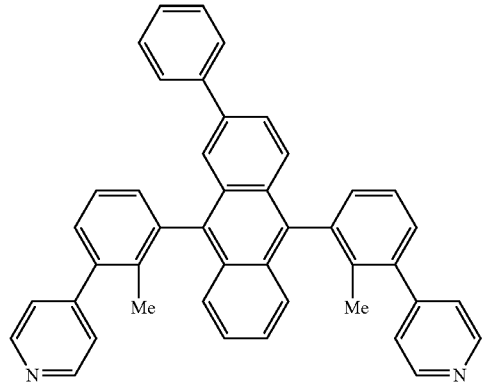
(1-54)
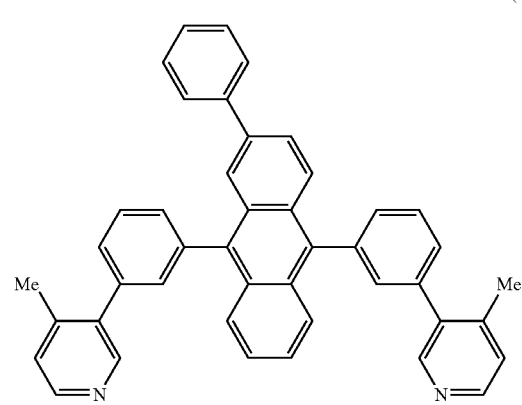
(1-55)
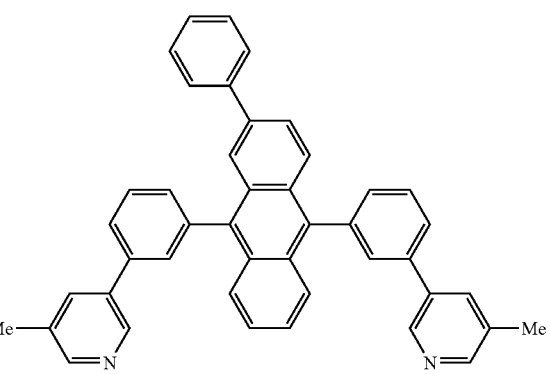

(1-56)
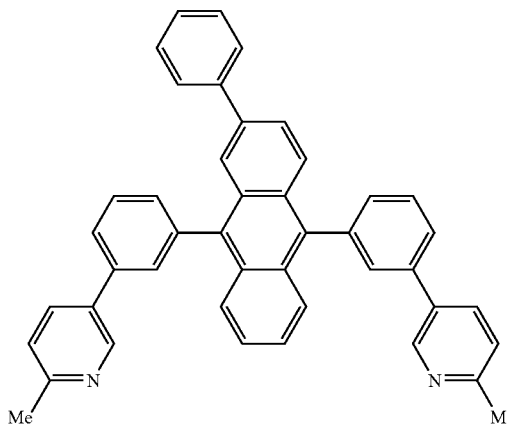
(1-57)
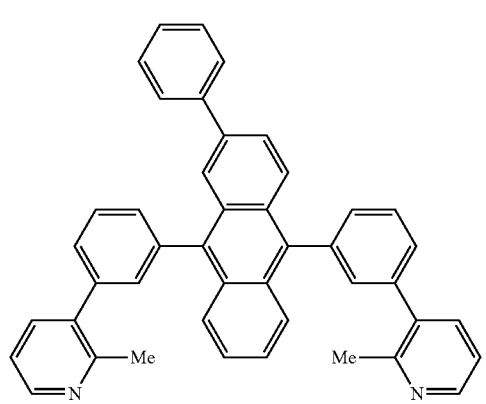
(1-58)
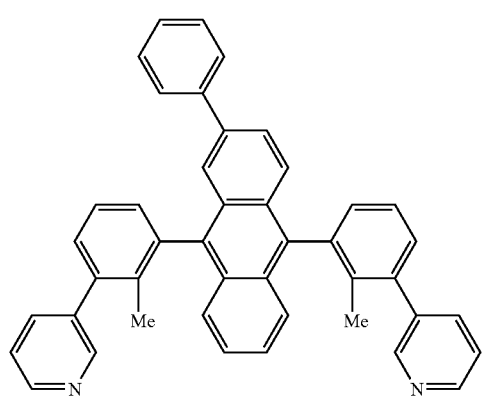
(1-59)
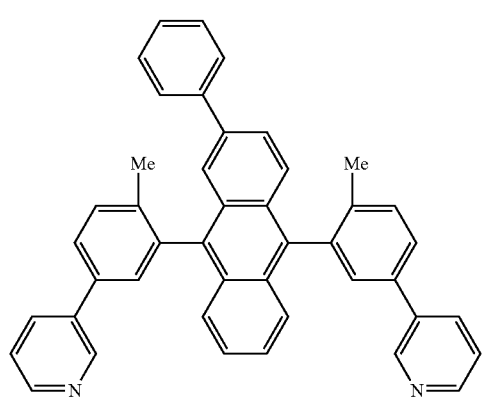
(1-60)
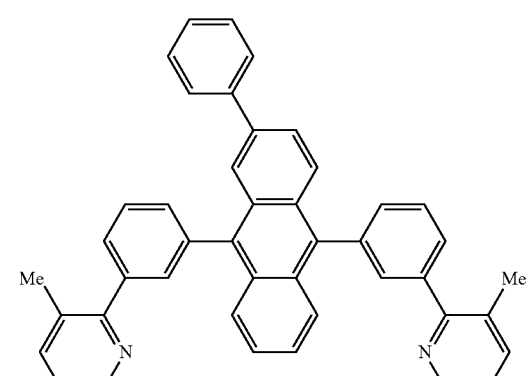
(1-61)
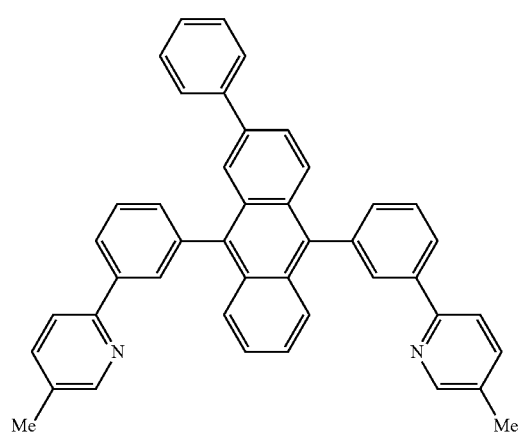
(1-62)

(1-63)
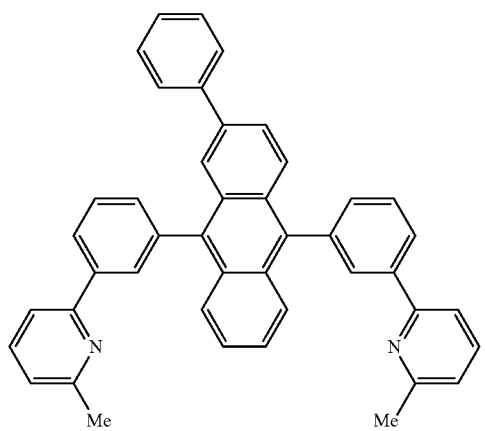
(1-64)
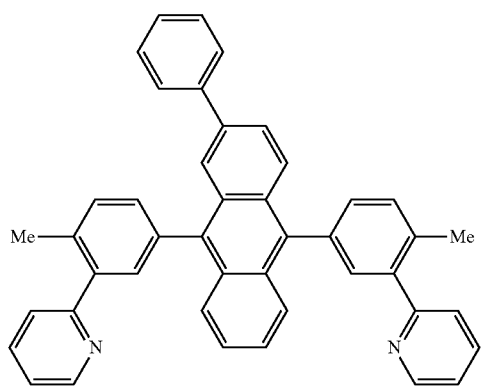
(1-65)
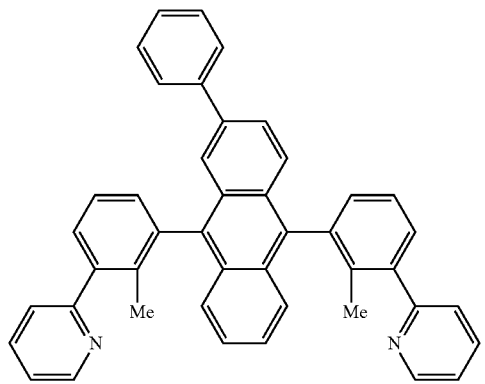
(1-66)
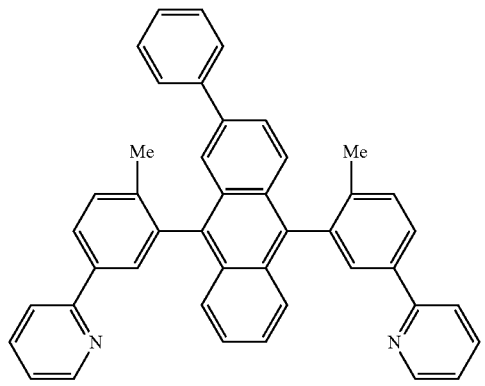
(1-67)
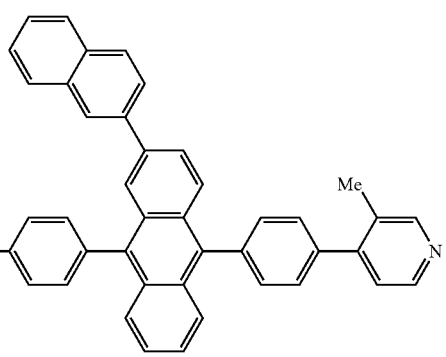
(1-68)
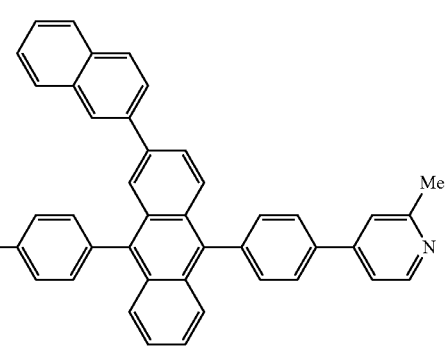
(1-69)
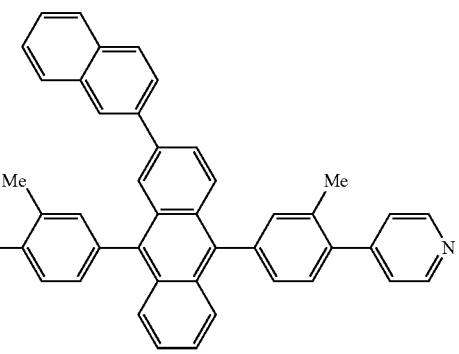
(1-70)
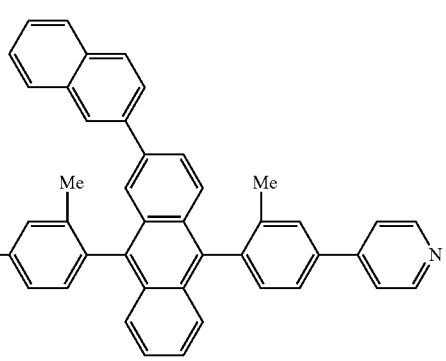

(1-71)
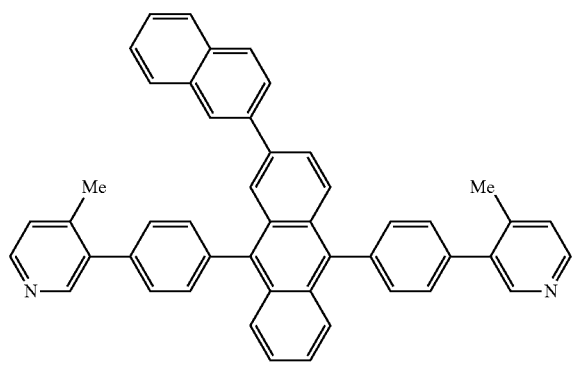
(1-72)
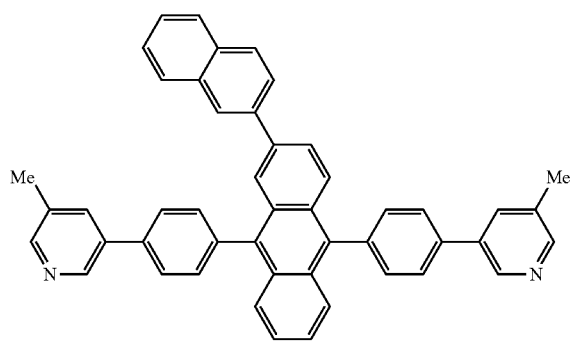
(1-73)
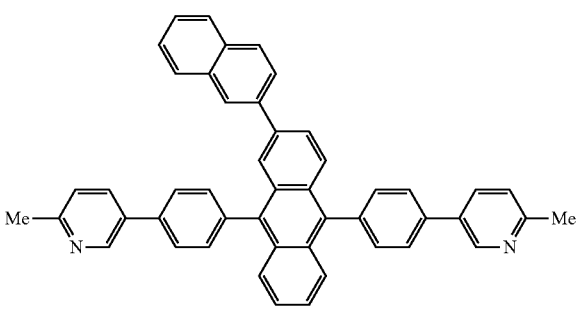
(1-74)
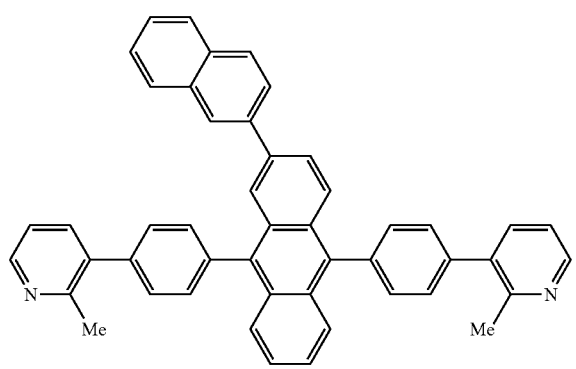
(1-75)
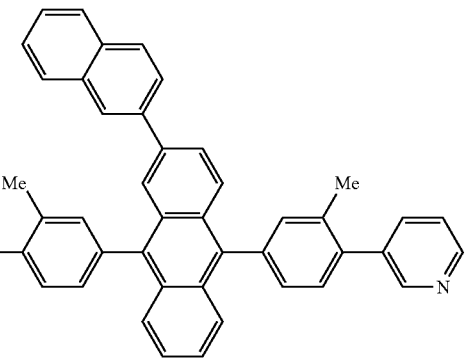
(1-76)
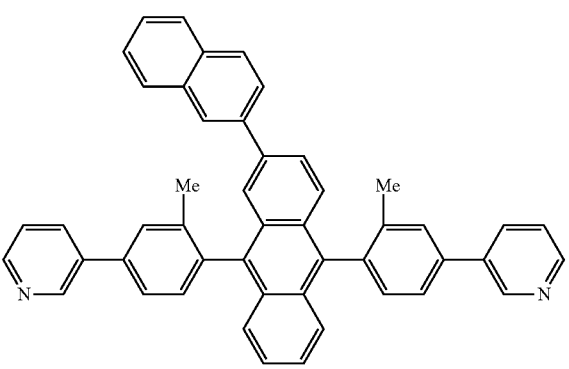
(1-77)
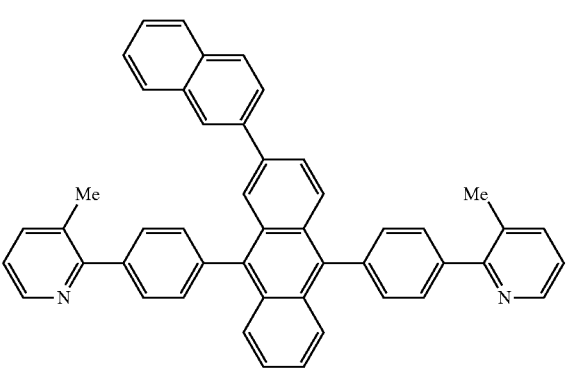
(1-78)
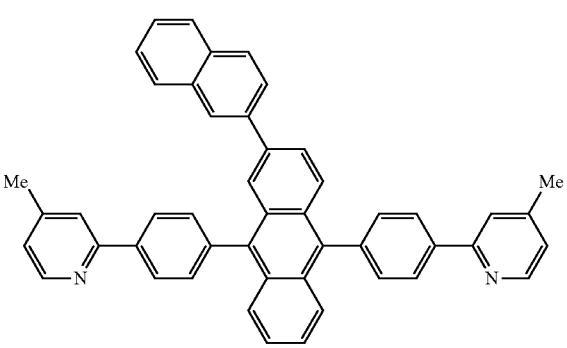

(1-79)
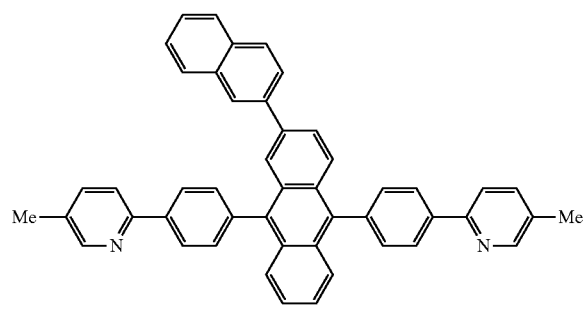
(1-83)
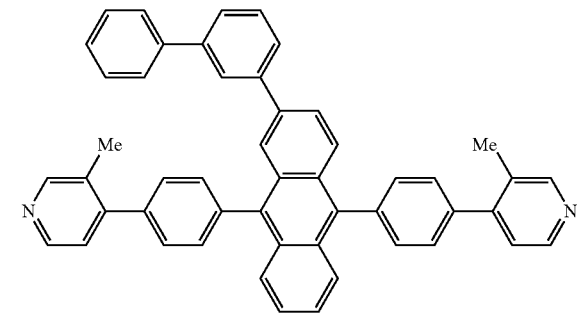
(1-80)
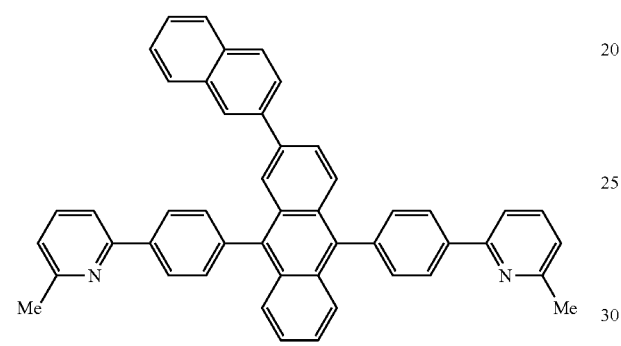
(1-84)
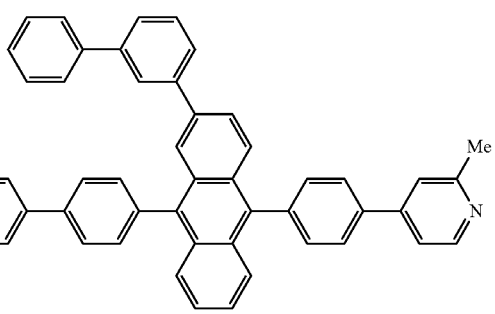
(1-81)
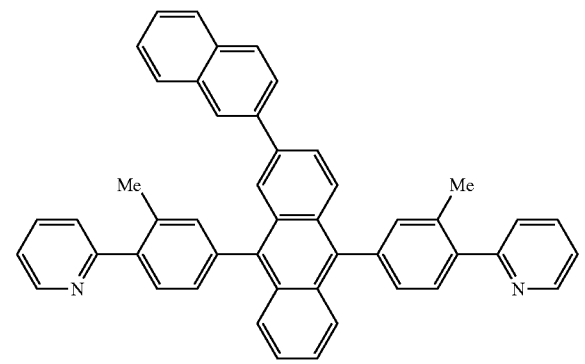
(1-85)
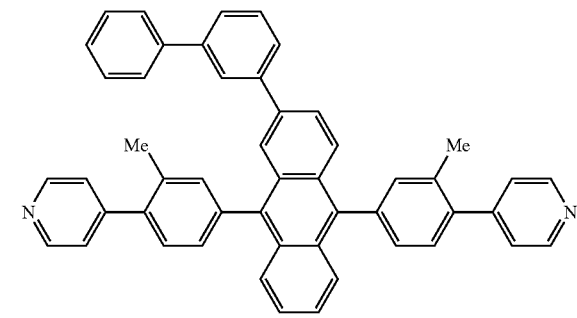
(1-82)
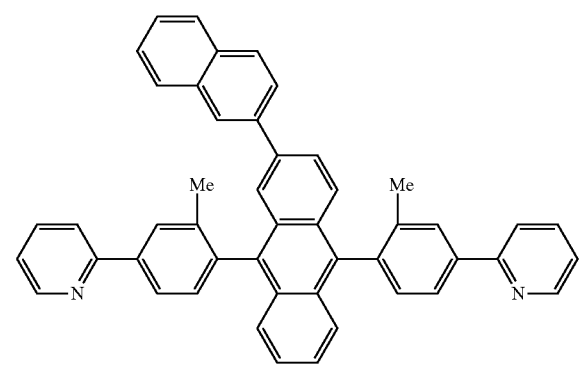
(1-86)
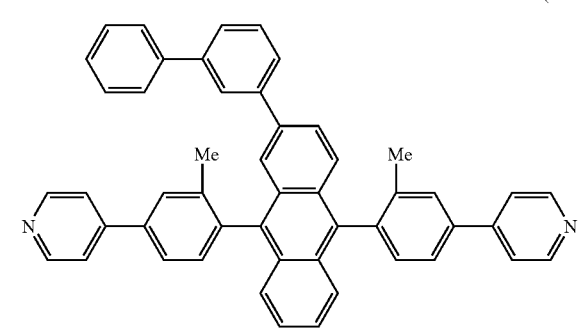

(1-87)
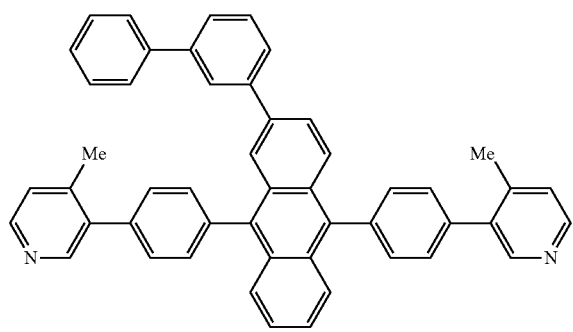
(1-88)
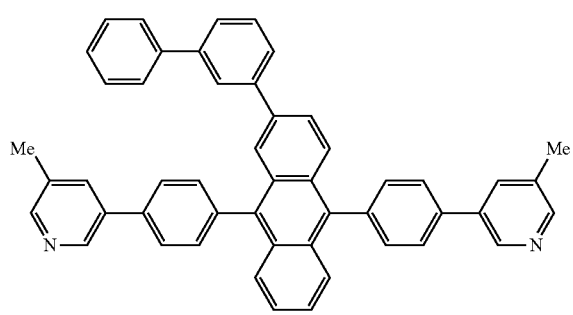
(1-89)
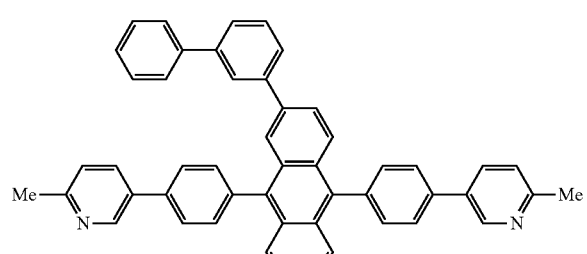
(1-90)
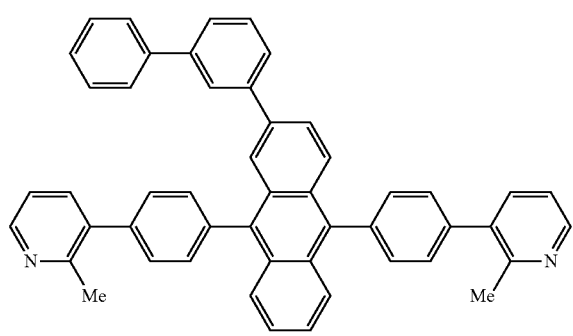
(1-91)
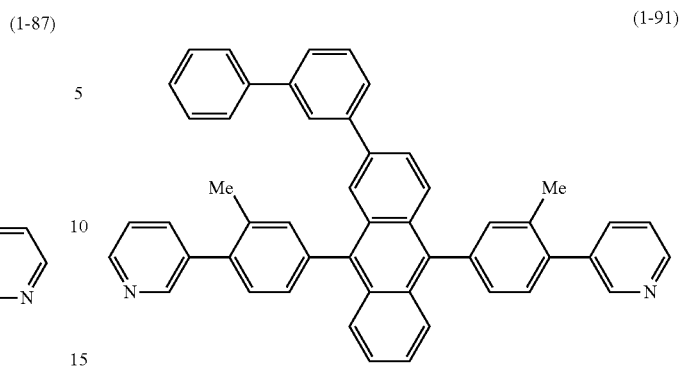
(1-92)
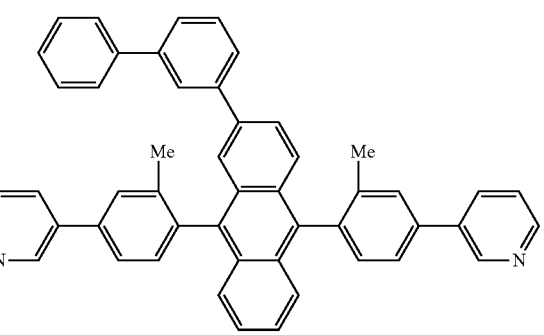
(1-93)
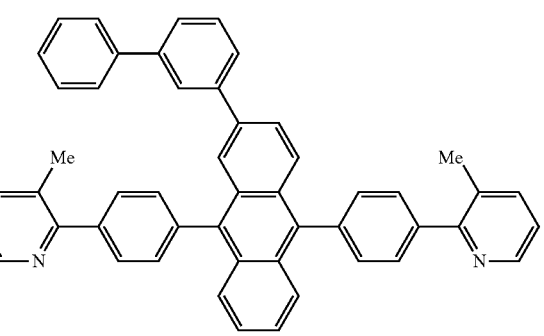
(1-94)
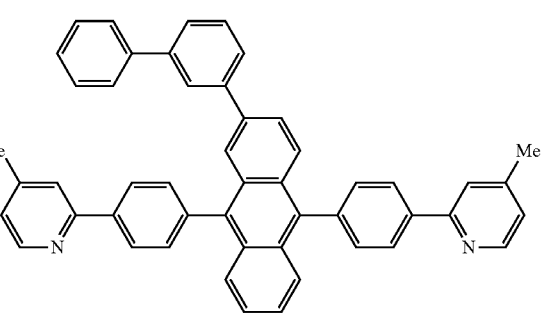

(1-95)
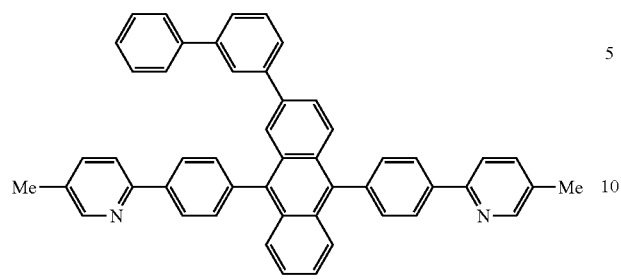
(1-99)
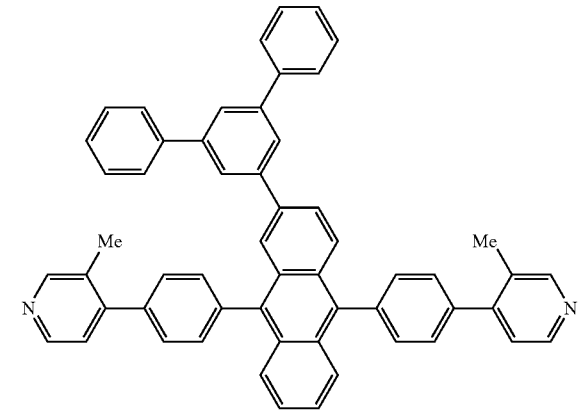
(1-96)
(1-100)
(1-97)
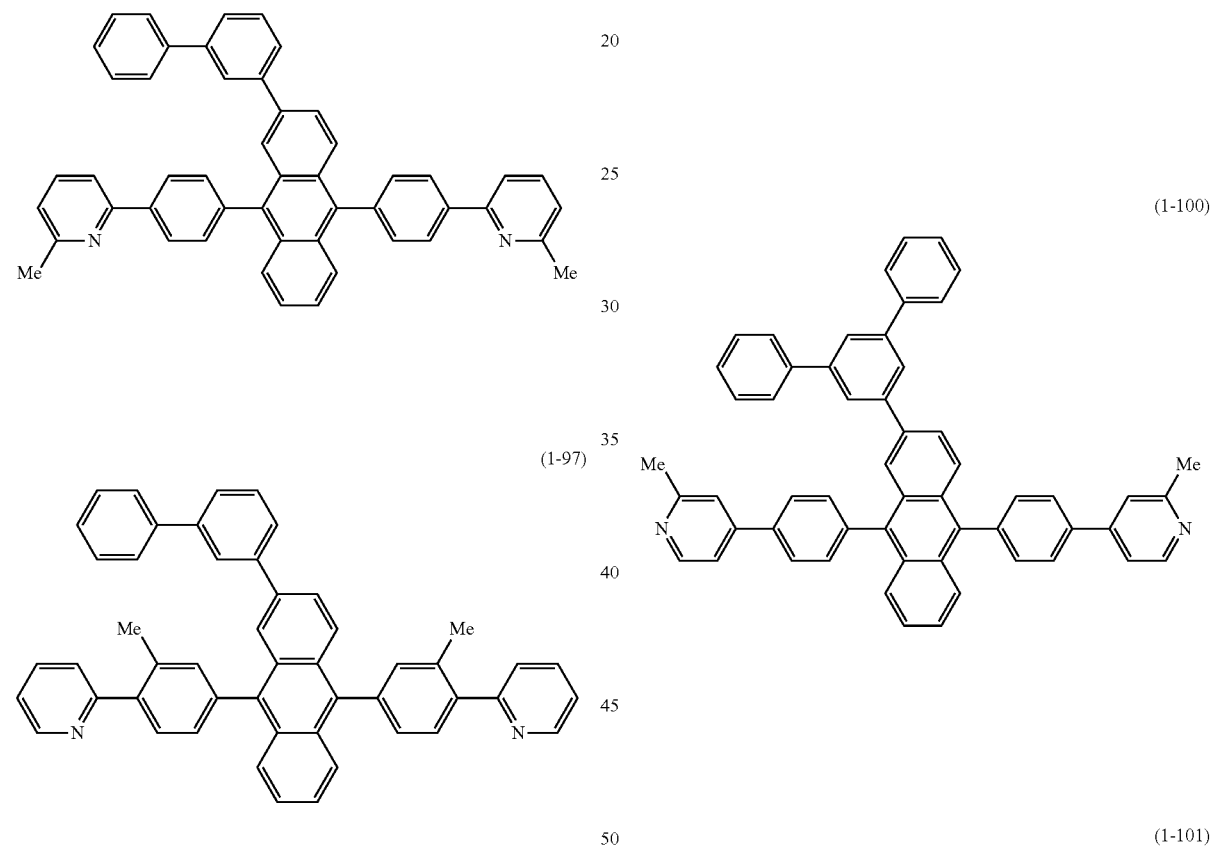
(1-101)
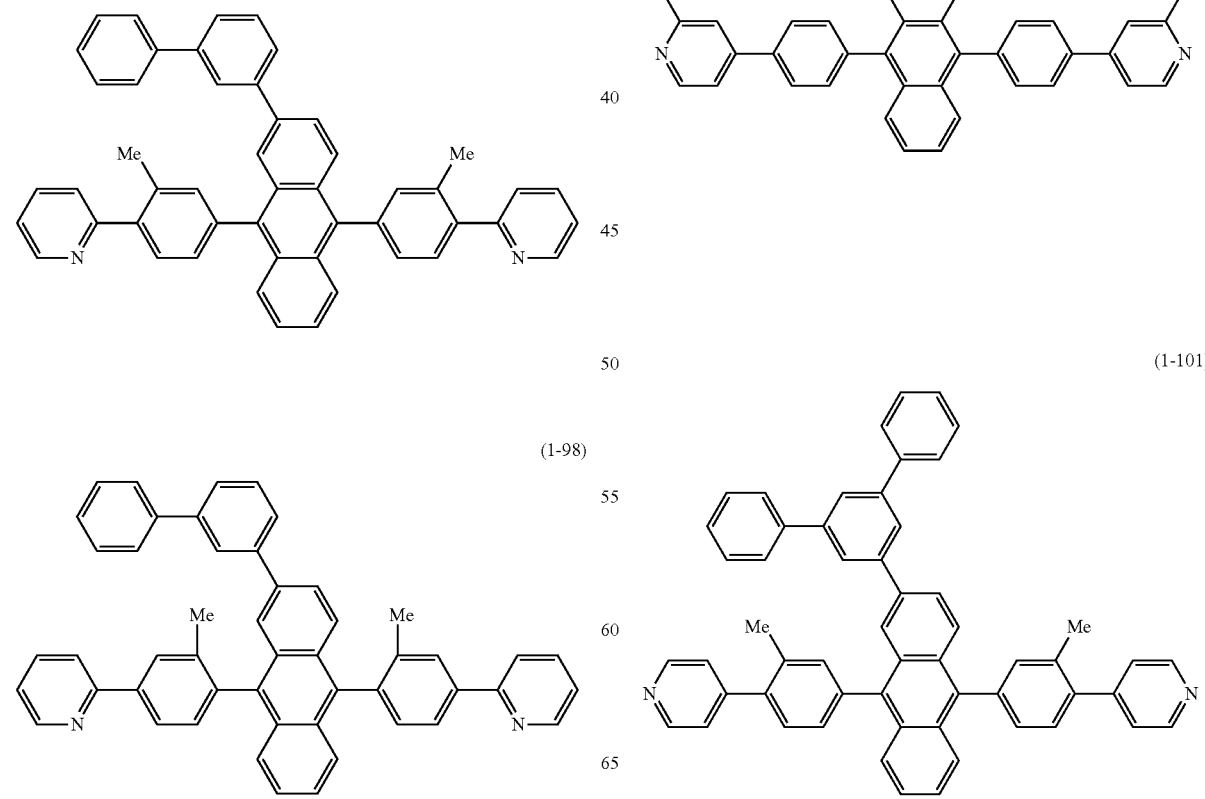
(1-98)

(1-102)
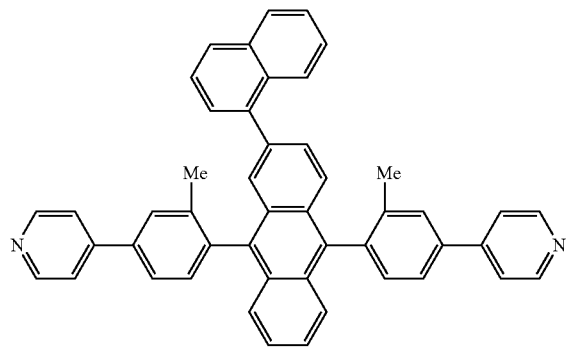
(1-103)
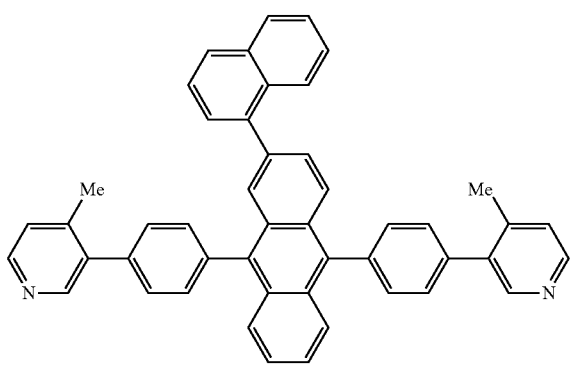
(1-104)
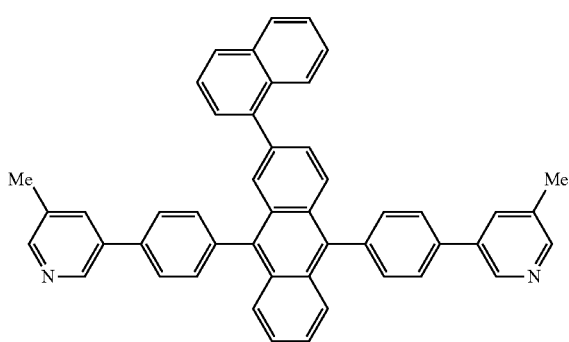
(1-105)
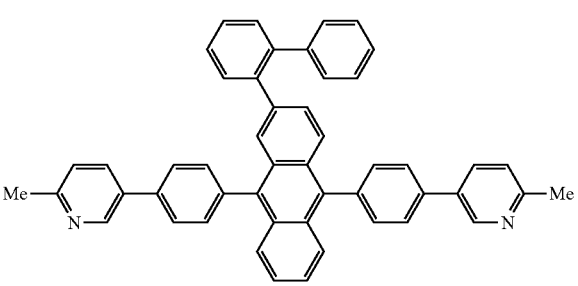
(1-106)
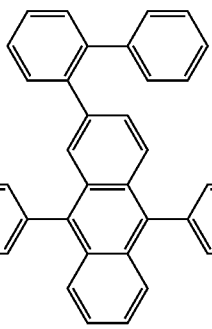
(1-107)
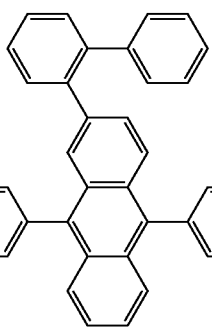
(1-108)
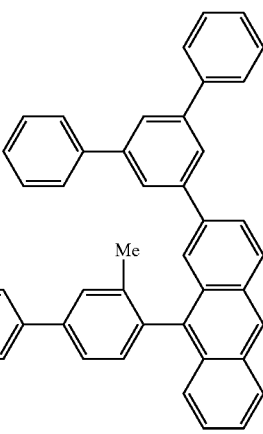
(1-109)
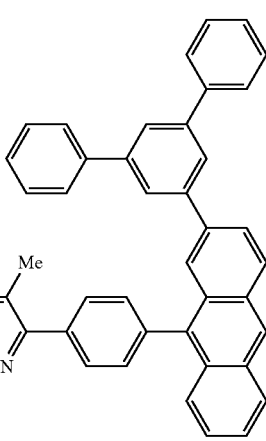

(1-110)
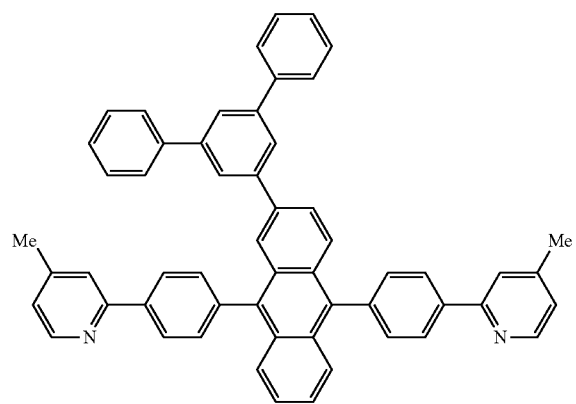
(1-111)
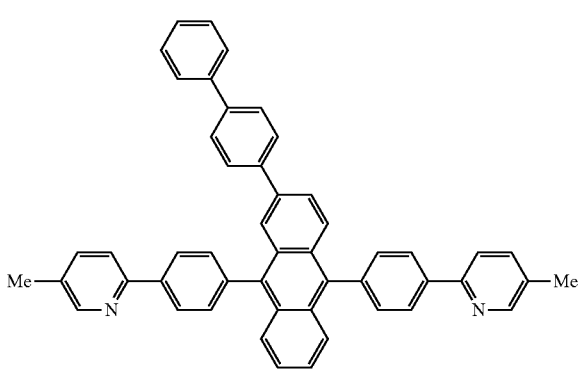
(1-112)
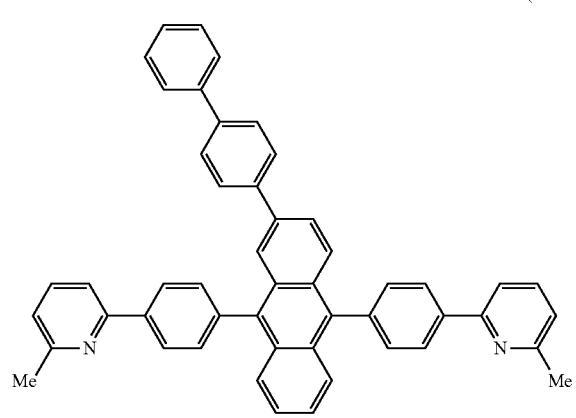
(1-113)
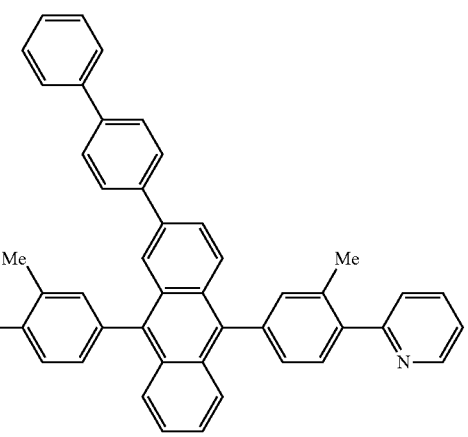
(1-114)
(1-115)
(1-116)
(1-117)
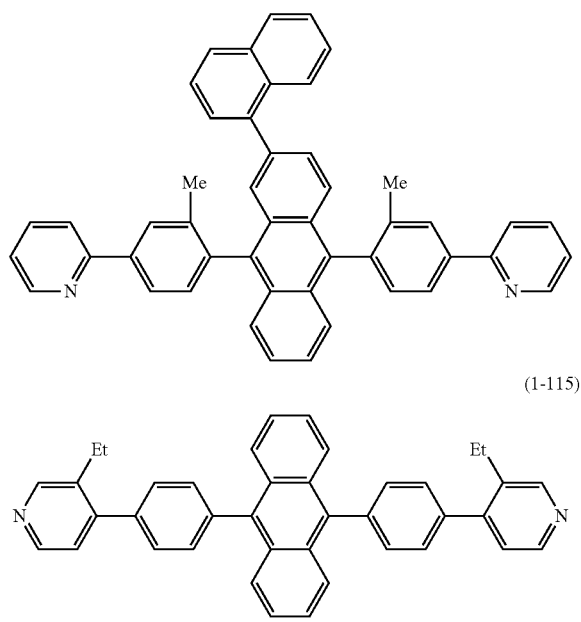
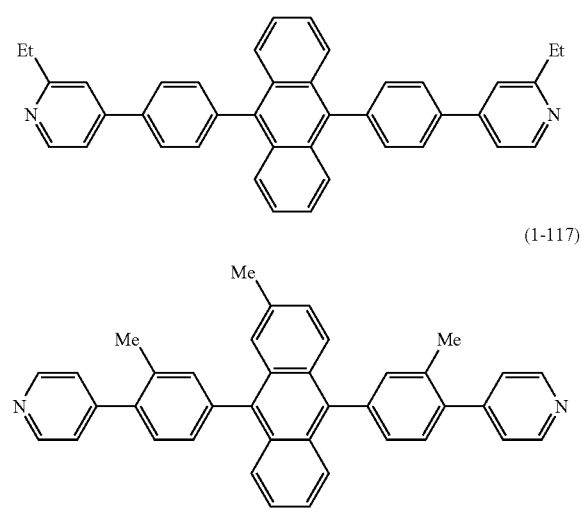

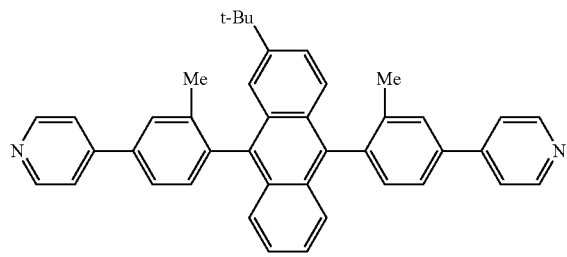
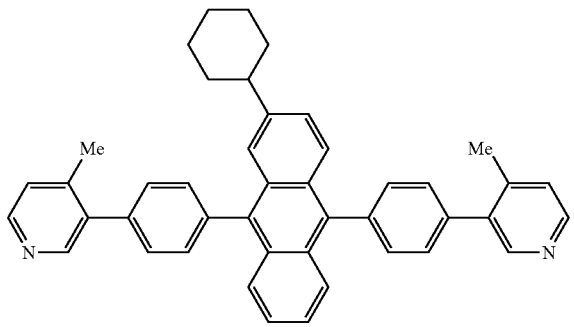
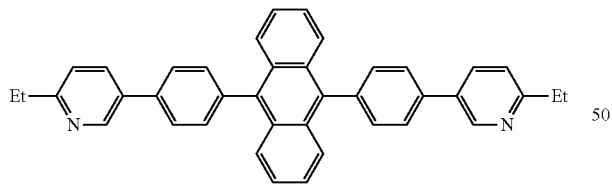
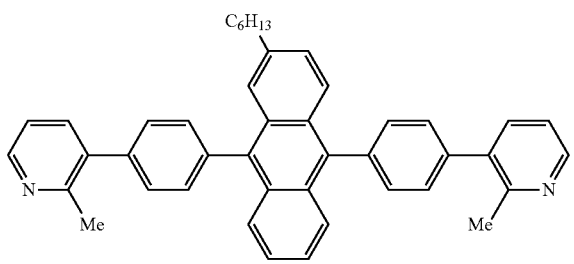
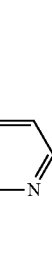
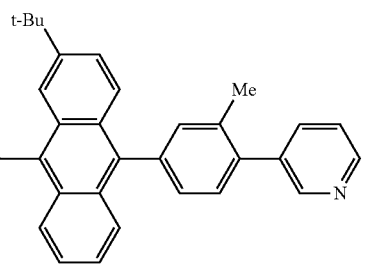

(1-128)
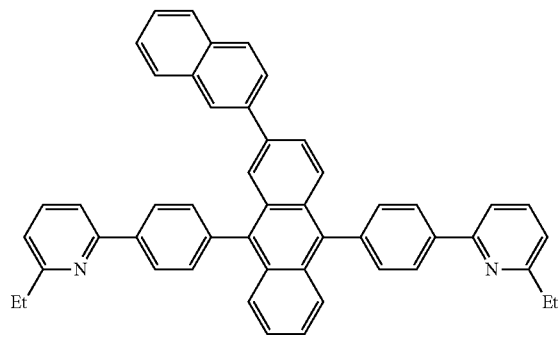
(1-129)
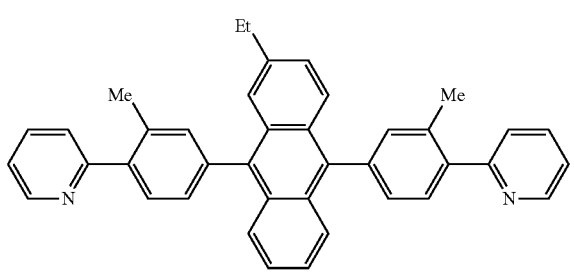
(1-130)
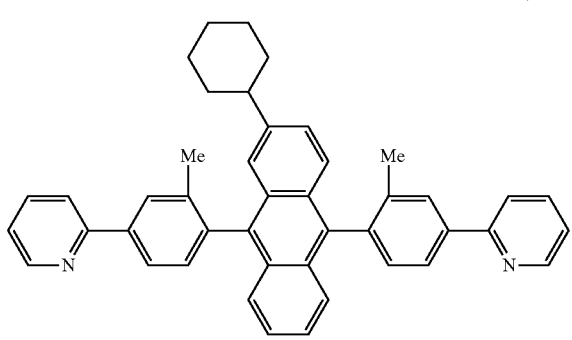
(1-131)
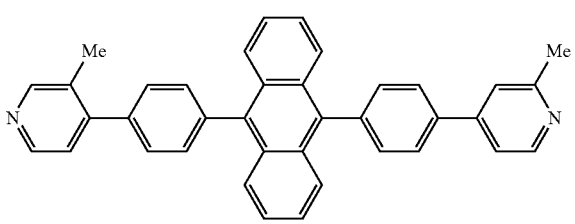
(1-132)
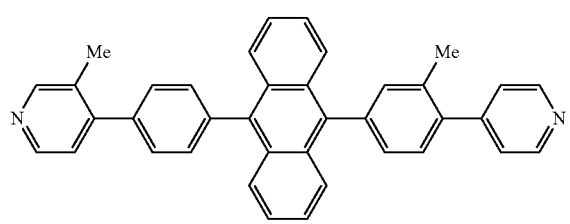
(1-133)
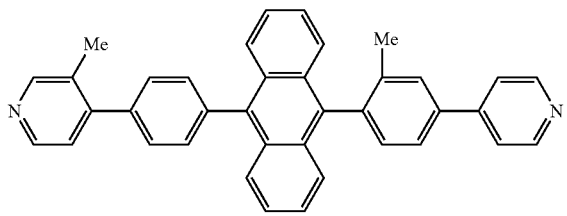
(1-134)
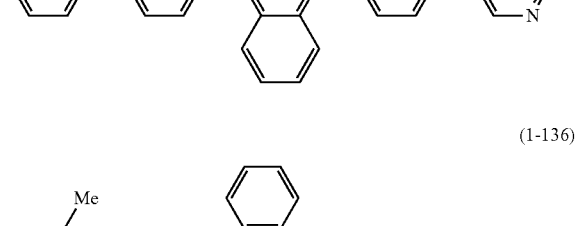
(1-135)
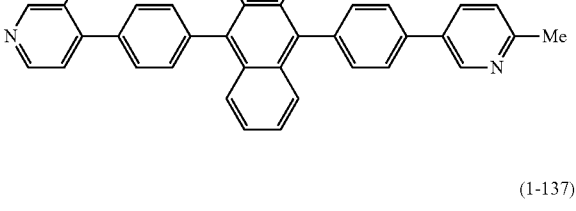
(1-136)
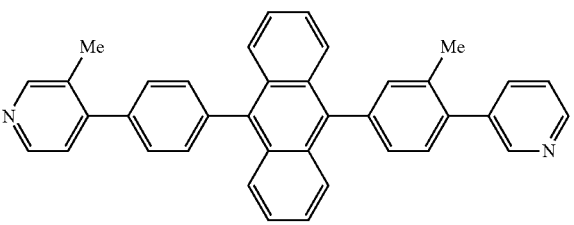
(1-137)
(1-138)

(1-139)
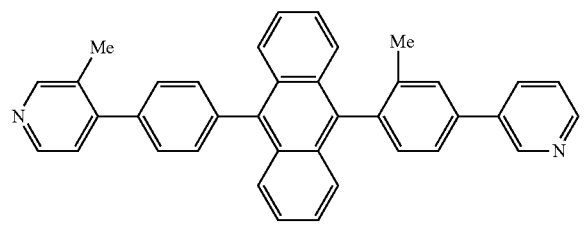
(1-140)
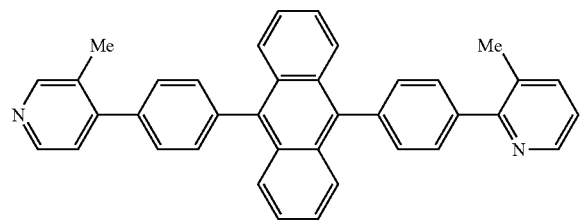
(1-141)
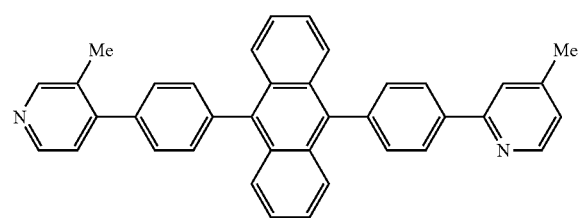
(1-142)
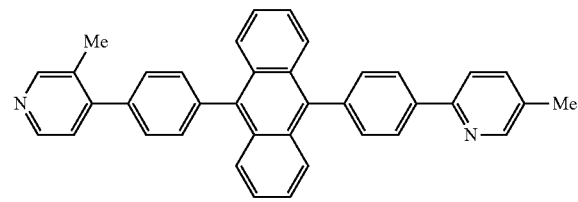
(1-143)
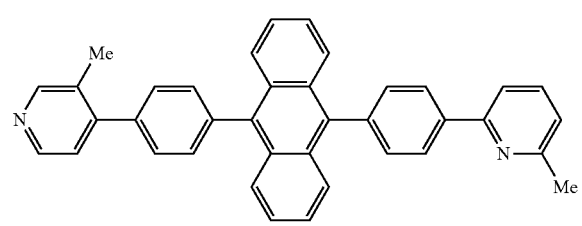
(1-144)
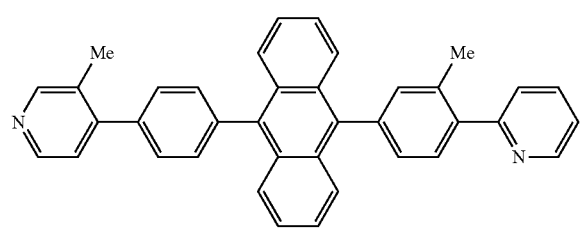
(1-145)
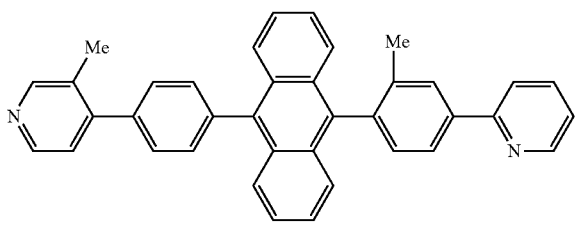
(1-146)
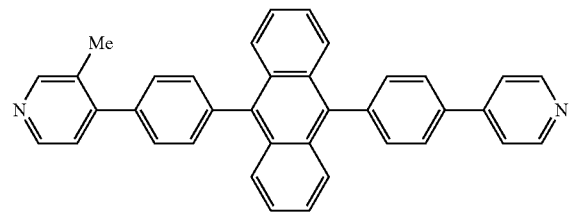
(1-147)
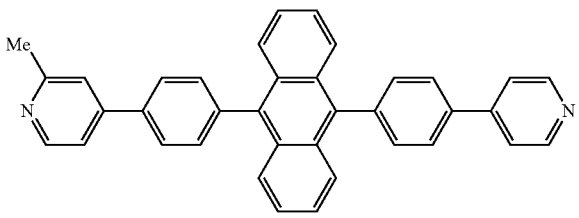
(1-148)
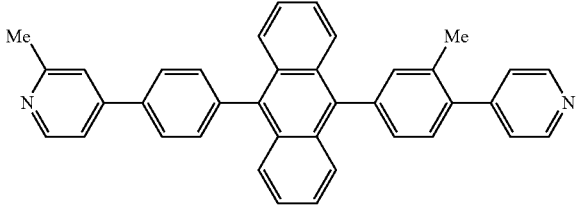
(1-149)
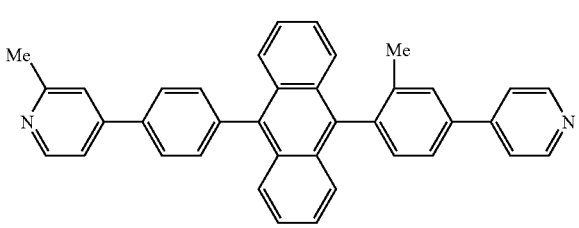
(1-150)
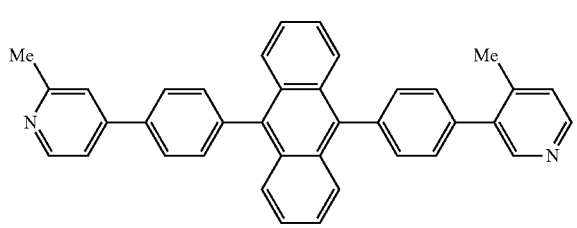

(1-151)
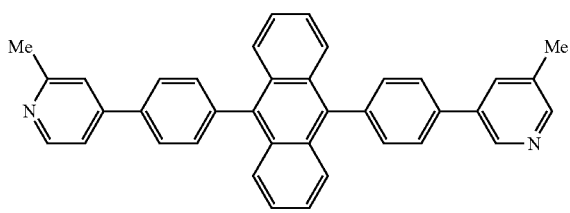
(1-152)
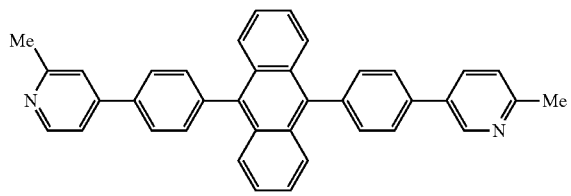
(1-153)
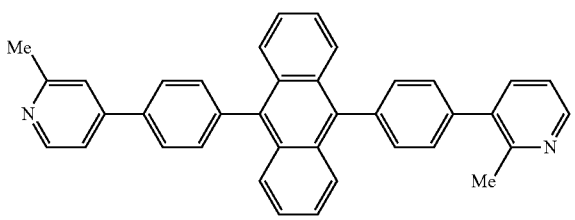
(1-154)
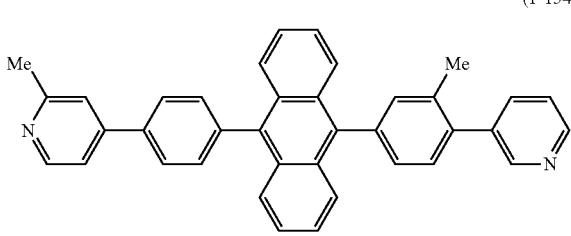
(1-155)
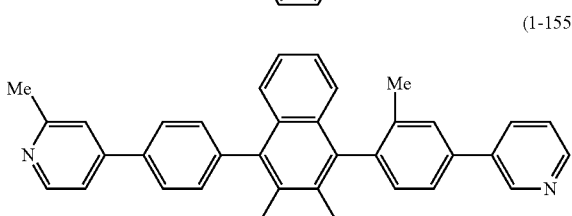
(1-156)
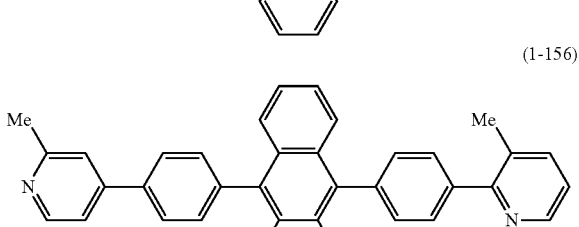
(1-157)
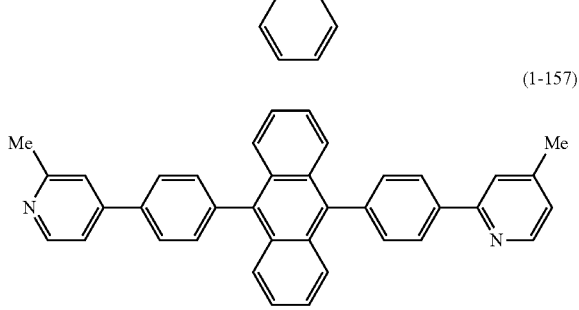
(1-158)
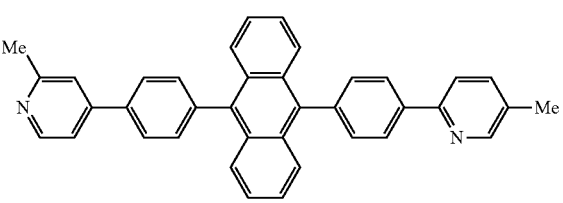
(1-159)
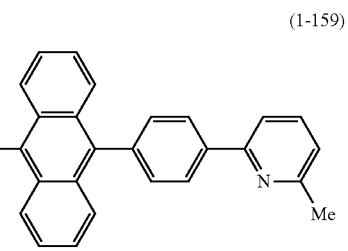
(1-160)
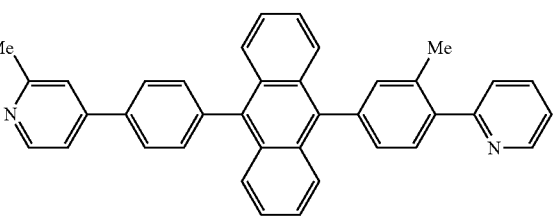
(1-161)
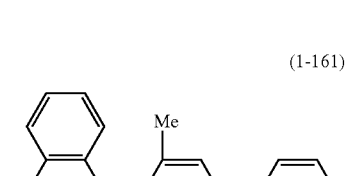
(1-162)
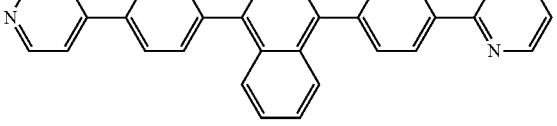
(1-163)
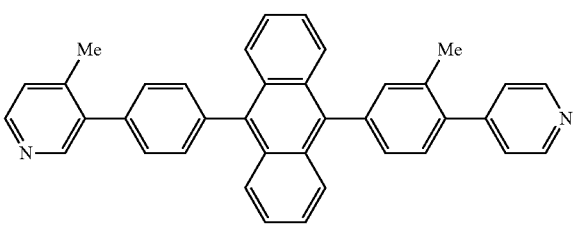

(1-164)
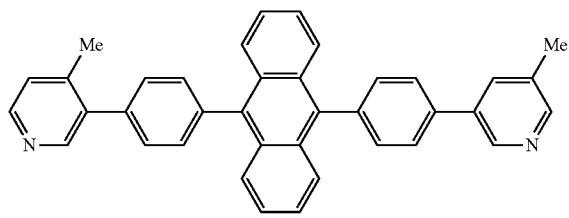
(1-170)
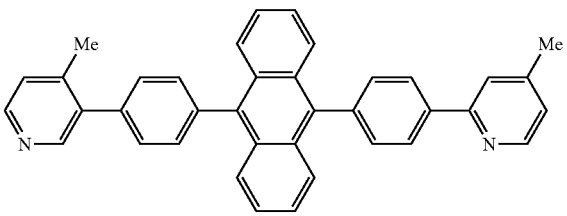
(1-165)
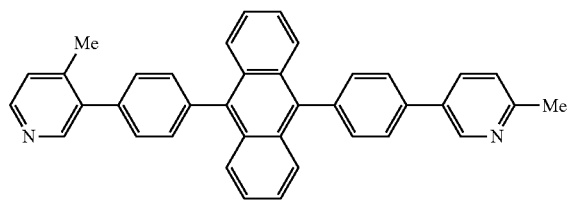
(1-171)
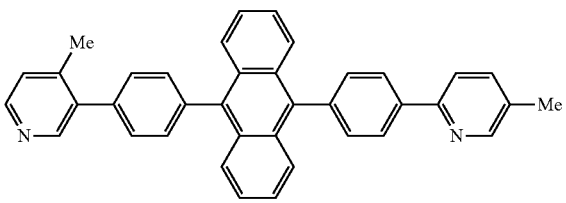
(1-166)
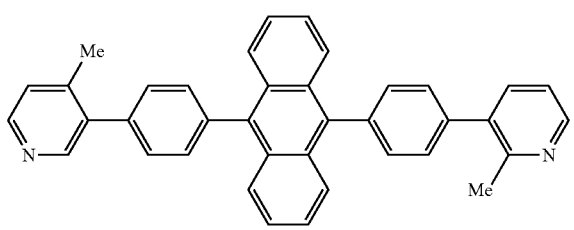
(1-172)
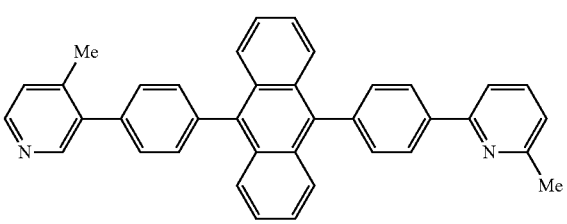
(1-167)
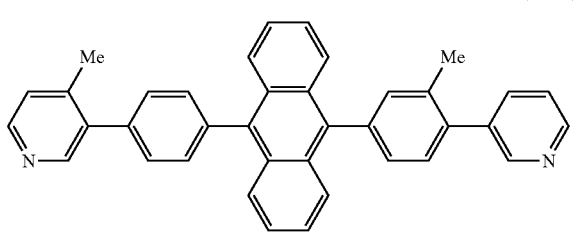
(1-173)
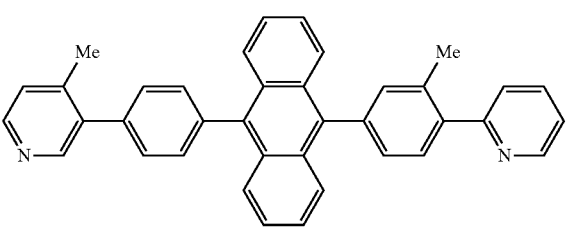
(1-168)
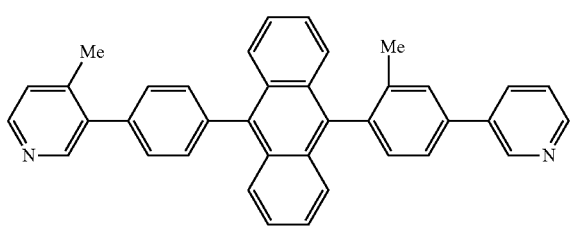
(1-174)
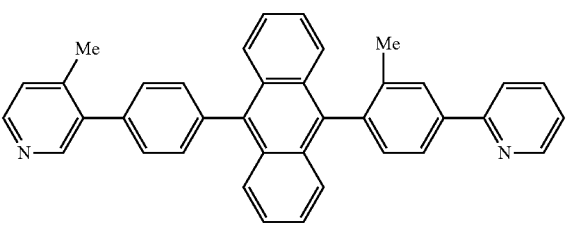
(1-169)
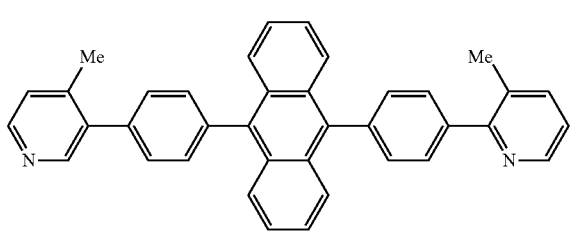
(1-175)
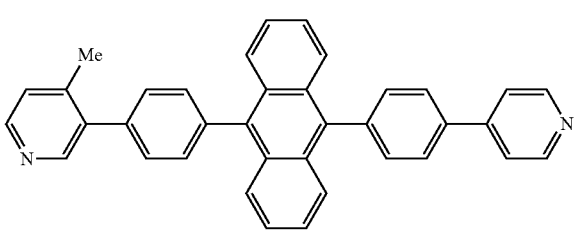

(1-176)
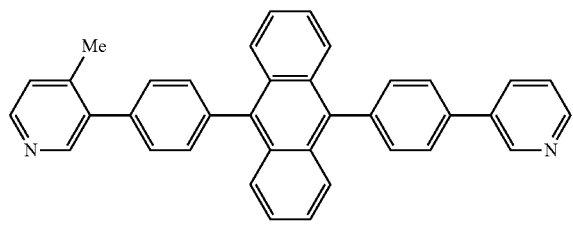
(1-182)
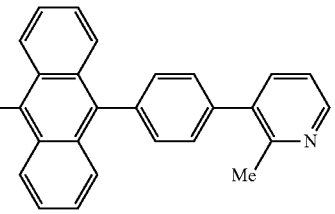
(1-177)
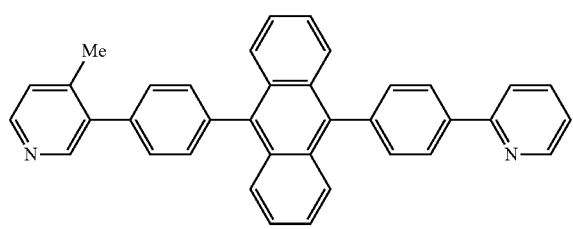
(1-183)
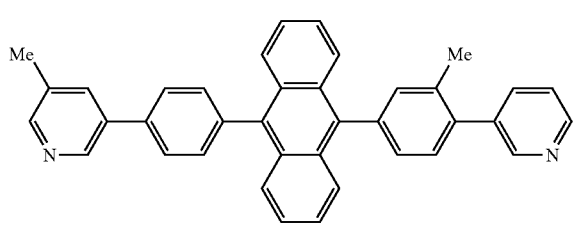
(1-178)
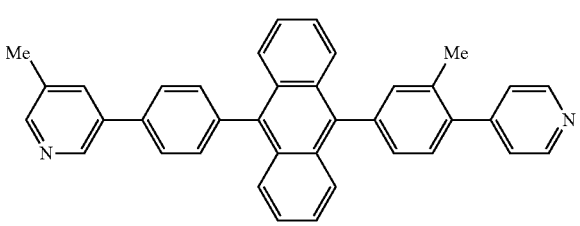
(1-184)
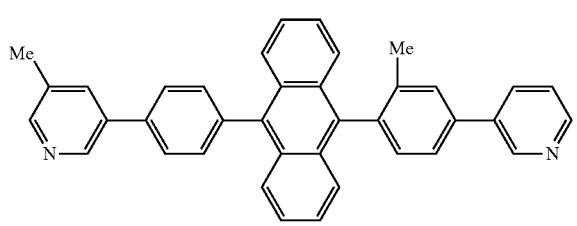
(1-179)
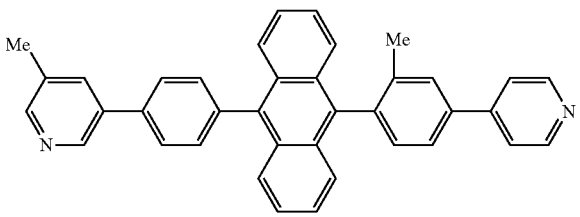
(1-185)
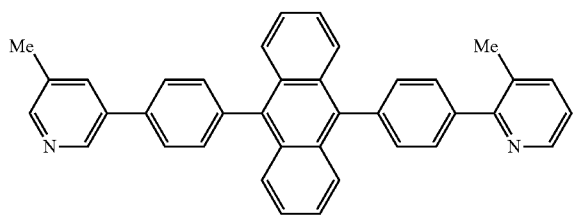
(1-180)
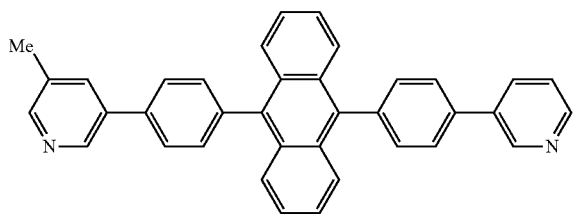
(1-186)
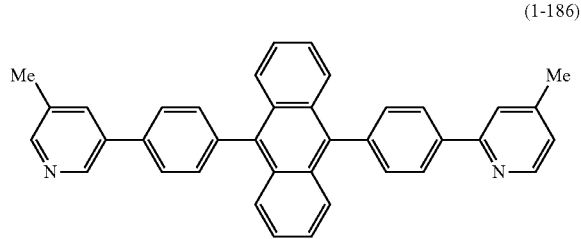
(1-181)
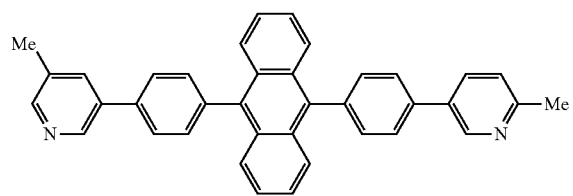
(1-187)
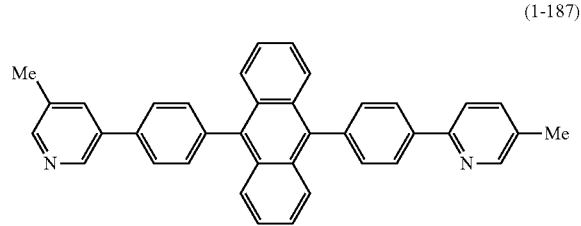

(1-188)
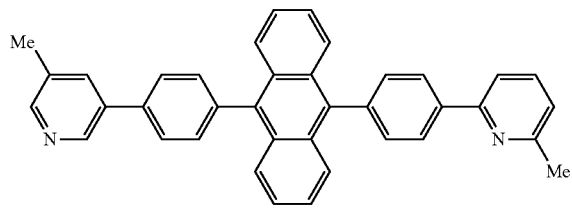
(1-189)
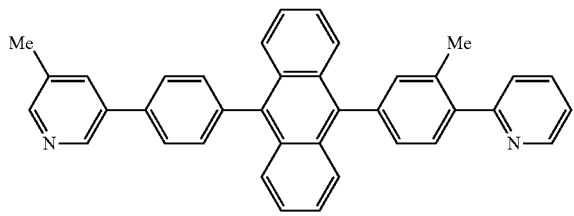
(1-190)
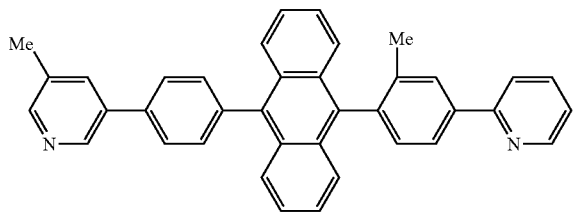
(1-191)
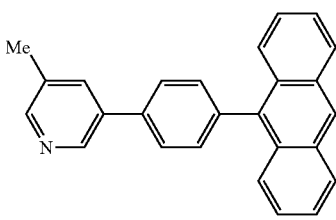
(1-192)
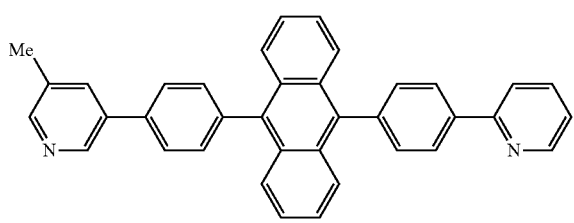
(1-193)
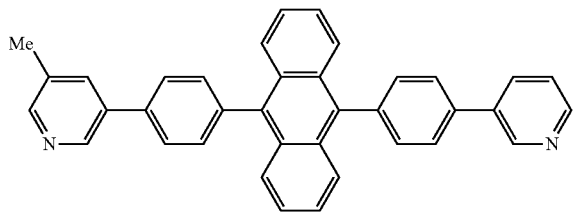
(1-194)
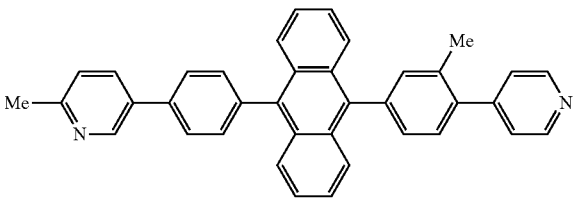
(1-195)
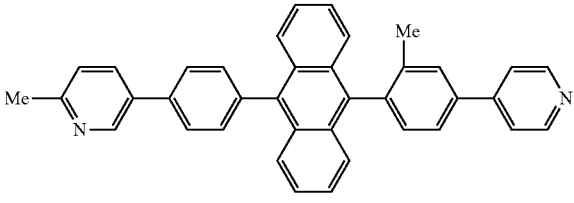
(1-196)
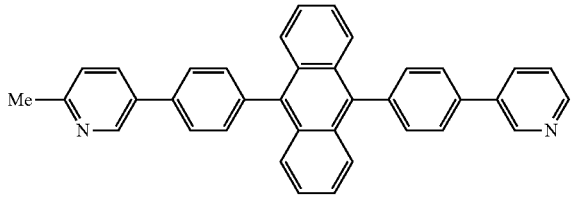
(1-197)
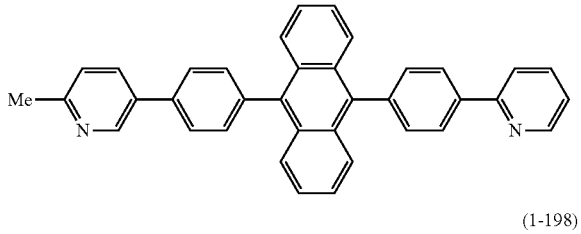
(1-198)
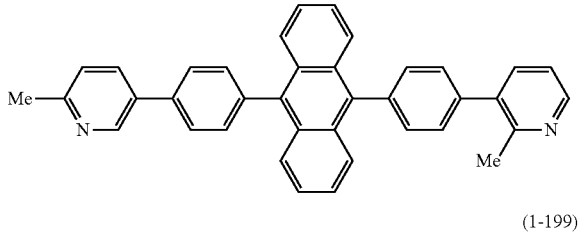
(1-199)
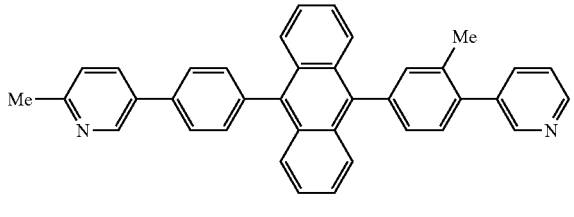
(1-200)
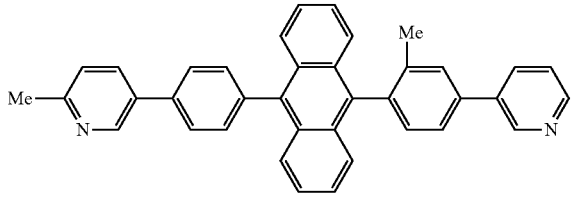

(1-201)
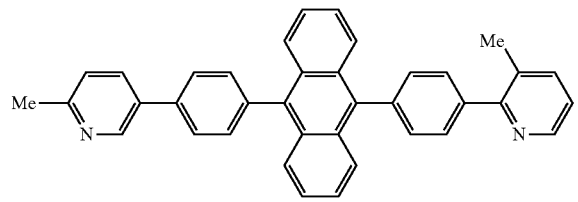
(1-202)
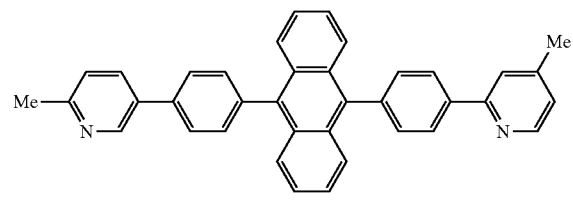
(1-203)
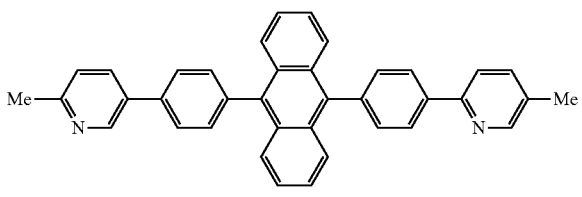
(1-204)
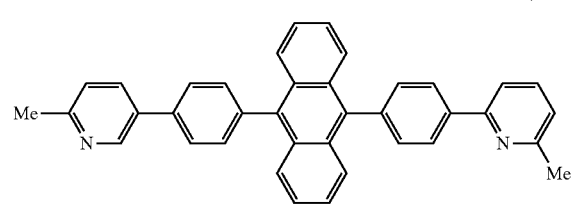
(1-205)
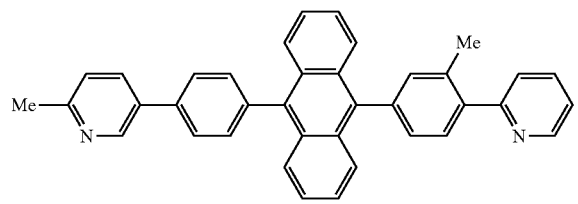
(1-206)
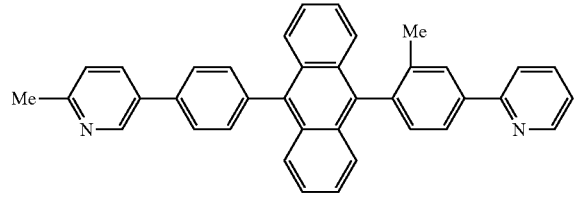
(1-207)
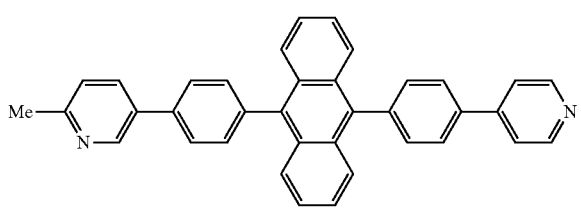
(1-208)
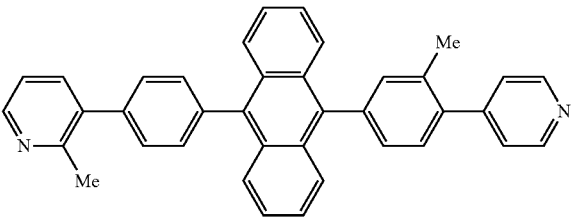
(1-209)
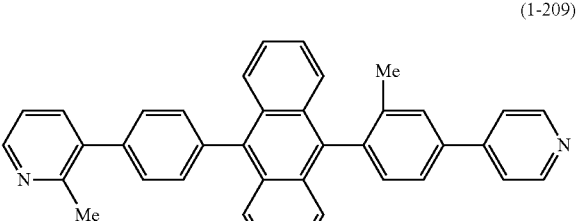
(1-210)
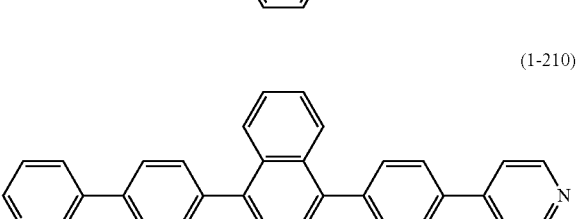
(1-211)
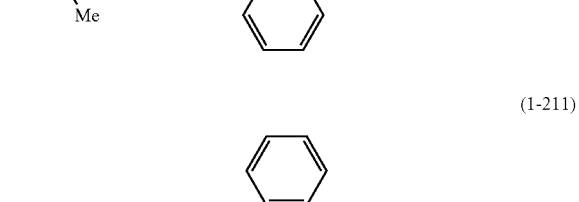
(1-212)
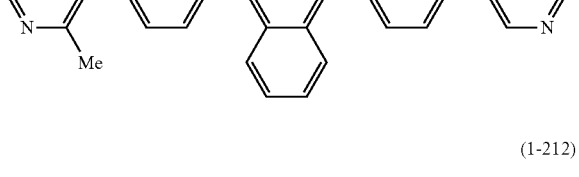
(1-213)
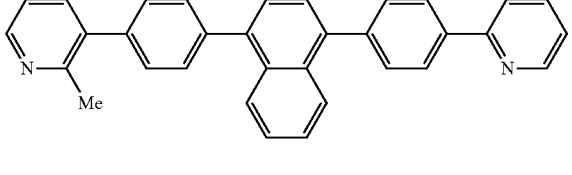
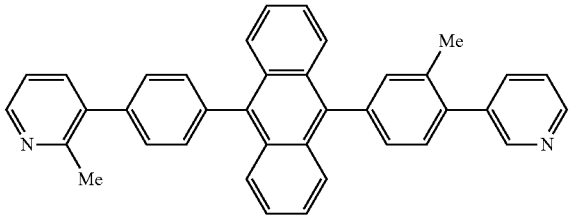

(1-214)
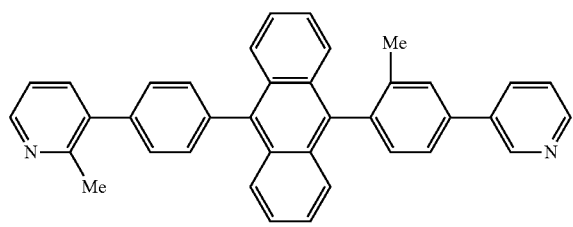
(1-215)
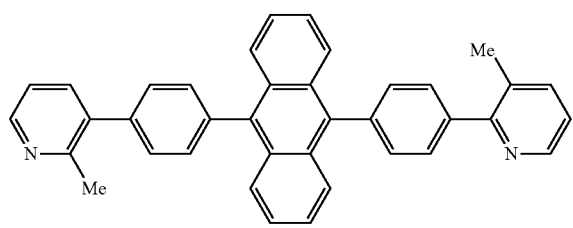
(1-216)
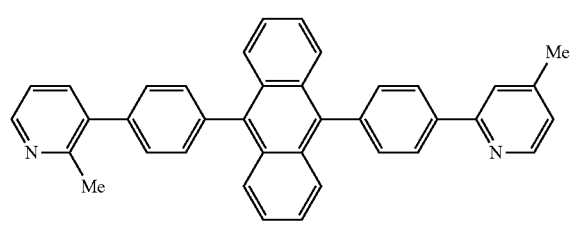
(1-217)
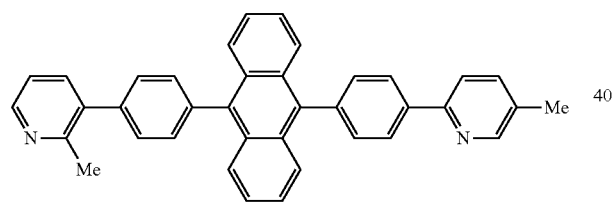
(1-218)
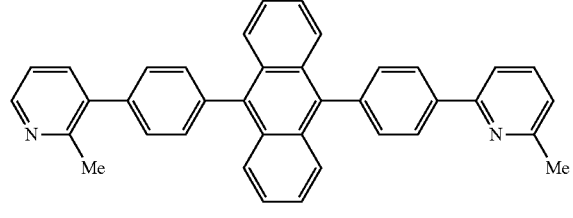
(1-219)
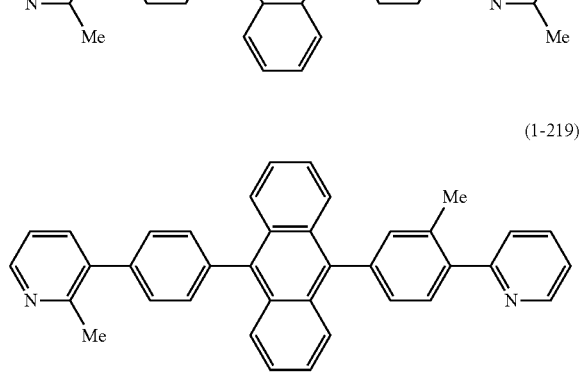
(1-220)
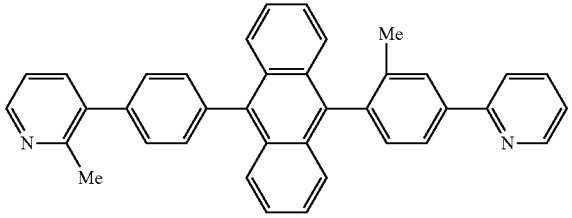
(1-221)
(1-222)
(1-223)
(1-224)

(1-225)
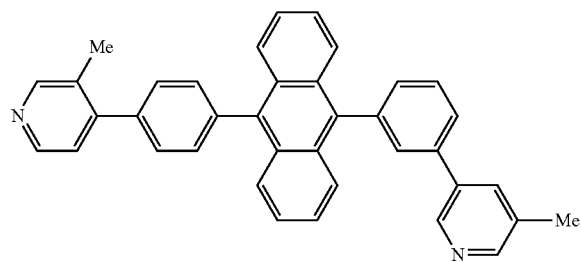
(1-226)
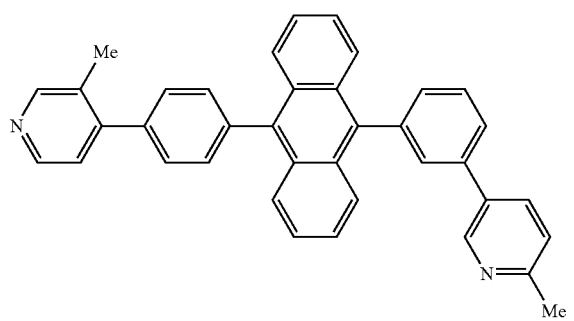
(1-227)
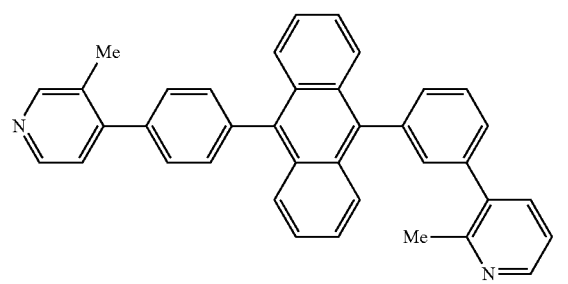
(1-228)
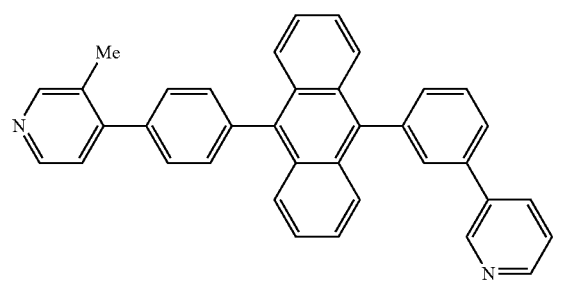
(1-229)
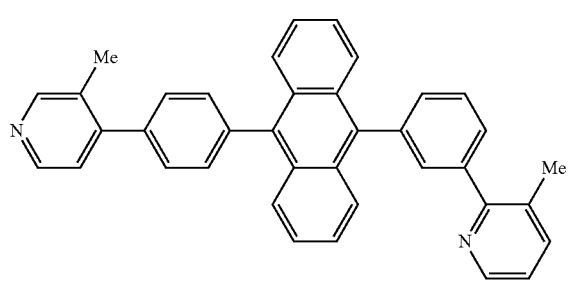
(1-230)
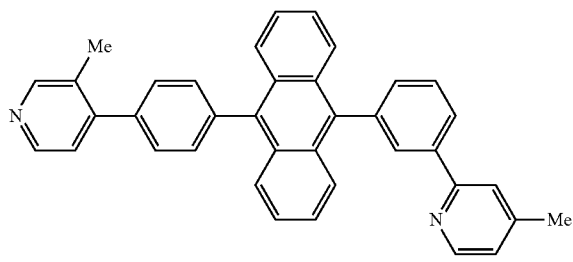
(1-231)
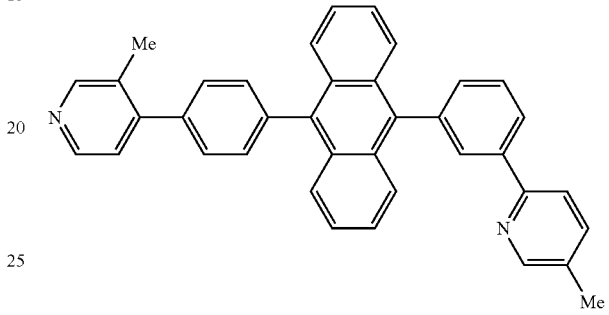
(1-232)
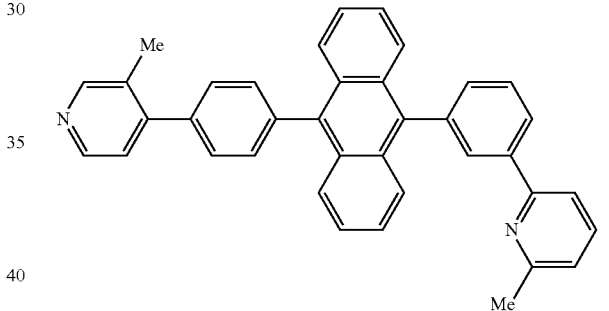
(1-233)
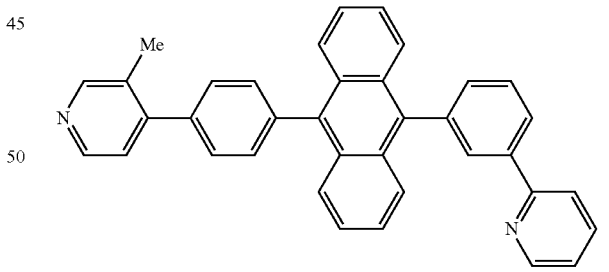
(1-234)
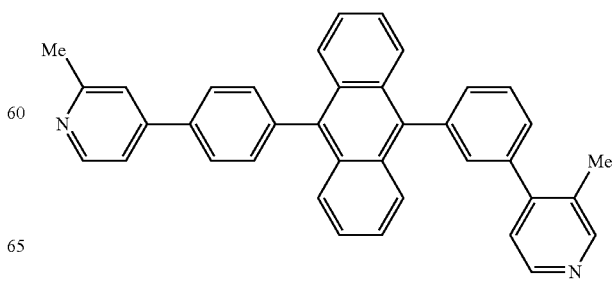

(1-235)
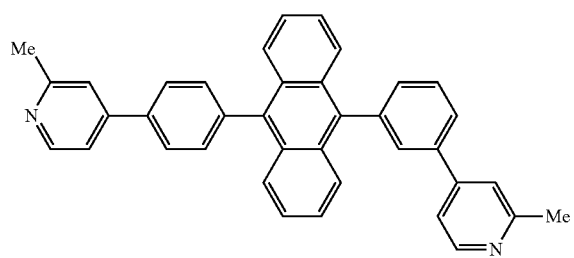
(1-236)
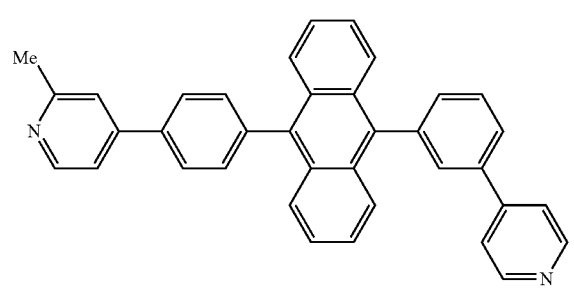
(1-237)
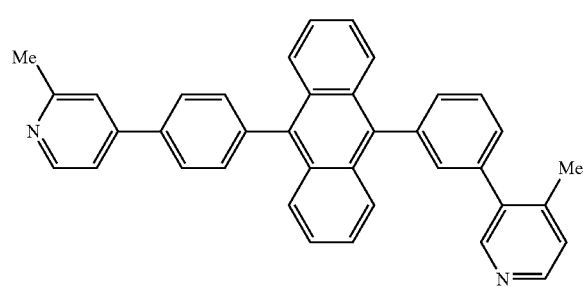
(1-238)
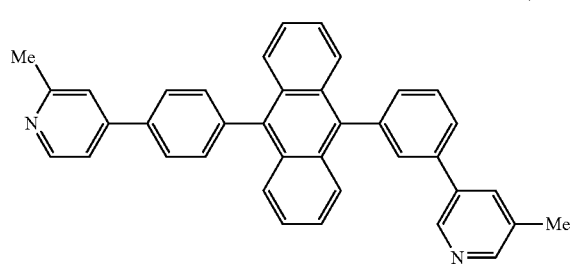
(1-239)
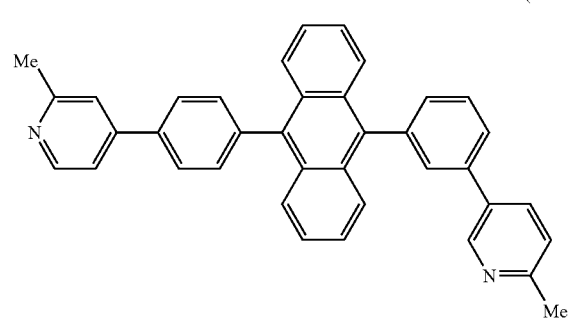
(1-240)
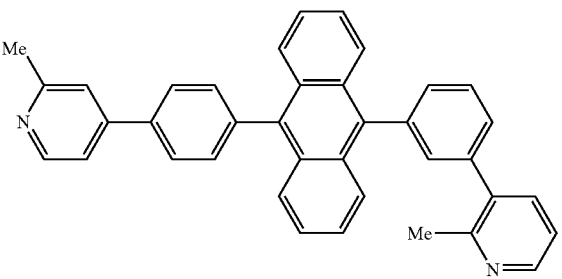
(1-241)
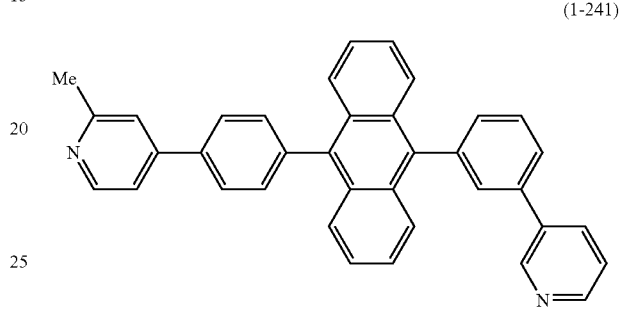
(1-242)
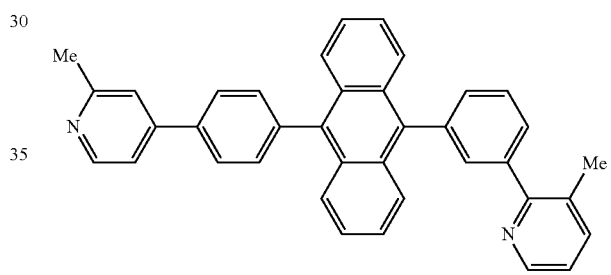
(1-243)
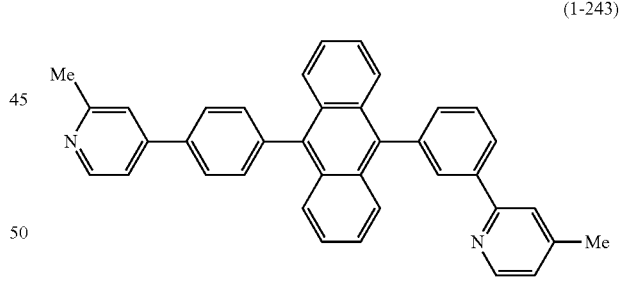
(1-244)
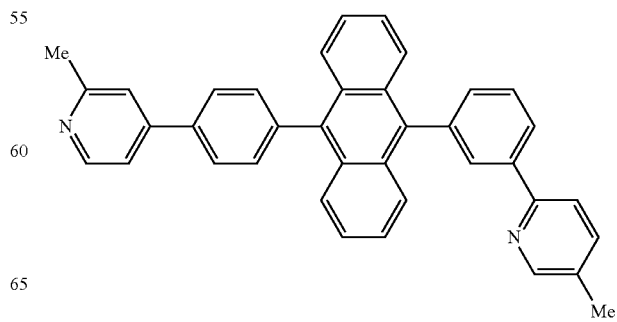

(1-245)
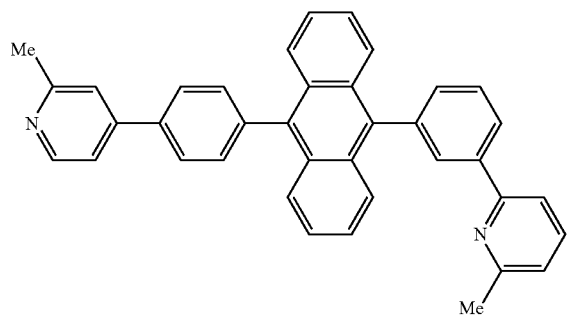
(1-246)
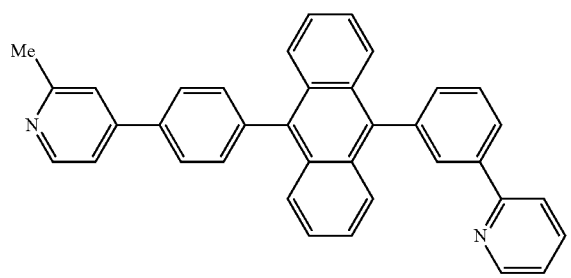
(1-247)
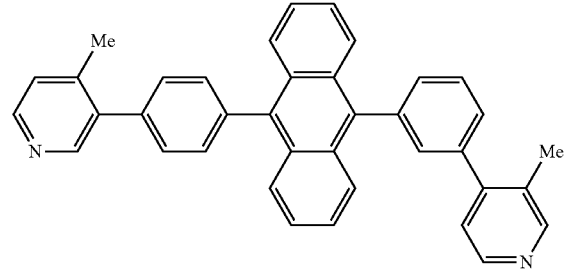
(1-248)
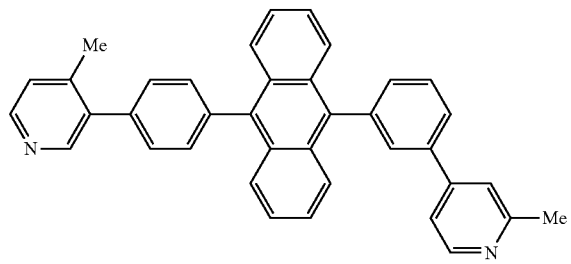
(1-249)
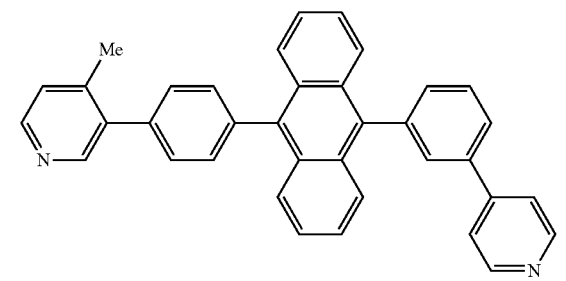
(1-250)
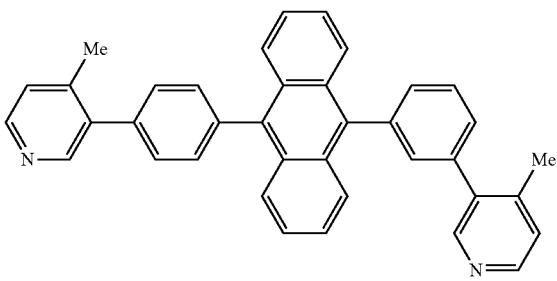
(1-251)
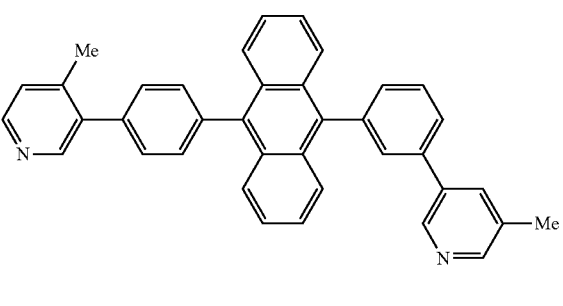
(1-252)
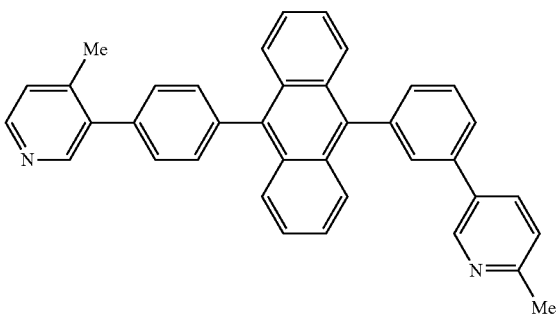
(1-253)
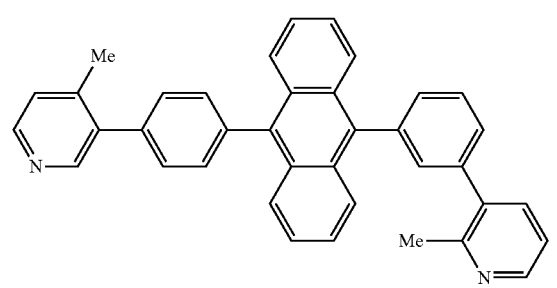
(1-254)
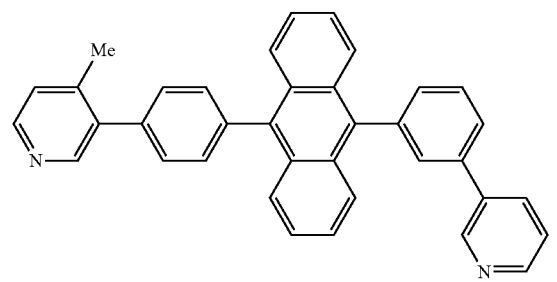

(1-255)
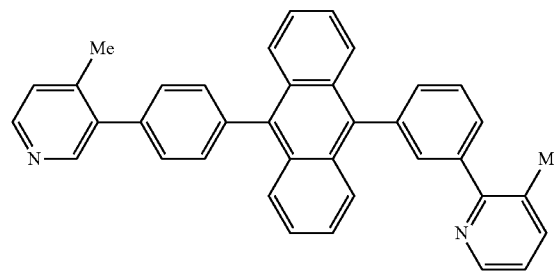
(1-256)
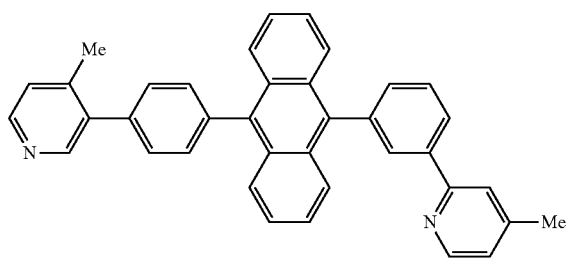
(1-257)
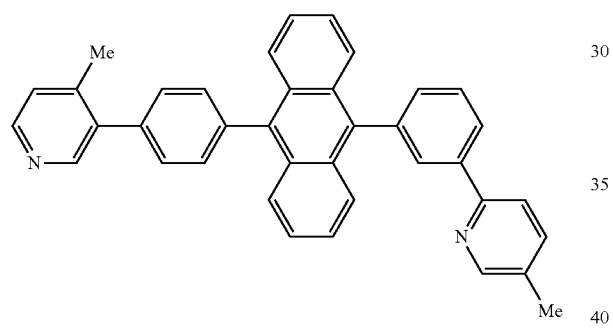
(1-258)
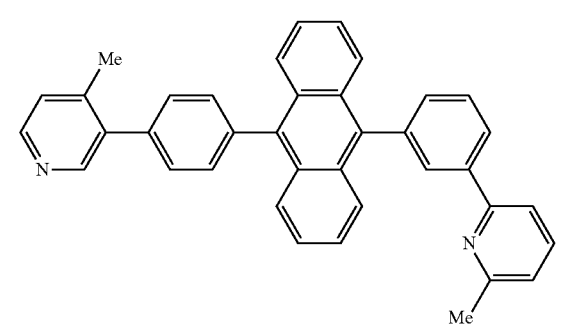
(1-259)
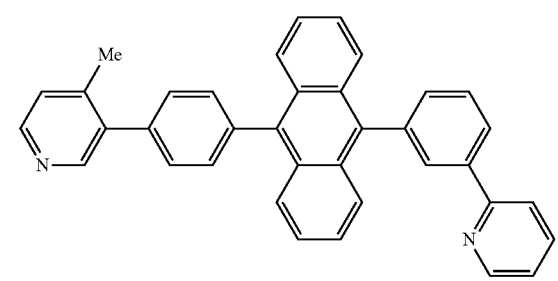
(1-260)
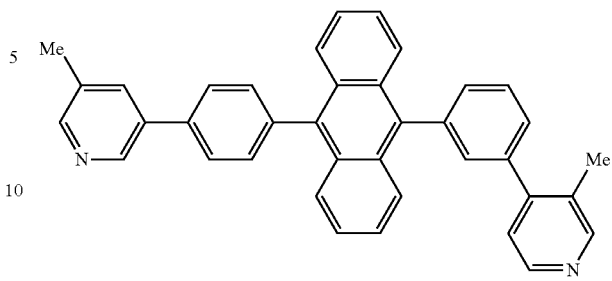
(1-261)
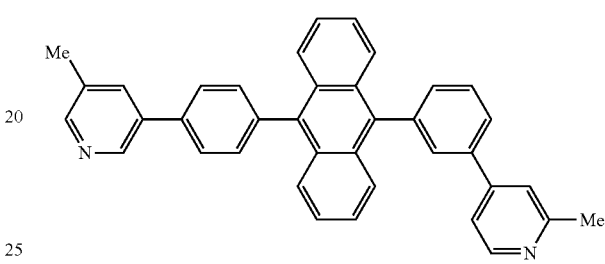
(1-262)
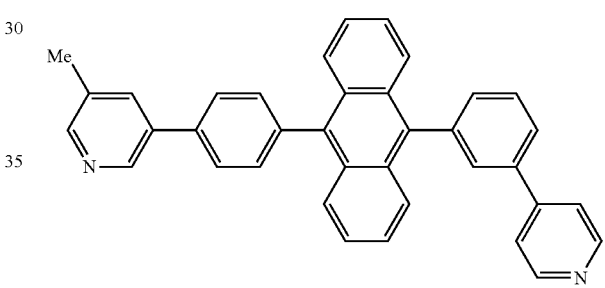
(1-263)
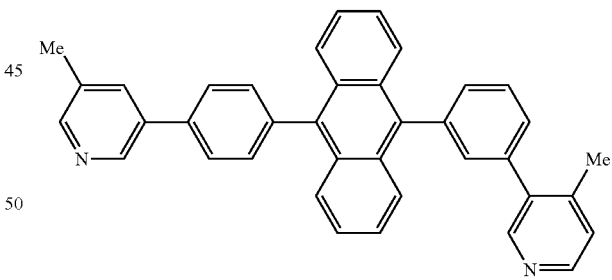
(1-264)
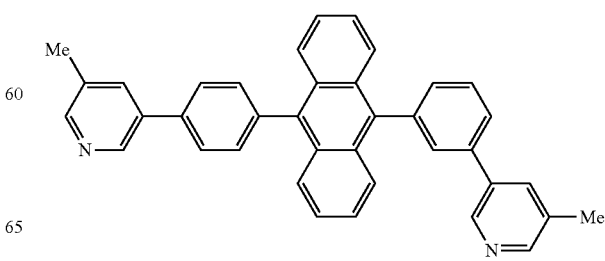

(1-265)
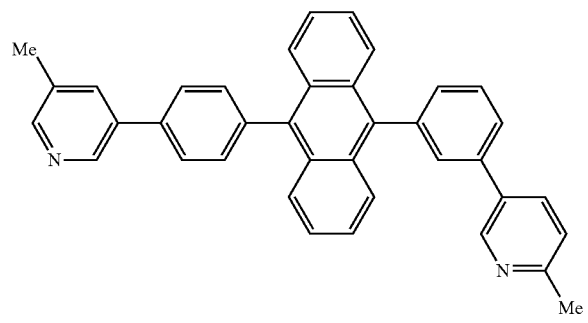
(1-266)
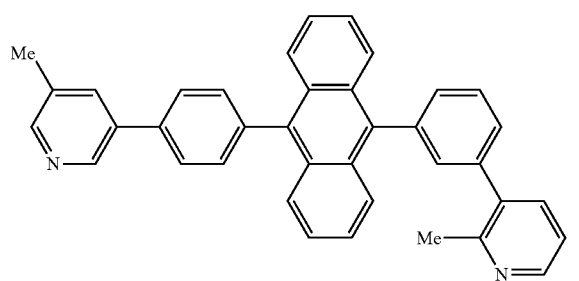
(1-267)
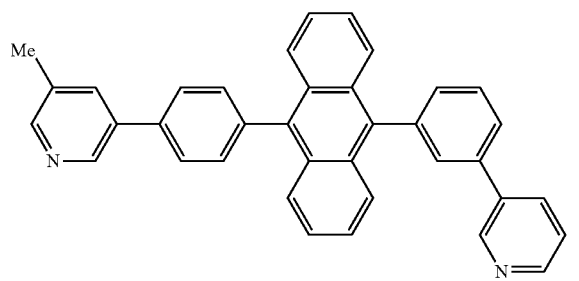
(1-268)
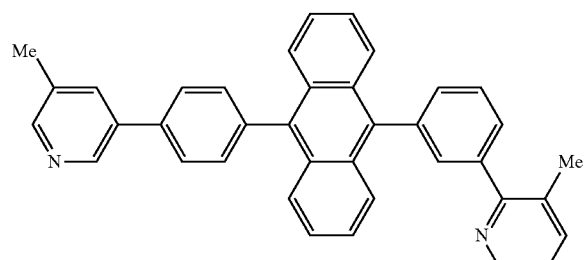
(1-269)
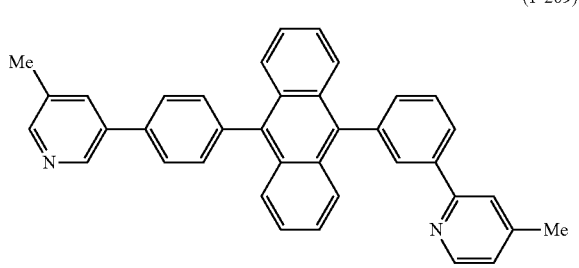
(1-270)
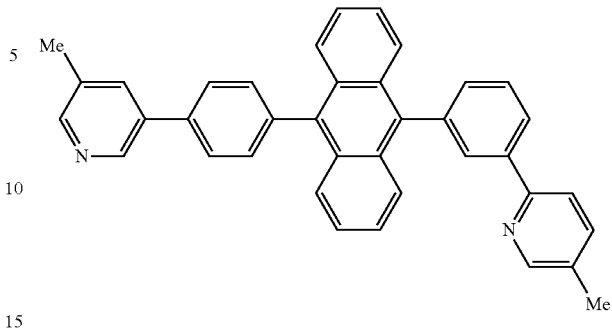
(1-271)
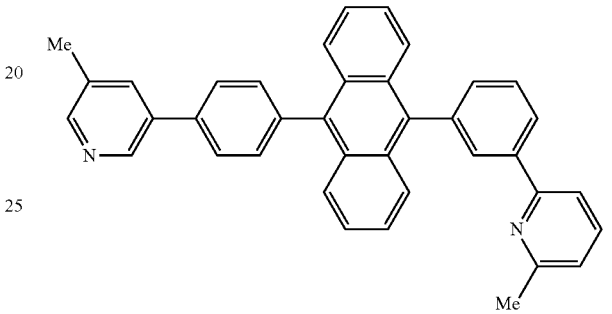
(1-272)
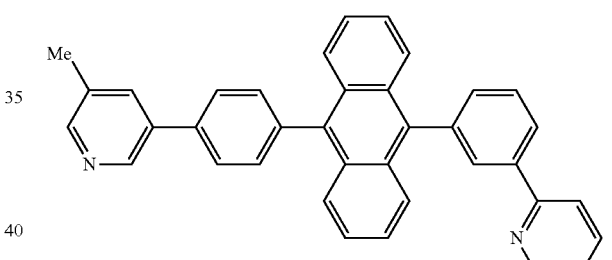
(1-273)
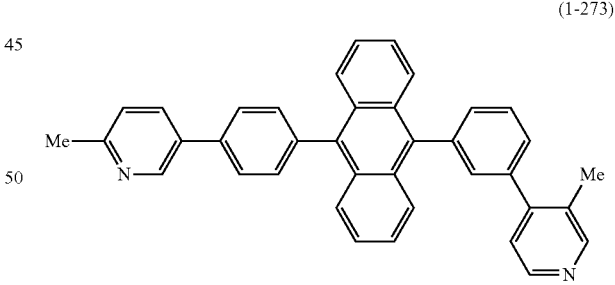
(1-274)
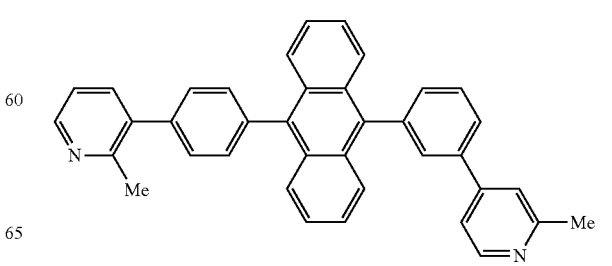

(1-275)
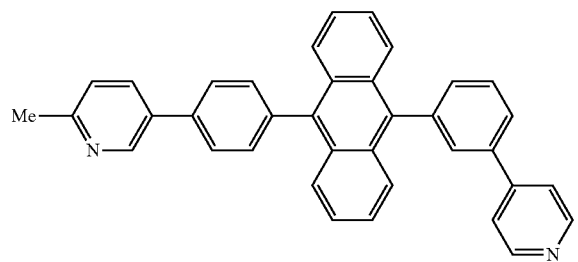
(1-276)
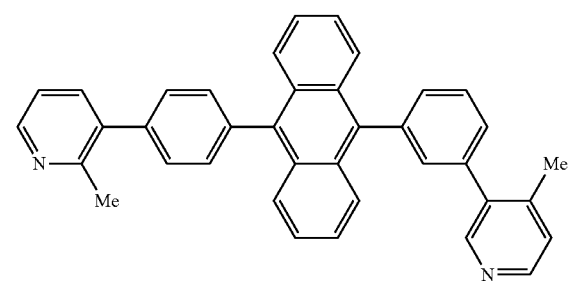
(1-277)
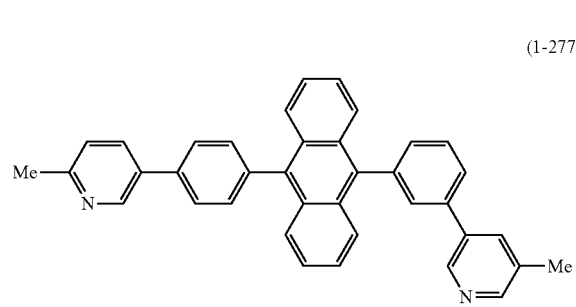
(1-278)
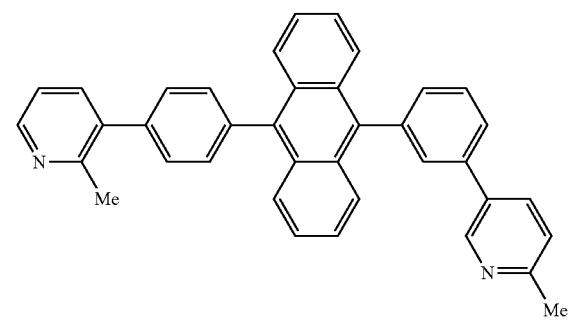
(1-279)
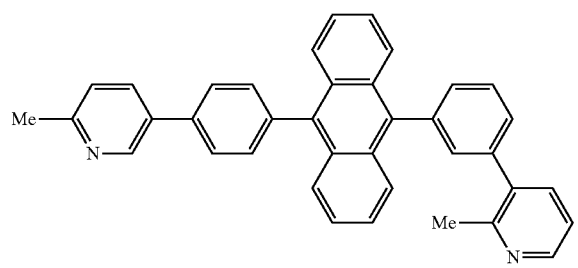
(1-280)
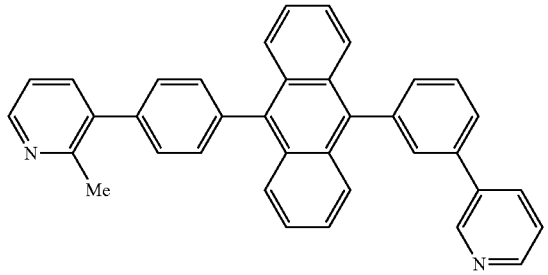
(1-281)
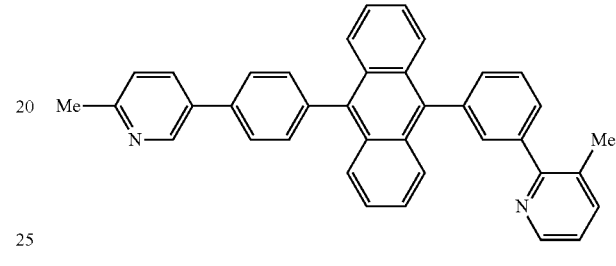
(1-282)
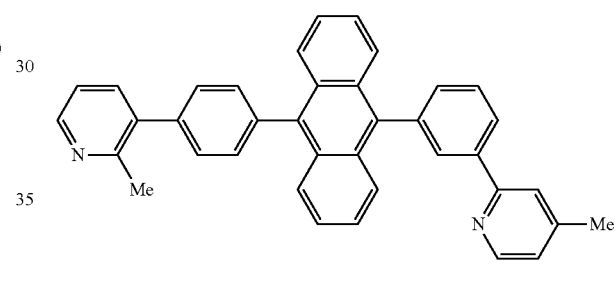
(1-283)
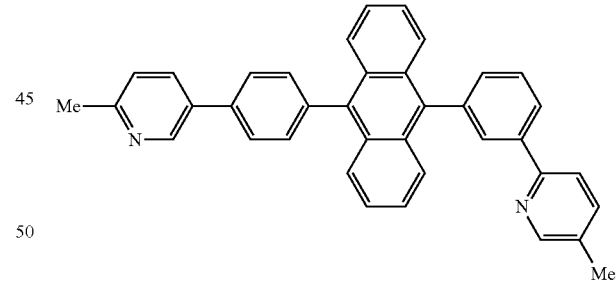
(1-284)
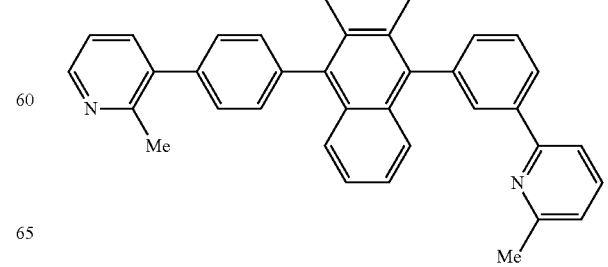

(1-285) 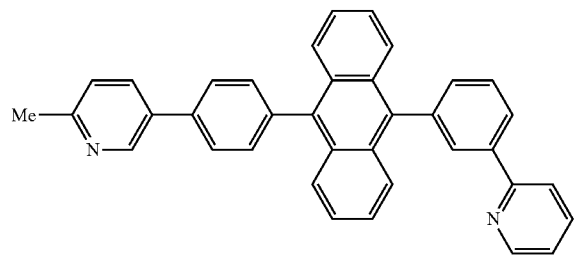
(1-291) 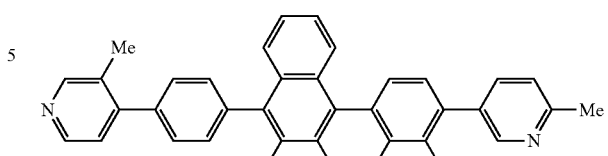
(1-286) 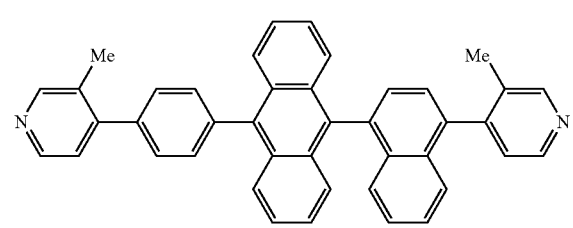
(1-292) 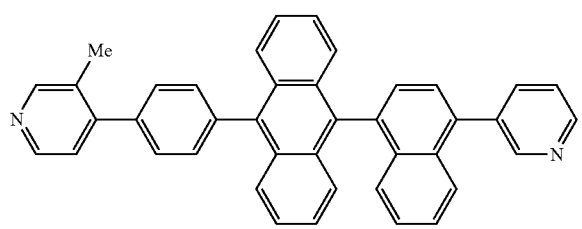
(1-287) 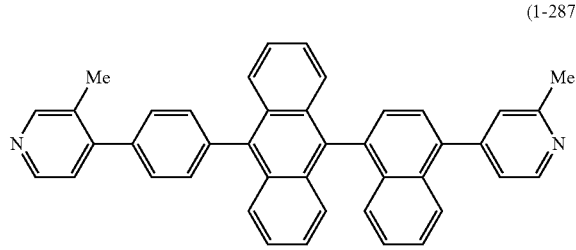
(1-293) 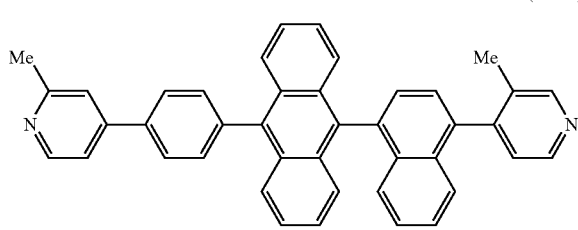
(1-288) 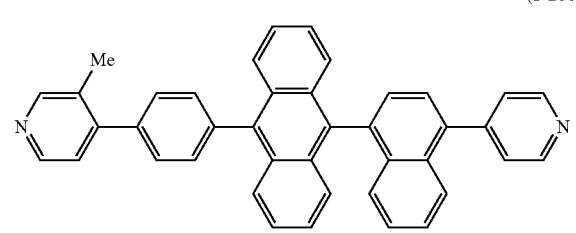
(1-294) 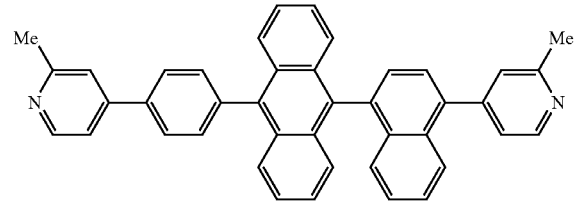
(1-289) 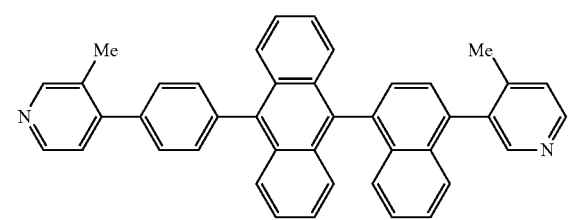
(1-295) 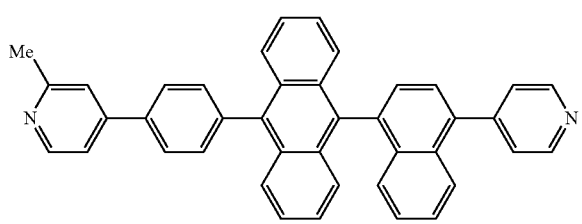
(1-290) 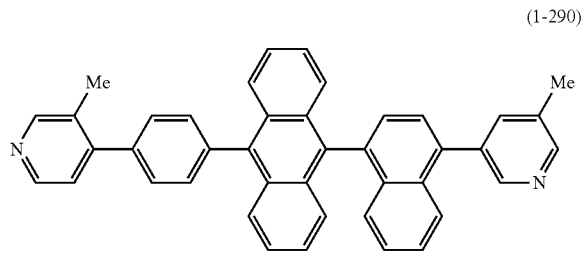
(1-296) 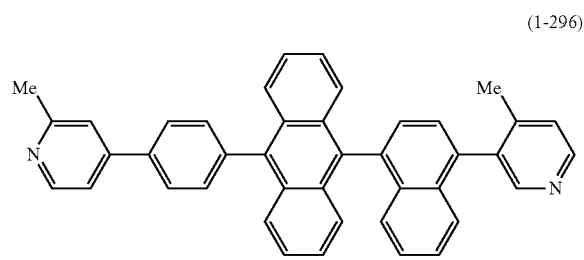

(1-297)
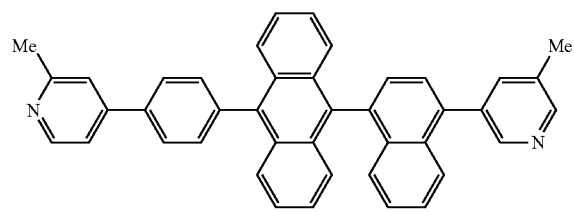
(1-298)
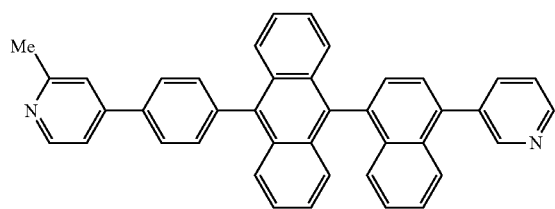
(1-299)
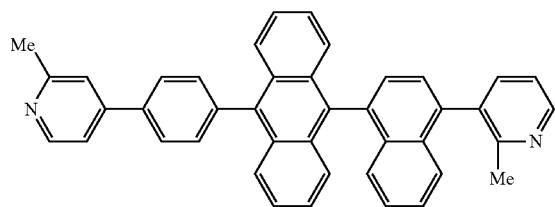
(1-300)
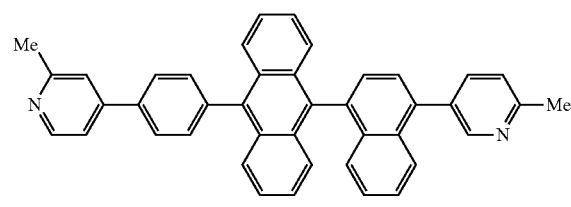
(1-301)
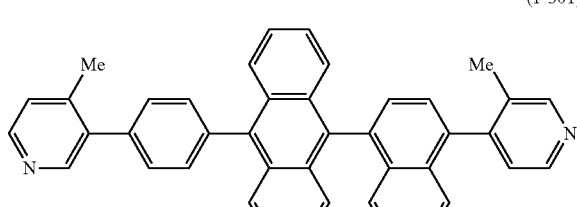
(1-302)
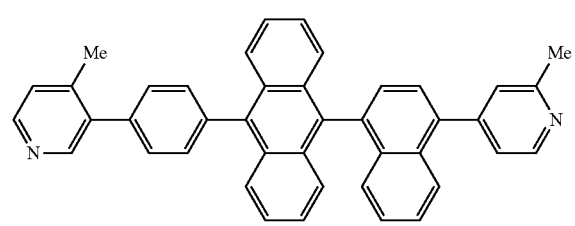
(1-303)
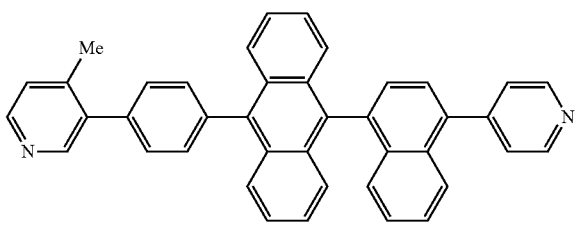
(1-304)
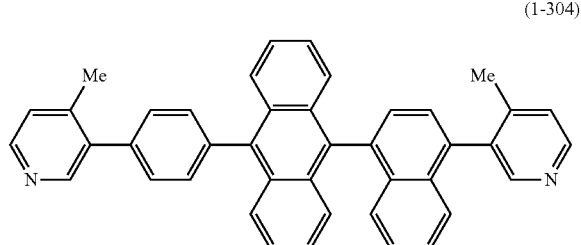
(1-305)
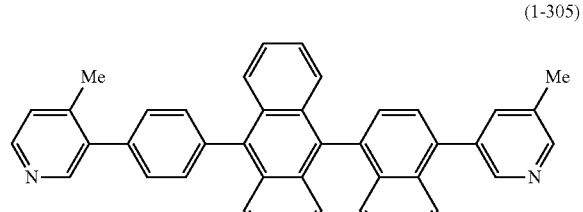
(1-306)
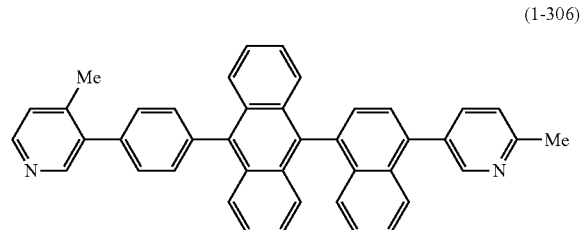
(1-307)
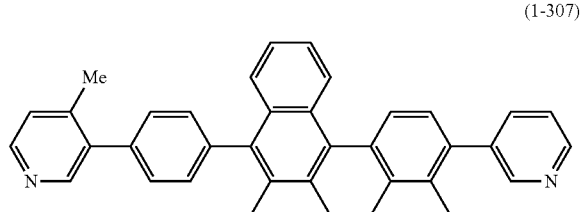
(1-308)
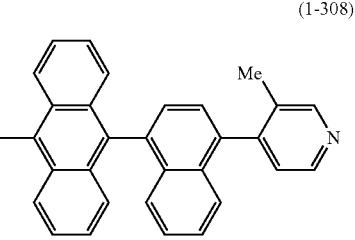

(1-309)
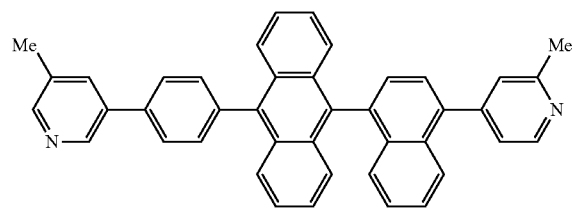
(1-315)
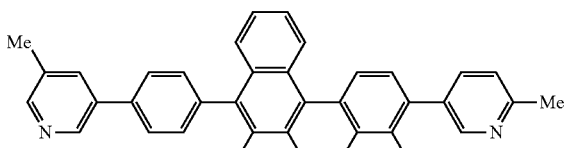
(1-310)
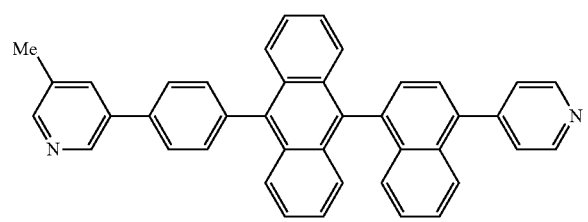
(1-316)
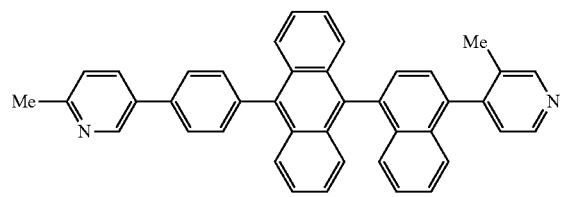
(1-311)
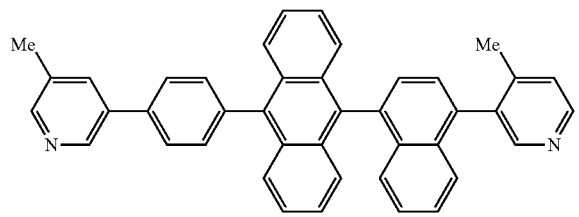
(1-317)
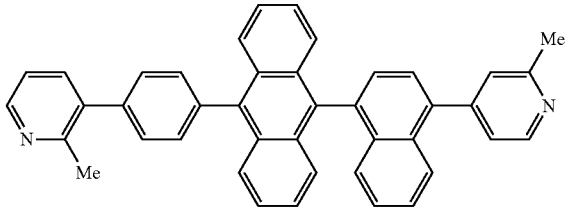
(1-312)
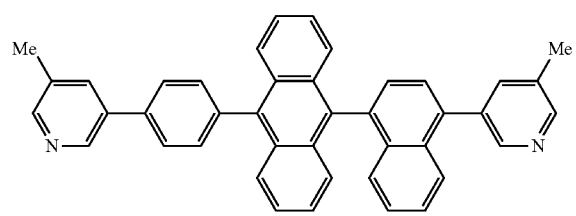
(1-318)
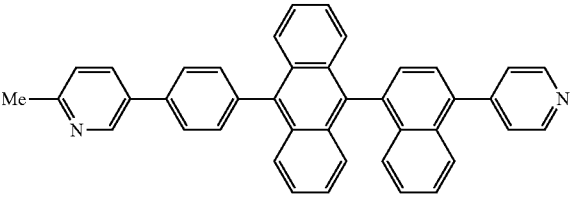
(1-313)
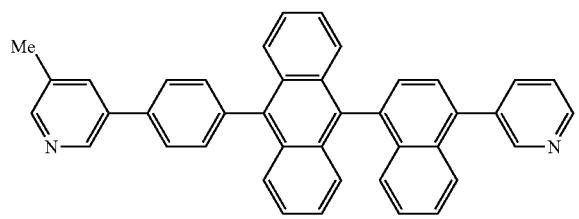
(1-319)
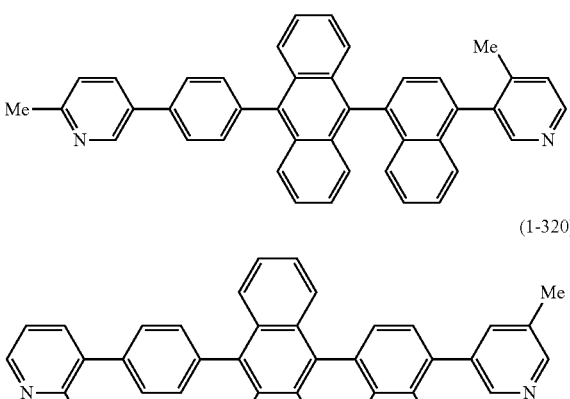
(1-314)
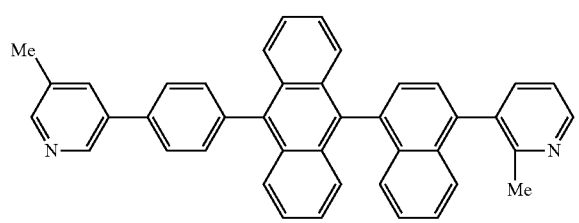
(1-320)
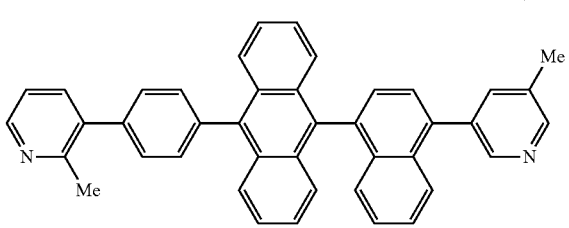
(1-321)
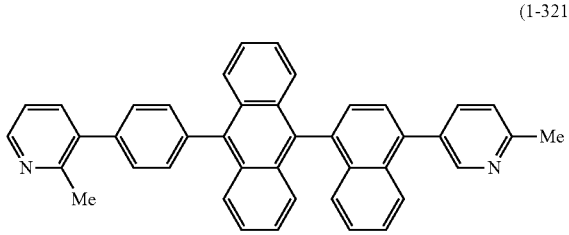

(1-322)
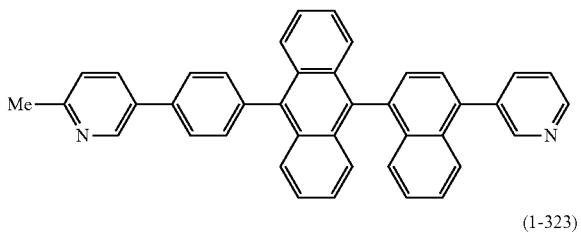

(1-329)
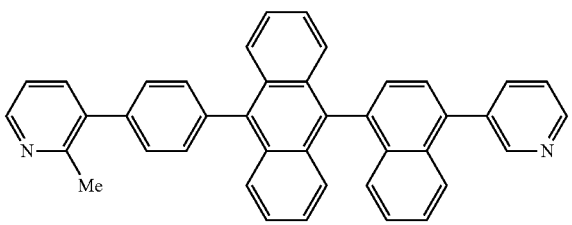

(1-323)
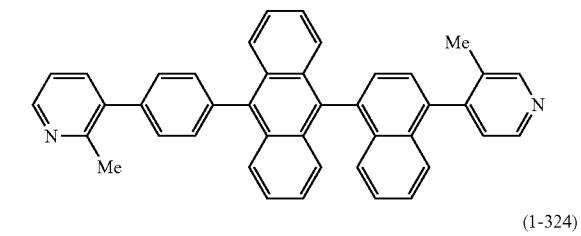

2. Process for Producing Anthracene Derivative Represented by Formula (1)

Then, a process for producing the anthracene derivative of the present invention will be explained. Fundamentally, the anthracene derivative of the present invention can be synthesized utilizing the known synthesis method, for example, the Suzuki coupling reaction or the Negishi coupling reaction (described in, for example, "Metal-Catalyzed Cross-Coupling Reactions—Second, Completely Revised and Enlarged Edition" etc.) using the known compounds. Alternatively, the anthracene derivative can be also synthesized by combining both reactions. Schemes for synthesizing the anthracene derivative represented by the formula (1) by the Suzuki coupling reaction or the Negishi coupling reaction are exemplified hereinbelow.

When the anthracene derivative of the present invention is produced, examples of a method of the production include (1) a method of synthesizing a group in which a pyridyl group and an Ar group (benzene ring or naphthalene ring) are bound, and binding this to 9,10-positions of anthracene, and (2) a method of binding an Ar group to 9,10-positions of anthracene, and binding a pyridyl group to this Ar group. Alternatively, for binding the Ar group and the pyridyl group, or binding anthracene and the Ar group in these methods, fundamentally, a coupling reaction between a halogen functional group or a trifluoromethanesulfonate functional group, and a zinc chloride complex or boronic acid (boronic acid ester) can be used.

(1) Method of Binding "Moiety Consisting of Ar and Pyridine" to 9,10-Positions of Anthracene <Synthesis of Pyridylaryl Having Reactive Substituent>

Alkyl-substituted 3-(4-bromophenyl)pyridine can be synthesized by first synthesizing a zinc chloride complex of alkyl-substituted pyridine according to the following reaction formula (1) and, then, reacting a zinc chloride complex of alkyl-substituted pyridine and p-dibromobenzene according to the following formula (2). In addition, "ZnCl$_2$.TMEDA" in the reaction formula (1) is a tetramethylethylenediamine complex of zinc chloride. In "R'Li" or "R'MgX" in the reaction formula (1), R' represents a straight or branched alkyl group, preferably a straight alkyl group having a carbon number of 1 to 4 or a branched alkyl group having a carbon number of 3 to 4, and X is a halogen.

(1-324)
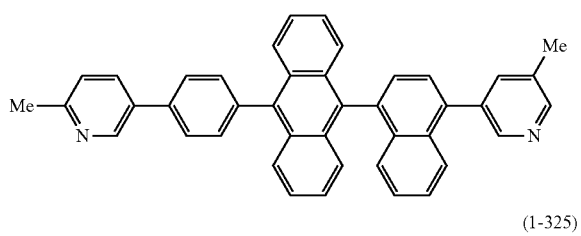

(1-325)
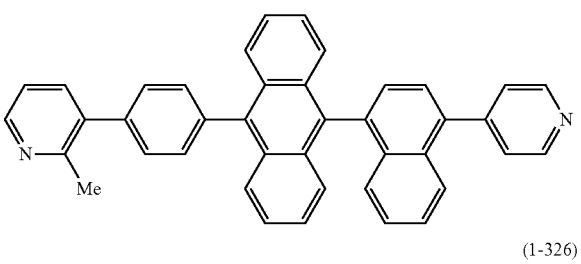

(1-326)
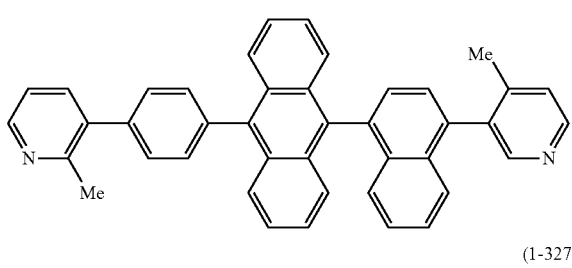

(1-327)
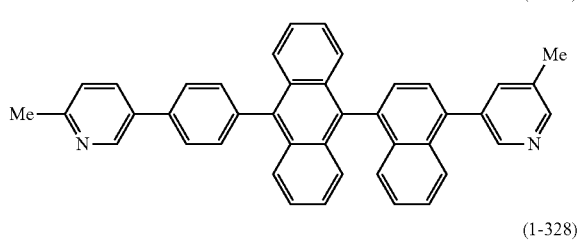

(1-328)
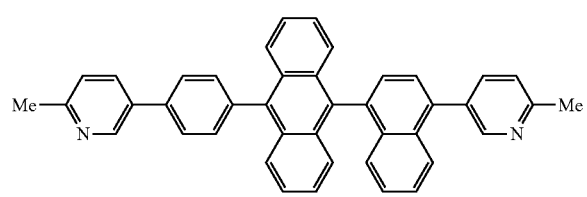

Reaction formula (1)
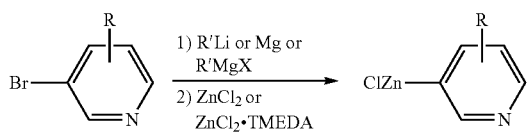

Reaction formula (2)

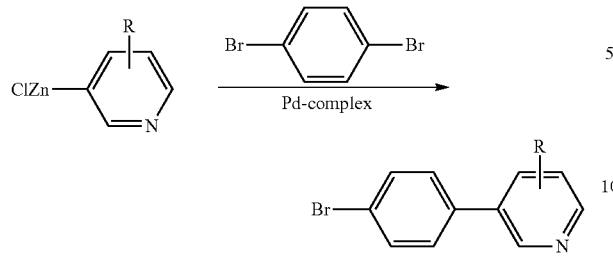

Herein, a synthesis method using 3-bromopyridine as a raw material of a pyridyl group was exemplified, but alternatively, a corresponding objective substance can be also obtained by using 2-bromopyridine or 4-bromopyridine as a raw material, or using not a bromide but an iodide as a raw material, respectively.

Herein, a synthesis method using p-dibromobenzene as a raw material of an Ar group was exemplified, but alternatively, a corresponding objective substance can be also obtained by using m-dibromobenzene, 1,4-dibromonaphthalene, 2,6-dibromonaphthalene or the like as a raw material, or further, by using not a dibromo body, but a dichloro body, a diiodo body, bis(trifluoromethanesulfonate) or a mixture thereof (e.g.: 1-bromo-4-iodobenzene etc.) as a raw material. Alternatively, an objective substance can be also obtained by reacting a benzene or naphthalene derivative such as having a halogen atom and an alkoxy group as a substituent, like bromoanisole, with a zinc chloride complex of pyridine and, thereafter, undergoing a demethylation using boron tribromide or pyridine hydrochloride and, then, trifluoromethanesulfonic acid esterification.

Furthermore, herein, a synthesis method using alkyl-substituted pyridine was exemplified, but an objective substance in which Ar is substituted with an alkyl can be also obtained by using a raw material in which not pyridine or but Ar (benzene ring or naphthalene ring) is substituted with an alkyl. In addition, an objective substance in which pyridine and Ar are substituted with an alkyl can be obtained by using alkyl-substituted Ar together with alkyl-substituted pyridine.

Alternatively, the objective substance can be also obtained by a coupling reaction of reacting p-dibromobenzene with pyridylboronic acid or pyridylboronic acid ester in place of a zinc chloride complex of pyridine.

<Method of Converting Reactive Substituent into Boronic Acid/Boronic Acid Ester>

Alkyl-substituted (4-(pyridin-3-yl)phenyl) boronic acid ester can be synthesized by lithiating alkyl-substituted 3-(4-bromophenyl)pyridine using an organolithium reagent, or converting alkyl-substituted 3-(4-bromophenyl)pyridine into a Grignard reagent using magnesium or an organomagnesium reagent, and reacting the resultant with trimethyl borate, triethyl borate or triisopropyl borate, according to the following reaction formula (3). Furthermore, alkyl-substituted (4-(pyridin-3-yl)phenyl) boronic acid can be synthesized by hydrolyzing the (4-(pyridin-3-yl)phenyl) boronic acid ester according to the following reaction formula (4). In "R'Li" and "R'MgX" in the reaction formula (3), R' represents a straight or branched alkyl group, preferably a straight alkyl group having a carbon number of 1 to 4 or a branched alkyl group having a carbon number of 3 to 4, and X is a halogen.

Reaction formula (3)

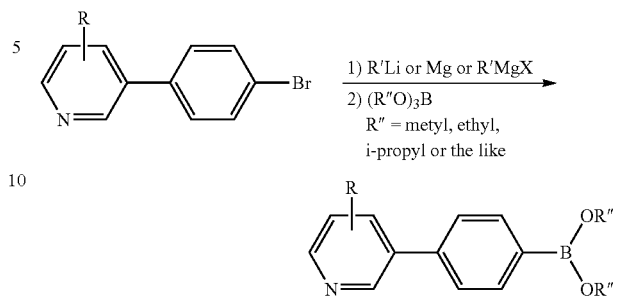

Reaction formula (4)

Other (4-(pyridin-3-yl)phenyl) boronic acid ester can be synthesized by lithiating alkyl-substituted 3-(4-bromophenyl)pyridine using an organolithium reagent, or converting alkyl-substituted 3-(4-bromophenyl)pyridine into a Grignard reagent using magnesium or an organomagnesium reagent, and reacting the resultant with bis(pinacolate)diboron or 4,4,5,5-tetramethyl-1,3,2-dioxaborolane, according to the following reaction formula (5). In addition, similar (4-(pyridin-3-yl)phenyl) boronic acid ester can be synthesized by the coupling reaction of alkyl-substituted 3-(4-bromophenyl)pyridine and bis(pinacolate)diboron or 4,4,5,5-tetramethyl-1,3,2-dioxaborolane using a palladium catalyst and a base, according to the following reaction formula (6). In "R'Li" and "R'MgX" in the reaction formula (5), R' represents a straight or branched alkyl group, preferably a straight alkyl group having a carbon number of 1 to 4 or a branched alkyl group having a carbon number of 3 to 4, and X is a halogen.

Reaction formula (5)

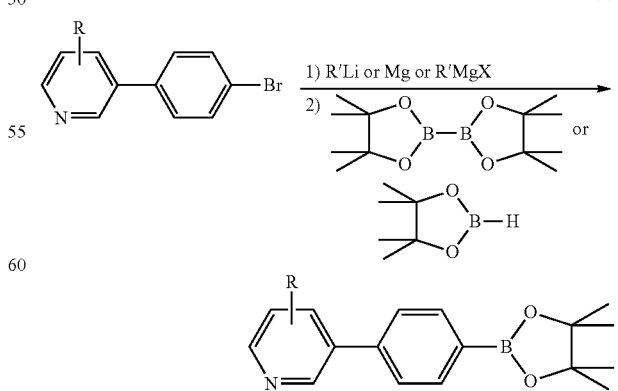

Reaction formula (6)

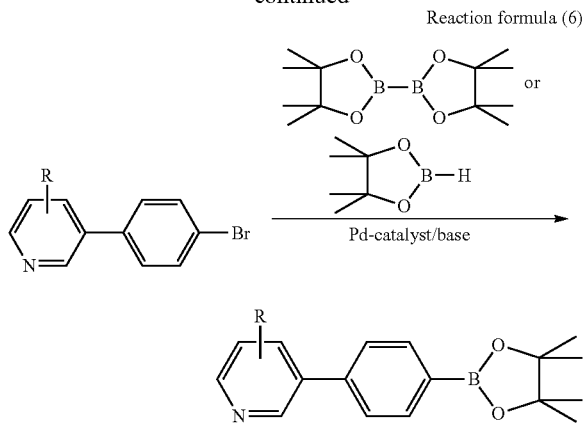

In addition, corresponding boronic acid/boronic acid ester can be also synthesized by using other regioisomer in place of 3-(4-bromophenyl)pyridine in the above reaction formula (3), (5) or (6). Furthermore, the objective substance can be synthesized likewise by using a chloride, an iodide or trifluoromethanesulfonate in place of a bromide such as 3-(4-bromophenyl)pyridine.

Synthesis of Central Skeleton Anthracene Having Reactive Substituent 9,10-Dibromoanthracene 9,10-Dibromoanthracene is obtained by brominating anthracene using an appropriate brominating agent, as shown in the following reaction formula (7). Examples of the appropriate brominating agent include bromine, and N-brominated succinic acid imide (NBS).

Reaction formula (7)

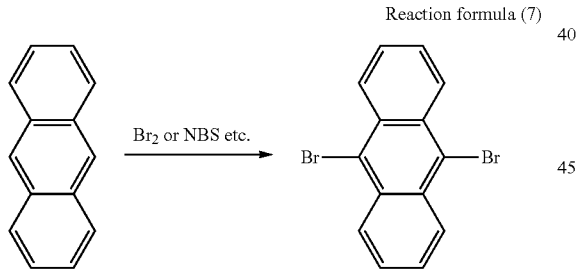

In addition, when an anthracene derivative having a substituent (alkyl, cycloalkyl, aryl etc.) at a 2-position is desired, the anthracene derivative having a substituent at a 2-position can be synthesized by Suzuki coupling between anthracene in which a 2-position is substituted with a halogen or triflate, and boronic acid (or boronic acid ester) of a group corresponding to the substituent. Alternatively, examples of other method include a synthesis method by Negishi coupling between anthracene in which a 2-position is substituted with a halogen or triflate, and a zinc complex of a group corresponding to the substituent. Further examples include a synthesis method by Suzuki coupling between 2-anthraceneboronic acid (or boronic acid ester) and a group corresponding to the substituent, which is substituted with a halogen or triflate and, further, a synthesis method by Negishi coupling between a 2-anthracene zinc complex and a group corresponding to the substituent, which is substituted with a halogen or triflate. In addition, an anthracene derivative having a substituent at a position other than a 2-position can be synthesized likewise by using a raw material in which a position at which anthracene is substituted with a halogen, triflate, boronic acid (or boronic acid ester) or a zinc complex is a desired position.

9,10-Dianthracene Zinc Complex

A 9,10-dianthracene zinc complex can be synthesized by lithiating 9,10-dibromoanthracene using an organolithium reagent, or converting 9,10-dibromoanthracene into a Grignard reagent using magnesium or an organomagnesium reagent, and reacting the resultant with zinc chloride or a zinc chloride tetramethylethylenediamine complex ($ZnC_2 \cdot TMEDA$), as shown in the following reaction formula (8). In the reaction formula (8), R' represents a straight or branched alkyl group, preferably a straight alkyl group having a carbon number of 1 to 4 or a branched alkyl group having a carbon number of 3 to 4. In addition, the complex can be also synthesized likewise using a chloride or an iodide in place of a bromide such as 9,10-dibromoanthracene Reaction formula (8)

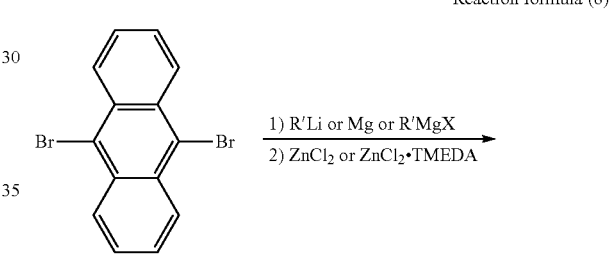

9,10-Anthracenediboronic Acid (or Boronic Acid Ester)

A 9,10-anthracenediboronic acid ester can be synthesized by lithiating 9,10-dibromoanthracene using an organolithium reagent or converting 9,10-dibromoanthracene into a Grignard reagent using magnesium or an organomagnesium reagent, and reacting the resultant with trimethyl borate, triethyl borate or triisopropyl borate, as shown in the following reaction formula (9). Furthermore, 9,10-anthracenediboronic acid can be synthesized by hydrolyzing the 9,10-anthracenediboronic acid ester according to the following reaction formula (10). In the reaction formula (9), R' represents a straight or branched alkyl group, preferably a straight alkyl group having a carbon number of 1 to 4 or a branched alkyl group having a carbon number of 3 to 4.

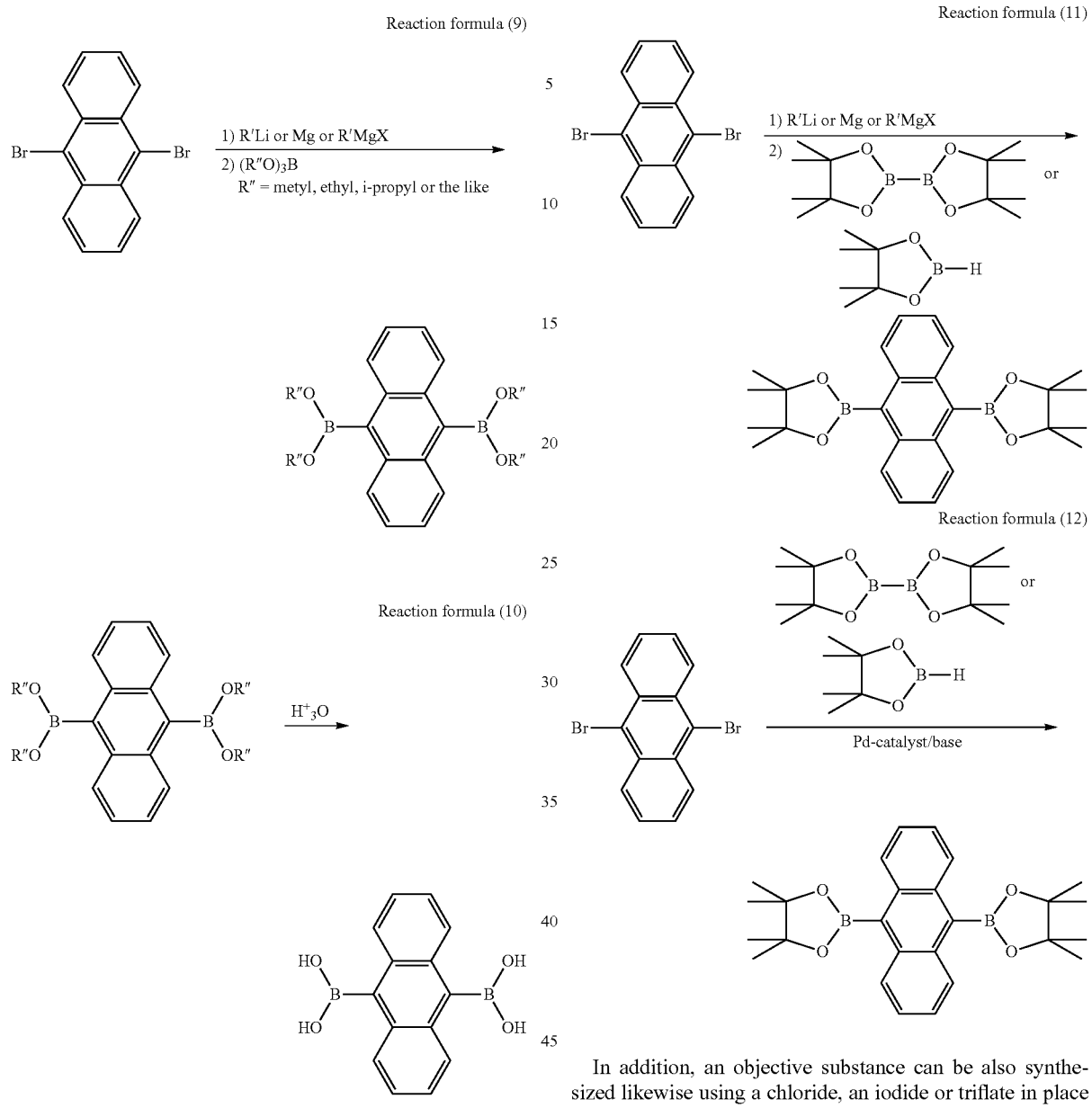

In addition, other 9,10-anthracenediboronic acid ester can be synthesized by lithiating 9,10-dibromoanthracene using an organolithium reagent, or converting 9,10-dibromoanthracene into a Grignard reagent using magnesium or an organomagnesium reagent, and reacting the resultant with bis(pinacolate)diboron or 4,4,5,5-tetramethyl-1,3,2-dioxaborolane, as shown in the following reaction formula (11). As shown in the following reaction formula (12), similar 9,10-anthracenediboronic acid ester can be synthesized by the coupling reaction of 9,10-dibromoanthracene and bis (pinacolate)diboron or 4,4,5,5-tetramethyl-1,3,2-dioxaborolane using a palladium catalyst and a base. In the reaction formula (11), R' represents a straight or branched alkyl group, preferably a straight alkyl group having a carbon number of 1 to 4 or a branched alkyl group having a carbon number of 3 to 4.

In addition, an objective substance can be also synthesized likewise using a chloride, an iodide or triflate in place of a bromide such as 9,10-dibromoanthracene in the above reaction formula (9), (11) or (12).

<Method of Binding Anthracene Having Reactive Substituent and "Moiety Consisting of Ar and Pyridine">

Since regarding the "moiety consisting of Ar and pyridine", a bromo body of pyridylphenyl (reaction formulas (1) to (2)), or boronic acid and boronic acid ester (reaction formulas (3) to (6)) can be synthesized, and regarding anthracene having a reactive substituent, a bromo body of anthracene (reaction formula (7)), a zinc chloride complex (reaction formula (8)), or boronic acid and boronic acid ester (reaction formulas (9) to (12)) can be synthesized, the anthracene derivative of the present invention can be synthesized by binding the "moiety consisting of Ar and pyridine" and anthracene, by reference to the coupling reactions which were used in the foregoing explanation.

In this final coupling reaction, in order to make two "moieties consisting of Ar and pyridine" of the anthracene derivative represented by the formula (1) have different structures, first, anthracene having a reactive substituent and a 1-fold mole-equivalent compound of a "moiety consisting of Ar and pyridine" are reacted and, thereafter, this intermediate is reacted with a compound of a "moiety consisting of Ar and pyridine" which is different from the previous moiety (that is, compounds are reacted by dividing the reaction into two stages).

In order to make two "moieties consisting of Ar and pyridine" have different structures, as another method, a method of using anthracene having a reactive substituent at any one of a 9-position and a 10-position as a raw material, reacting this with a compound of a "moiety consisting of Ar and pyridine", thereafter, further halogenating this intermediate, substituting the other position (a position at which the reaction has not been performed, of a 9-position and a 10-position) of an anthracene with a reactive group, and reacting the resultant with a compound of a "moiety consisting of Ar and pyridine" which is different from the previous moiety can be used.

(2) Method of Binding Pyridyl Group to Anthracene in which Ar Group is Bound to 9,10-Positions Also regarding this method, by reference to the above-mentioned various coupling reactions, first, an Ar group is bound to 9,10-positions of anthracene, and a pyridyl group may be bound to this Ar group. Thereupon, in order to make two "moieties consisting of Ar and pyridine" of the anthracene derivative represented by the formula (1) have different structures, a desired anthracene derivative can be synthesized by binding a different Ar group at a two-stage reaction at a stage where an Ar group is bound to anthracene, or by binding a different pyridyl group at a two-stage reaction at a stage where a pyridyl group is bound to an Ar group.

<For Reagent Used in Reaction>

Examples of the palladium catalyst used in the coupling reaction include tetrakis(triphenylphosphine)palladium (0): Pd(PPh$_3$)$_4$, bis(triphenylphosphine)palladium (II) dichloride: PdCl$_2$(PPh$_3$)$_2$, palladium (II) acetate: Pd(OAc)$_2$, tris(dibenzylideneacetone)dipalladium (0): Pd$_2$(dba)$_3$, tris(dibenzylideneacetone)dipalladium (0) chloroform complex: Pd$_2$(dba)$_3$·CHCl$_3$, bis(dibenzylideneacetone)palladium (0): Pd(dba)$_2$, bis(tri-t-butylphosphino)palladium (0): Pd(t-Bu$_3$P)$_2$, [1,1'-bis(diphenylphosphino)ferrocene]palladium (II) dichloride: Pd(dppf)Cl$_2$, [1,1'-bis(diphenylphosphino)ferrocene]palladium (II) dichloride dichloromethane complex (1:1): Pd(dppf)Cl$_2$·CH$_2$Cl$_2$, and PdCl$_2$[P(t-Bu)$_2$-(p-NMe$_2$-Ph)]$_2$: (A-$^{ta}$Phos)$_2$PdCl$_2$.

In order to promote a reaction, a phosphine compound may be optionally added to these palladium compounds. Examples of the phosphine compound include tri(t-butyl)phosphine, tricyclohexylphosphine, 1-(N,N-dimethylaminomethyl)-2-(di-t-butylphosphino)ferrocene, 1-(N,N-dibutylaminomethyl)-2-(di-t-butylphosphino)ferrocene, 1-(methoxymethyl)-2-(di-t-butylphosphino)ferrocene, 1,1'-bis(di-t-butylphosphino)ferrocene, 2,2'-bis(di-t-butylphosphino-1,1'-binaphthyl, 2-methoxy-2'-(di-t-butylphosphino)-1,1'-binaphthyl, and 2-dicyclohexylphosphino-2',6'-dimethoxybiphenyl.

Examples of the base used in the reaction include sodium carbonate, potassium carbonate, cesium carbonate, sodium bicarbonate, sodium hydroxide, potassium hydroxide, barium hydroxide, sodium ethoxide, sodium t-butoxide, sodium acetate, potassium acetate, tripotassium phosphate, and potassium fluoride.

Examples of the solvent used in the reaction include benzene, toluene, xylene, 1,2,4-trimethylbenzene, N,N-dimethylformamide, tetrahydrofuran, diethyl ether, t-butyl methyl ether, 1,4-dioxane, methanol, ethanol, t-butyl alcohol, cyclopentyl methyl ether and isopropyl alcohol. These solvents can be appropriately selected, and may be used alone, or may be used as a mixed solvent.

3. Organic Electroluminescent Element

The anthracene derivative according to the present invention can be used, for example, as a material for an organic electroluminescent element. Hereinbelow, the organic electroluminescent element according to this exemplary embodiment will be explained in detail. FIG. 1 is a schematic cross-sectional view showing the organic electroluminescent element according to this exemplary embodiment.

<Structure of Organic Electroluminescent Element>

The organic electroluminescent element 100 shown in FIG. 1 has a substrate 101, an anode 102 disposed on the substrate 101, a hole injection layer 103 disposed on the anode 102, a hole transport layer 104 disposed on the hole injection layer 103, a luminescent layer 105 disposed on the hole transport layer 104, an electron transport layer 106 disposed on the luminescent layer 105, an electron injection layer 107 disposed on the electron transport layer 106, and a cathode 108 disposed on the electron injection layer 107.

The organic electroluminescent element 100 may also have a constitution having, for example, the substrate 101, the cathode 108 disposed on the substrate 101, the electron injection layer 107 disposed on the cathode 108, the electron transport layer 106 disposed on the electron injection layer 107, the luminescent layer 105 disposed on the electron transport layer 106, the hole transport layer 104 disposed on the luminescent layer 105, the hole injection layer 103 disposed on the hole transport layer 104, and the anode 102 disposed on the hole injection layer 103, by reversing the order of preparation.

It is not necessary that all of the above-mentioned respective layers are essential, and the smallest constitutional unit is a constitution formed of the anode 102, the luminescent layer 105, the electron transport layer 106 and/or the electron injection layer 107, and the cathode 108, and the hole injection layer 103 and the hole transport layer 104 are layers that are optionally disposed. Furthermore, each of the above-mentioned respective layers may be formed of a single layer or plural layers.

Besides the above-mentioned "substrate/anode/hole injection layer/hole transport layer/luminescent layer/electron transport layer/electron injection layer/cathode", the aspect of the layers that constitute the organic electroluminescent element may be a constitutional aspect of "substrate/anode/hole transport layer/luminescent layer/electron transport layer/electron injection layer/cathode", "substrate/anode/hole injection layer/luminescent layer/electron transport layer/electron injection layer/cathode", "substrate/anode/hole injection layer/hole transport layer/luminescent layer/electron injection layer/cathode", "substrate/anode/hole injection layer/hole transport layer/luminescent layer/electron transport layer/cathode", "substrate/anode/luminescent layer/electron transport layer/electron injection layer/cathode", "substrate/anode/hole transport layer/luminescent layer/electron injection layer/cathode", "substrate/anode/hole transport layer/luminescent layer/electron transport layer/cathode", "substrate/anode/hole injection layer/luminescent layer/electron injection layer/cathode", "substrate/anode/hole injection layer/luminescent layer/electron transport layer/cathode", "substrate/anode/luminescent layer/electron transport layer/cathode" or "substrate/anode/luminescent layer/electron injection layer/cathode".

<Substrate in Organic Electroluminescent Element>

The substrate 101 forms the support of the organic electroluminescent element 100, and quartz, glass, metals, plastics and the like are generally used therefor. The substrate 101 is formed into a plate-shape, a film-shape or a sheet-shape according to the intended purpose, and for example, glass plates, metal plates, metal foils, plastic films or plastic sheets or the like are used. Among these, glass plates, and plates made of transparent synthetic resins such as polyesters, polymethacrylates, polycarbonates and polysulfones are preferable. As the glass substrate, soda lime glass, non-alkali glass and the like are used, and the thickness may be a thickness that is sufficient to retain mechanical strength, for example, may be 0.2 mm or more. The upper limit value of the thickness is, for example, 2 mm or less, preferably 1 mm or less. As the material for the glass, non-alkali glass is more preferable since it is preferable that the amount of eluted ion from the glass is small, and soda lime glass with a barrier coating of $SiO_2$ or the like is also commercially available, and thus this can be used. Furthermore, a gas barrier film of a dense silicon oxide film or the like may be disposed on at least one surface of the substrate 101 so as to enhance the gas barrier property, and especially, in the case when a plate, film or sheet made of a synthetic resin having low gas barrier property is used as the substrate 101, it is preferable to dispose a gas barrier film.

<Anode in Organic Electroluminescent Element>

The anode 102 plays a role in injecting holes into the luminescent layer 105. In the case when the hole injection layer 103 and/or the hole transport layer 104 is/are disposed between the anode 102 and the luminescent layer 105, holes are injected into the luminescent layer 105 through the layer (s).

As the material for forming the anode 102, inorganic compounds and organic compounds are exemplified. Examples of the inorganic compounds include metals (aluminum, gold, silver, nickel, palladium, chromium and the like), metal oxides (indium oxide, tinoxide, indium-tinoxide (ITO), indium-zinc oxide (IZO) and the like), halogenated metals (copper iodide and the like), copper sulfide, carbon black, ITO glass, NESA glass and the like. Examples of the organic compounds include electroconductive polymers such as polythiophenes such as poly(3-methylthiophene), polypyrroles and polyanilines. In addition, the material can be suitably selected from substances that are used as anodes for organic electroluminescent elements and used.

The resistance of the transparent electrode is not limited as long as a sufficient current for the luminescence of the luminescent element can be fed, but a low resistance is desirable in view of the consumed electrical power of the luminescent element. For example, although any ITO substrate of 300Ω/□ or less functions as an element electrode, it is currently possible to supply a substrate of about 10Ω/□. Therefore, it is especially desirable to use a low-resistant product of, for example, 100 to 5Ω/□, preferably 50 to 5Ω/□. The thickness of the ITO can be selected according to the resistance value, but the ITO is generally used between 50 to 200 nm in many cases.

<Hole Injection Layer and Hole Transport Layer in Organic Electroluminescent Element>

The hole injection layer 103 plays a role in efficiently injecting the holes that have been transferred from the anode 102 into the luminescent layer 105 or the hole transport layer 104. The hole transport layer 104 plays a role in efficiently transporting the holes that have been injected from the anode 102 or the holes that have been injected from the anode 102 through the hole injection layer 103 to the luminescent layer 105. The hole injection layer 103 and the hole transport layer 104 are respectively formed by laminating and mixing one kind or two or more kinds of hole injection/transport material (s), or by a mixture of the hole injection/transport material (s) and a polymer binder. Alternatively, the layers may be formed by adding an inorganic salt such as iron (III) chloride to the hole injection/transport material.

The hole injection/transport substance needs to efficiently inject/transport the holes from the positive electrode between the electrodes to which an electric field has been provided, and it is desirable that the hole injection efficiency is high and the injected holes are efficiently transported. For this purpose, a substance having a small ionization potential, a high hole mobility and excellent stability, in which impurities that become traps are difficult to generate during the production and use of the substance, is preferable.

As the material for forming the hole injection layer 103 and the hole transport layer 104, optional one can be used by selecting from compounds that have been conventionally used as charge transport materials for holes in photoconductor materials, p-type semiconductor, and known compounds that are used in hole injection layers and hole transport layers of organic electroluminescent elements. Specific examples thereof are carbazole derivatives (N-phenyl carbazole, polyvinyl carbazole and the like), biscarbazole derivatives such as bis(N-arylcarbazole) or bis(N-alkyl carbazole), triarylamine derivatives (polymers having an aromatic tertiary amino group in the main chain or side chain, triphenylamine derivatives such as 1,1-bis(4-di-p-tolylaminophenyl)cyclohexane, N,N'-diphenyl-N,N'-di(3-methylphenyl)-4,4'-diaminobiphenyl, N,N'-diphenyl-N,N'-dinaphthyl-4,4'-diaminobiphenyl, N,N'-diphenyl-N,N'-di(3-methylphenyl)-4,4'-diphenyl-1,1'-diamine, N,N'-dinaphthyl-N,N'-diphenyl-4,4'-diphenyl-1,1'-diamine and 4,4',4"-tris(3-methylphenyl(phenyl)amino)triphenylamine, starburst amine derivatives and the like), stilbene derivatives, phthalocyanine derivatives (metal-free, copper phthalocyanine and the like), heterocycle compounds such as pyrazoline derivatives, hydrazone-based compounds, benzofuran derivatives and thiophene derivatives, oxadiazole derivatives and porphyrin derivatives, polysilanes and the like. As polymer-based compounds, polycarbonates having the above-mentioned monomers on the side chains, styrene derivatives, polyvinyl carbazole and polysilanes and the like are preferable, but are not especially limited as long as they are compounds capable of forming a thin film required for the preparation of a luminescent element, capable of injecting holes from the anode and capable of transporting holes.

Furthermore, it is also known that the electroconductivity of an organic semiconductor is strongly affected by the doping thereof. Such organic semiconductor matrix substance is constituted by a compound having fine electron-donating property or a compound having fine electron-accepting property. For doping of an electron-donating substance, strong electron receptors such as tetracyanoquinonedimethane (TCNQ) or 2,3,5,6-tetrafluorotetracyano-1,4-benzoquinonedimethane (F4TCNQ) are known (for example, see the document "M. Pfeiffer, A. Beyer, T. Fritz, K. Leo, Appl. Phys. Lett., 73 (22), 3202-3204 (1998)" and the document "J. Blochwitz, M. Pheiffer, T. Fritz, K. Leo, Appl. Phys. Lett., 73 (6), 729-731 (1998)"). These generate so-called holes by an electron transfer process in an electron-donating type base substance (hole transport substance). The conductivity of the base substance varies quite significantly depending on the number and mobility of the holes. As the matrix substances having hole transport property, for example, benzidine derivatives (TPD and the like)

or starburst amine derivatives (TDATA and the like), or specific metal phthalocyanines (especially, zinc phthalocyanine ZnPc and the like) are known (JP 2005-167175 A).

<Luminescent Layer in Organic Electroluminescent Element>

The luminescent layer 105 emits light by recombining the holes that have been injected from the anode 102 and the electrons that have been injected from the cathode 108 between the electrodes to which an electric field has been provided. The material for forming the luminescent layer 105 may be a compound that emits light by being excited by the recombination of holes and electrons (luminescent compound), and is preferably a compound that can form a stable thin film shape and show strong luminescence (fluorescence and/or phosphorescence) efficiency in a solid state.

The luminescent layer may be formed of a single layer or plural layers, each of which is formed of a luminescent material (a host material, a dopant material). The host material and dopant material each may be either one kind or a combination of plural kinds. The dopant material may be contained either in the entirety or a part of the host material. As the doping process, the dopant material can be formed by a process for co-deposition with the host material, or may be mixed with the host material in advance and simultaneously deposited.

The use amount of the host material differs depending on the kind of the host material, and may be determined according to the property of the host material. The rough standard of the use amount of the host material is preferably from 50 to 99.999% by weight, more preferably from 80 to 99.95% by weight, and further preferably from 90 to 99.9% by weight with respect to the entirety of the luminescent material.

The use amount of the dopant material differs depending on the kind of the dopant material, and may be determined according to the property of the dopant material (for example, when the use amount is too much, a concentration quenching phenomenon may arise). The rough standard of the use amount of the dopant is preferably from 0.001 to 50% by weight, more preferably from 0.05 to 20% by weight, and further preferably from 0.1 to 10% by weight with respect to the entirety of the luminescent material.

The luminescent material of the luminescent element according to the present exemplary embodiment may be either fluorescent or phosphorescent.

The host material is not especially limited, and condensed ring derivatives such as anthracene and pyrene that have been known as luminescent substances since before, metal chelated oxinoid compounds including tris(8-quinolinolato) aluminum, bisstyryl derivatives such as bisstyrylanthracene derivatives and distyrylbenzene derivatives, tetraphenylbutadiene derivatives, coumarin derivatives, oxadiazole derivatives, pyrrolopyridine derivatives, perinone derivatives, cyclopentadiene derivatives, thiadiazolopyridine derivatives, pyrrolopyrrole derivatives, fluorene derivatives, benzofluorene derivatives, and polymers such as polyphenylenevinylene derivatives, polyparaphenylene derivatives and polythiophene derivatives are preferably used.

In addition, the host material can be suitably selected from the compounds described in Chemical Industry, June 2004, page 13, and the reference documents cited therein, and the like, and used.

The dopant materials are not especially limited, and already-known compounds can be used, and can be selected from various materials according to the desired color of luminescence. Specific examples include condensed ring derivatives such as phenanthrene, anthracene, pyrene, tetracene, pentacene, perylene, naphthopyrene, dibenzopyrene, rubrene and chrysene, benzoxazole derivatives, benzothiazole derivatives, benzimidazole derivatives, benzotriazole derivatives, oxazole derivatives, oxadiazole derivatives, thiazole derivatives, imidazole derivatives, thiadiazole derivatives, triazole derivatives, pyrazoline derivatives, stilbene derivatives, thiophene derivatives, tetraphenylbutadiene derivatives, cyclopentadiene derivatives, bisstyryl derivatives such as bisstyrylanthracene derivatives and distyrylbenzene derivatives (JP 1-245087 A), bisstyrylarylene derivatives (JP 2-247278 A), diazaindacene derivatives, furan derivatives, benzofuran derivatives, isobenzofuran derivatives such as phenylisobenzofuran, dimesitylisobenzofuran, di(2-methylphenyl)isobenzofuran, di(2-trifluoromethylphenyl)isobenzofuran and phenylisobenzofuran, dibenzofuran derivatives, coumarin derivatives such as 7-dialkylaminocoumarin derivatives, 7-piperidinocoumarin derivatives, 7-hydroxycoumarin derivatives, 7-methoxycoumarinderivatives, 7-acetoxycoumarin derivatives, 3-benzothiazolylcoumarin derivatives, 3-benzimidazolylcoumarin derivatives and 3-benzoxazolylcoumarin derivatives, dicyanomethylenepyran derivatives, dicyanomethylenethiopyran derivatives, polymethine derivatives, cyanine derivatives, oxobenzoanthracene derivatives, xanthene derivatives, rhodamine derivatives, fluorescein derivatives, pyrylium derivatives, carbostyryl derivatives, acridine derivatives, oxazine derivatives, phenyleneoxide derivatives, quinacridone derivatives, quinazoline derivatives, pyrrolopyridine derivatives, furopyridine derivatives, 1,2,5-thiadiazolopyrene derivatives, pyrromethene derivatives, perinone derivatives, pyrrolopyrrole derivatives, squarylium derivatives, violanthrone derivatives, phenazine derivatives, acridone derivatives, deazaflavin derivatives, fluorene derivatives and benzofluorene derivatives.

The dopant materials will be exemplified for every colored light. Examples of blue to blue green dopant materials include aromatic hydrocarbon compounds such as naphthalene, anthracene, phenanthrene, pyrene, triphenylene, perylene, fluorine, indene and chrysene and derivatives thereof, aromatic heterocycle compounds such as furan, pyrrole, thiophene, silole, 9-silafluorene, 9,9'-spirobisilafluorene, benzothiophene, benzofuran, indole, dibenzothiophene, dibenzofuran, imidazopyridine, phenanthroline, pyrazine, naphthylidine, quinoxaline, pyrrolopyridine and thioxanthene and derivatives thereof, distyrylbenzene derivatives, tetraphenylbutadiene derivatives, stilbene derivatives, aldazine derivatives, coumarin derivatives, azole derivatives such as imidazole, thiazole, thiadiazole, carbazole, oxazole, oxadiazole and triazole and metal complexes thereof, and aromatic amine derivatives represented by N,N'-diphenyl-N,N'-di(3-methylphenyl)-4,4'-diphenyl-1,1'-diamine, and the like.

Furthermore, examples of green to yellow dopant materials include coumarin derivatives, phthalimide derivatives, naphthalimide derivatives, perinone derivatives, pyrrolopyrrole derivatives, cyclopentadiene derivatives, acridone derivatives, quinacridone derivatives and naphthacene derivatives such as rubrene, and the like, and also include, as preferable examples, compounds obtained by introducing a substituent that enables red-shifting such as an aryl group, a heteroaryl group, an arylvinyl group, amino group and cyano group into the compounds exemplified as the above-mentioned blue to blue green dopant materials.

Furthermore, examples of orange to red dopant materials include naphthalimide derivatives such as bis(diisopropylphenyl)perylene tetracarboxylic acid imide, perinone derivatives, rare earth complexes including acetylacetone or benzoylacetone and phenanthroline or the like as ligands such as Eu complex, 4-(dicyanomethylene)-2-methyl-6-(p-dimethylaminostyryl)-4H-pyran and analogues thereof, metalphthalocyanine derivatives such as magnesium phthalocyanine and aluminum chlorophthalocyanine, rhodamine compounds, deazaflavin derivatives, coumarin derivatives, quinacridone derivatives, phenoxazine derivatives, oxazin derivatives, quinazoline derivatives, pyrrolopyridine derivatives, squarylium derivatives, violanthrone derivatives, phenazine derivatives, phenoxazone derivatives and thiadiazolopyrene derivatives, and the like, and also include, as preferable examples, compounds obtained by introducing a substituent that enables red-shifting such as an aryl group, a heteroaryl group, an arylvinyl group, amino group and cyano group into the compounds exemplified as the above-mentioned blue to blue green and green to yellow dopant materials. In addition, phosphorescent metal complexes containing iridium or platinum as a center metal represented by tris(2-phenylpyridine) iridium (III) are also exemplified as preferable examples.

Other dopants can be used by suitably selecting from the compounds described in Chemical Industry, June 2004, page 13 and the reference documents cited therein, and the like.

Among the dopant materials mentioned above, especially, perylene derivatives, borane derivatives, amine-containing styryl derivatives, aromatic amine derivatives, coumarin derivatives, pyran derivatives, iridium complexes or platinum complexes are preferable.

Examples of the perylene derivatives include 3,10-bis(2,6-dimethylphenyl)perylene, 3,10-bis(2,4,6-trimethylphenyl)perylene, 3,10-diphenylperylene, 3,4-diphenylperylene, 2,5,8,11-tetra-t-butylperylene, 3,4,9,10-tetraphenylperylene, 3-(1'-pyrenyl)-8,11-di(t-butyl)perylene, 3-(9'-anthryl)-8,11-di(t-butyl)perylene, 3,3'-bis(8,11-di(t-butyl)perylenyl) and the like.

Alternatively, the perylene derivatives described in JP 11-97178 A, JP 2000-133457 A, JP 2000-26324 A, JP 2001-267079 A, JP 2001-267078 A, JP 2001-267076 A, JP 2000-34234 A, JP 2001-267075 A and JP 2001-217077 A, and the like may also be used.

Examples of the borane derivatives include 1,8-diphenyl-10-(dimesitylboryl)anthracene, 9-phenyl-10-(dimesitylboryl)anthracene, 4-(9'-anthryl)dimesitylborylnaphthalene, 4-(10'-phenyl-9'-anthryl)dimesitylborylnaphthalene, 9-(dimesitylboryl)anthracene, 9-(4'-biphenylyl)-10-(dimesitylboryl)anthracene, 9-(4'-(N-carbazolyl)phenyl)-10-(dimesitylboryl)anthracene and the like.

Alternatively, the borane derivatives described in WO 2000/40586 A and the like may also be used.

Examples of the amine-containing styryl derivatives include N,N,N',N'-tetra(4-biphenylyl)-4,4'-diaminostilbene, N,N,N',N'-tetra(1-naphthyl)-4,4'-diaminostilbene, N,N,N',N'-tetra(2-naphthyl)-4,4'-diaminostilbene, N,N'-di(2-naphthyl)-N,N'-diphenyl-4,4'-diaminostilbene, N,N'-di(9-phenanthryl)-N,N'-diphenyl-4,4'-diaminostilbene, 4,4'-bis[4''-bis(diphenylamino)styryl]-biphenyl, 1,4-bis[4'-bis(diphenylamino)styryl]-benzene, 2,7-bis[4'-bis(diphenylamino)styryl]-9,9-dimethylfluorene, 4,4'-bis(9-ethyl-3-carbazovinylene)-biphenyl, 4,4'-bis(9-phenyl-3-carbazovinylene)-biphenyl and the like. Alternatively, the amine-containing styryl derivatives described in JP 2003-347056 A and JP 2001-307884 A, and the like may also be used.

Examples of the aromatic amine derivatives include N,N,N,N-tetraphenylanthracene-9,10-diamine, 9,10-bis(4-diphenylamino-phenyl)anthracene, 9,10-bis(4-di(1-naphthylamino)phenyl)anthracene, 9,10-bis(4-di(2-naphthylamino)phenyl)anthracene, 10-di-p-tolylamino-9-(4-di-p-tolylamino-1-naphthyl)anthracene, 10-diphenylamino-9-(4-diphenylamino-1-naphthyl)anthracene, 10-diphenylamino-9-(6-diphenylamino-2-naphthyl)anthracene, [4-(4-diphenylamino-phenyl)naphthalen-1-yl]-diphenylamine, [6-(4-diphenylamino-phenyl)naphthalen-2-yl]-diphenylamine, 4,4'-bis[4-diphenylaminonaphthalen-1-yl]biphenyl, 4,4'-bis[6-diphenylaminonaphthalen-2-yl]biphenyl, 4,4''-bis[4-diphenylaminonaphthalen-1-yl]-p-terphenyl, 4,4''-bis[6-diphenylaminonaphthalen-2-yl]-p-terphenyl and the like.

Alternatively, the aromatic amine derivatives described in JP 2006-156888 A and the like may also be used.

Examples of the coumarin derivatives include coumarin-6, coumarin-334 and the like.

Alternatively, the coumarin derivatives described in JP 2004-43646 A, JP 2001-76876 A and JP 6-298758 A, and the like may also be used.

Examples of the pyran derivatives include DCM, DCJTB and the like mentioned below.

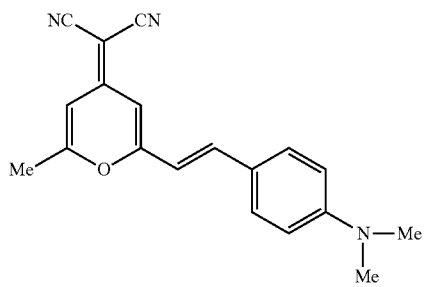

DCM

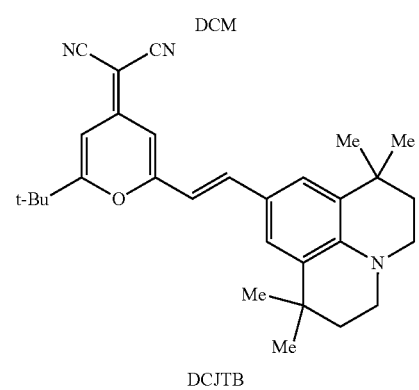

DCJTB

Alternatively, the pyran derivatives described in JP 2005-126399A, JP2005-097283A, JP2002-234892 A, JP 2001-220577 A, JP 2001-081090 A and JP 2001-052869 A, and the like may also be used.

Examples of the iridium complexes include Ir(ppy)$_3$ mentioned below, and the like.

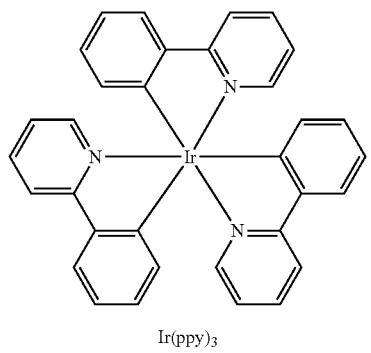

Ir(ppy)$_3$

Alternatively, the iridium complexes described in JP 2006-089398A, JP 2006-080419A, JP 2005-298483 A, JP 2005-097263 A and JP 2004-111379 A, and the like may also be used.

Examples of the platinum complexes include PtOEP mentioned below, and the like.

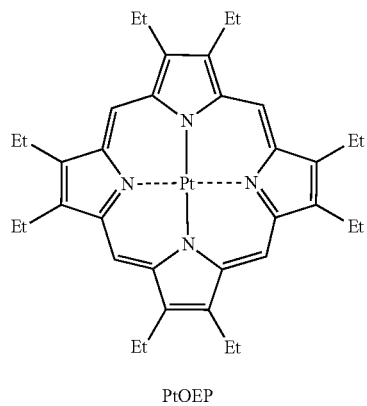

PtOEP

Alternatively, the platinum complexes described in JP 2006-190718A, JP 2006-128634 A, JP 2006-093542 A, JP 2004-335122 A, and JP 2004-331508 A, and the like may also be used.

<Electron Injection Layer and Electron Transport Layer Inorganic Electroluminescent Element>

The electron injection layer 107 plays a role in efficiently injecting the electrons that have been transferred from the cathode 108 into the luminescent layer 105 or the electron transport layer 106. The electron transport layer 106 plays a role in efficiently transporting the electrons that have been injected from the cathode 108 or the electrons that have been injected from the cathode 108 through the electron injection layer 107 to the luminescent layer 105. The electron transport layer 106 and the electron injection layer 107 are respectively formed by laminating and mixing one kind or two or more kinds of electron transport/injection material (s), or by a mixture of the electron transport/injection material (s) and a polymer binder.

The electron injection/transport layer is a layer that controls the injection of electrons from the cathode and further transport of the electrons, and it is desirable that the layer has a high electron injection efficiency and efficiently transports the injected electrons. For that purposes, a substance that has high electron affinity and a high electron transfer degree and excellent stability, in which impurities that become traps are difficult to be generated during the production and use, is preferable. However, in the case when the balance of transportation of holes and electrons is taken into consideration, in the case when the substance mainly plays a role that enables efficient blocking of the flowing of the holes from the anode to the cathode side without recombination, the substance has an equivalent effect of improving luminescence efficiency to that of a material having high electron transportability, even the electron transportability is not so high. Therefore, the electron injection/transport layer in this exemplary embodiment may also include a function of a layer capable of efficiently blocking the transfer of holes.

As the material for forming the electron transport layer 106 or electron injection layer 107 (electron transport material), the compound represented by the above-mentioned formula (1) can be used. Of these, the anthracene derivatives represented by the above-mentioned formula (1-1) to formula (1-66) are preferable.

The content of the anthracene derivative represented by the above-mentioned formula (1) in the electron transport layer 106 or electron injection layer 107 differs depending on the kind of the derivative, and may be determined according to the property of the derivative. The rough standard of the content of the anthracene derivative represented by the above-mentioned formula (1) is preferably from 1 to 100% by weight, more preferably from 10 to 100% by weight, further preferably from 50 to 100% by weight, and especially preferably from 80 to 100% by weight with respect to the entirety of the electron transport layer material (or the electron injection layer material). In the case when the anthracene derivative represented by the above-mentioned formula (1) is not used singly (100% by weight), it is preferable to incorporate other materials that are mentioned below in detail.

The other materials for forming the electron transport layer or electron injection layer can be used by optionally selecting from compounds that have been conventionally used since before as electron transfer compounds in photoconductor materials, and known compounds that are used in electron injection layers and electron transport layers of organic electoluminescent elements.

It is preferable that the material for use in the electron transport layer or electron injection layer contains at least one kind selected from compounds including an aromatic ring or a heteroaromatic ring composed of one or more kind of atom selected from carbon, hydrogen, oxygen, sulfur, silicon and phosphorus, pyrrole derivatives and condensed ring derivatives thereof, and metal complexes having electron-accepting nitrogen. Specific examples include condensed ring-based aromatic ring derivatives such as naphthalene and anthracene, styryl-based aromatic ring derivatives including 4,4'-bis(diphenylethenyl) biphenyl, perinone derivatives, coumarin derivatives, naphthalimide derivatives, quinone derivatives such as anthraquinone and diphenoquinone, phosphoroxide derivatives, carbazole derivatives and indole derivatives. Examples of the metal complexes having electron-accepting nitrogen include hydroxyazole complexes such as hydroxyphenyloxazole complexes, azomethine complexes, tropolone metal complexes, flavonol metal complexes and benzoquinoline metal complexes. These materials are used singly, or may be used by mixing with different materials. Among these, anthracene derivatives such as 9,10-bis(2-naphthyl)anthracene, styryl-based aromatic ring derivatives such as 4,4'-bis(diphenylethenyl)biphenyl, carbazole derivatives such as 4,4'-bis(N-carbazolyl)biphenyl and 1,3,5-tris(N-carbazolyl)benzene are preferably used in view of durability.

Furthermore, specific examples of the other electron transfer compounds include pyridine derivatives, naphthalene derivatives, anthracene derivatives, phenanthroline derivatives, perinone derivatives, coumarin derivatives, naphthalimide derivatives, anthraquinone derivatives, diphenoquinone derivatives, diphenylquinone derivatives, perylene derivatives, oxadiazole derivatives (1,3-bis[(4-t-butylphenyl)1,3,4-oxadiazolyl]phenylene and the like), thiophene derivatives, triazole derivatives (N-naphthyl-2,5-diphenyl-1,3,4-triazole and the like), thiadiazole derivatives, metal complexes of oxine derivatives, quinolinol-based metal complexes, quinoxaline derivatives, polymers of quinoxaline derivatives, benzazole compounds, gallium complexes, pyrazole derivatives, perfluorinated phenylene derivatives, triazine derivatives, pyrazine derivatives, benzoquinoline derivatives (2,2'-bis(benzo[h]quinolin-2-yl)-9,9'-spirobifluorene and the like), imidazopyridine derivatives, borane derivatives, benzimidazole derivatives (tris(N-phenylbenzimidazol-2-yl)benzene and the like), benzoxazole derivatives, benzothiazole derivatives, quinoline derivatives, oligopyridine derivatives such as terpyridine, bipyridine derivatives, terpyridine derivatives (1,3-bis(4'-(2,2':6'2"-terpyridinyl))benzene and the like), naphthylidine derivatives (bis(1-naphthyl)-4-(1,8-naphthylidin-2-yl)phenylphosphine oxide and the like), aldazine derivatives, carbazole derivatives, indole derivatives, phosphoroxide derivatives, bisstyryl derivatives and the like.

Alternatively, metal complexes having electron-accepting nitrogen can also be used, and examples include quinolinol-based metal complexes, hydroxyazole complexes such as hydroxyphenyloxazole complexes, azomethine complexes, tropolone metal complexes, flavonol metal complexes and benzoquinoline metal complexes.

The above-mentioned materials are used singly, or may be used by mixing with different materials.

Among the above-mentioned materials, quinolinol-based metal complexes, bipyridine derivatives, phenanthroline derivatives, borane derivatives or benzimidazole derivatives are preferable.

The quinolinol-based metal complexes are compound represented by the following formula (E-1).

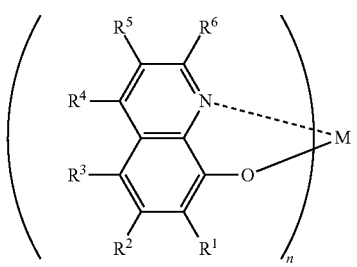
(E-1)

In the formula, $R^1$ to $R^6$ are each hydrogen or a substituent, M is Li, Al, Ga, Be or Zn, and n is an integer of 1 to 3.

Specific examples of the quinolinol-based metal complexes include 8-quinolinollithium, tris(8-quinolinolate)aluminum, tris(4-methyl-8-quinolinolate)aluminum, tris(5-methyl-8-quinolinolate)aluminum, tris(3,4-dimethyl-8-quinolinolate)aluminum, tris(4,5-dimethyl-8-quinolinolate)aluminum, tris(4,6-dimethyl-8-quinolinolate)aluminum, bis(2-methyl-8-quinolinolate)(phenolate)aluminum, bis(2-methyl-8-quinolinolate)(2-methylphenolate)aluminum, bis(2-methyl-8-quinolinolate)(3-methylphenolate)aluminum, bis(2-methyl-8-quinolinolate)(4-methylphenolate)aluminum, bis(2-methyl-8-quinolinolate)(2-phenylphenolate)aluminum, bis(2-methyl-8-quinolinolate)(3-phenylphenolate)aluminum, bis(2-methyl-8-quinolinolate)(4-phenylphenolate)aluminum, bis(2-methyl-8-quinolinolate)(2,3-dimethylphenolate)aluminum, bis(2-methyl-8-quinolinolate)(2,6-dimethylphenolate)aluminum, bis(2-methyl-8-quinolinolate)(3,4-dimethylphenolate)aluminum, bis(2-methyl-8-quinolinolate)(3,5-dimethylphenolate)aluminum, bis(2-methyl-8-quinolinolate)(3,5-di-t-butylphenolate)aluminum, bis(2-methyl-8-quinolinolate)(2,6-diphenylphenolate)aluminum, bis(2-methyl-8-quinolinolate)(2,4,6-triphenylphenolate)aluminum, bis(2-methyl-8-quinolinolate)(2,4,6-trimethylphenolate)aluminum, bis(2-methyl-8-quinolinolate)(2,4,5,6-tetramethylphenolate)aluminum, bis(2-methyl-8-quinolinolate)(1-naphtholate)aluminum, bis(2-methyl-8-quinolinolate)(2-naphtholate)aluminum, bis(2,4-dimethyl-8-quinolinolate)(2-phenylphenolate)aluminum, bis(2,4-dimethyl-8-quinolinolate)(3-phenylphenolate)aluminum, bis(2,4-dimethyl-8-quinolinolate)(4-phenylphenolate)aluminum, bis(2,4-dimethyl-8-quinolinolate)(3,5-dimethylphenolate) aluminum, bis(2,4-dimethyl-8-quinolinolate)(3,5-di-t-butylphenolate)aluminum, bis(2-methyl-8-quinolinolate)aluminum-t-oxo-bis(2-methyl-8-quinolinolate)aluminum, bis(2,4-dimethyl-8-quinolinolate)aluminum-μ-oxo-bis(2,4-dimethyl-8-quinolinolate)aluminum, bis(2-methyl-4-ethyl-8-quinolinolate)aluminum-μ-oxo-bis(2-methyl-4-ethyl-8-quinolinolate)aluminum, bis(2-methyl-4-methoxy-8-quinolinolate)aluminum-μ-oxo-bis(2-methyl-4-methoxy-8-quinolinolate)aluminum, bis(2-methyl-5-cyano-8-quinolinolate)aluminum-μ-oxo-bis(2-methyl-5-cyano-8-quinolinolate)aluminum, bis(2-methyl-5-trifluoromethyl-8-quinolinolate)aluminum-μ-oxo-bis(2-methyl-5-trifluoromethyl-8-quinolinolate)aluminum, bis(10-hydroxybenzo[h]quinoline)beryllium and the like.

The bipyridine derivatives are compounds represented by the following formula (E-2).

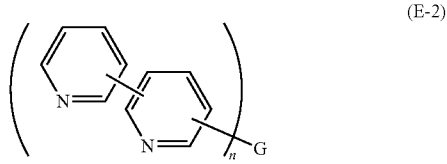
(E-2)

In the formula, G represents a simple bond or a linking group with a valency of n, and n is an integer of 2 to 8. Furthermore, the carbon atoms that are not used for the bonding of pyridine-pyridine or pyridine-G may be substituted.

Examples of G in the formula (E-2) include those having the following structural formulas. The Rs in the following structural formulas are each independently hydrogen, methyl, ethyl, isopropyl, cyclohexyl, phenyl, 1-naphthyl, 2-naphthyl, biphenylyl or terphenylyl.

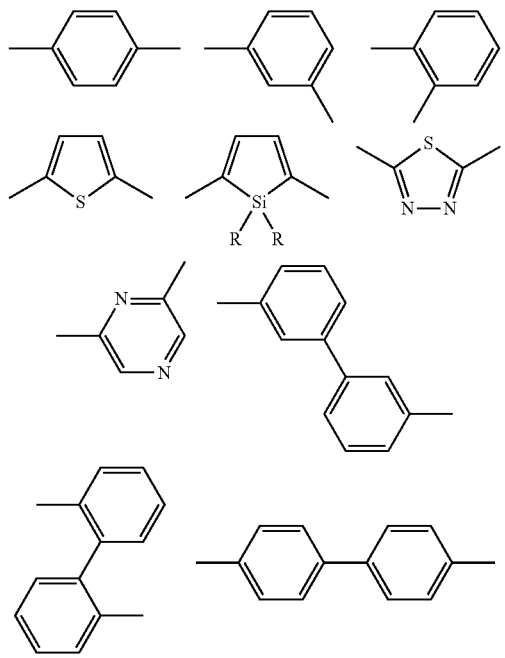

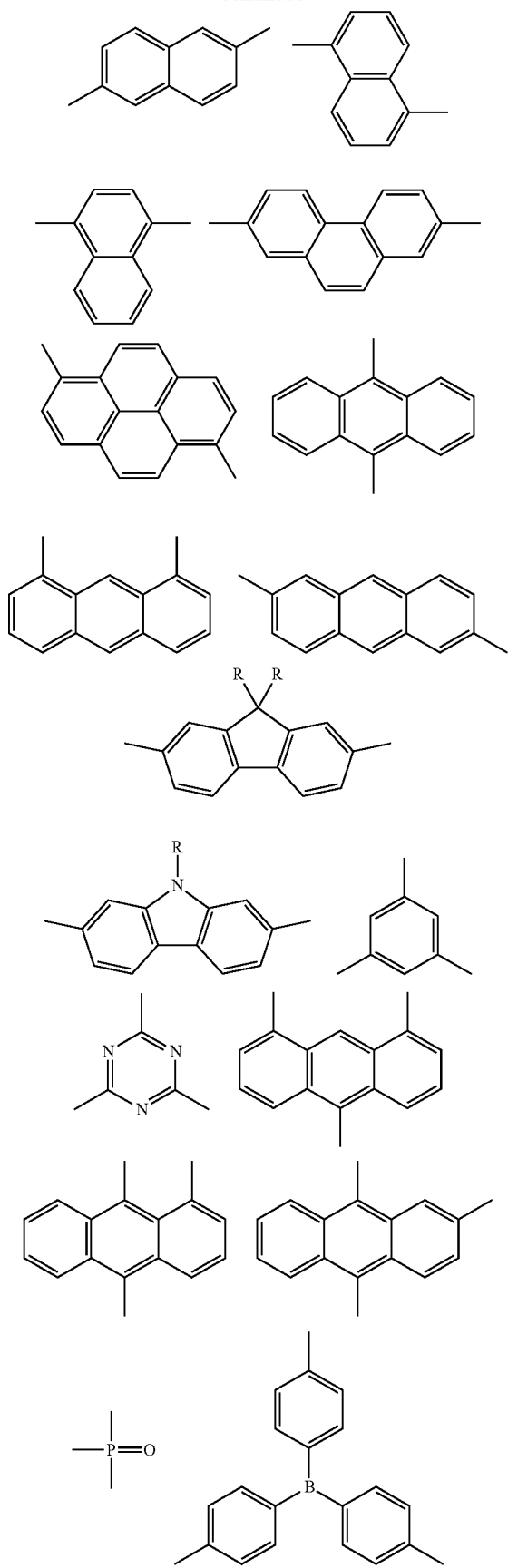

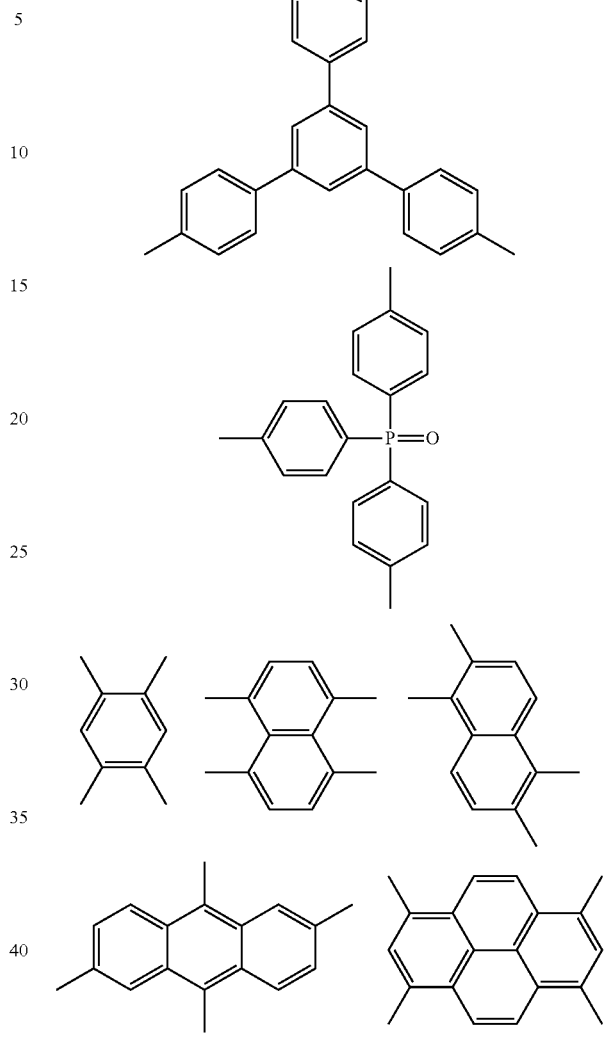

Specific examples of the pyridine derivatives are 2,5-bis (2,2'-bipyridin-6-yl)-1,1-dimethyl-3,4-diphenylsilole, 2,5-bis(2,2'-bipyridin-6-yl)-1,1-dimethyl-3,4-dimesitylsilole, 2,5-bis(2,2'-bipyridin-5-yl)-1,1-dimethyl-3,4-diphenylsilole, 2,5-bis(2,2'-bipyridin-5-yl)-1,1-dimethyl-3,4-dimesitylsilole, 9,10-di(2,2'-bipyridin-6-yl)anthracene, 9,10-di(2,2'-bipyridin-5-yl)anthracene, 9,10-di(2,3'-bipyridin-6-yl)anthracene, 9,10-di(2,3'-bipyridin-5-yl)anthracene, 9,10-di(2,3'-bipyridin-6-yl)-2-phenylanthracene, 9,10-di(2,3'-bipyridin-5-yl)-2-phenylanthracene, 9,10-di(2,2'-bipyridin-6-yl)-2-phenylanthracene, 9,10-di(2,2'-bipyridin-5-yl)-2-phenylanthracene, 9,10-di(2,4'-bipyridin-6-yl)-2-phenylanthracene, 9,10-di(2,4'-bipyridin-5-yl)-2-phenylanthracene, 9,10-di(3,4'-bipyridin-6-yl)-2-phenylanthracene, 9,10-di(3,4'-bipyridin-5-yl)-2-phenylanthracene, 3,4-diphenyl-2,5-di(2,2'-bipyridin-6-yl)thiophene, 3,4-diphenyl-2,5-di(2,3'-bipyridin-5-yl)thiophene, 6'6"-di(2-pyridyl)2,2':4',4":2",2'"-quaterpyridine and the like.

The phenanthroline derivatives are compounds represented by the following formula (E-3-1) or (E-3-2).

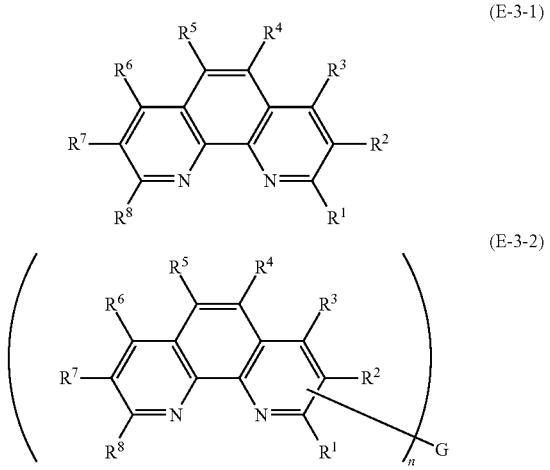

(E-3-1)

(E-3-2)

In the formulas, $R^1$ to $R^8$ are each hydrogen or a substituent, where in the adjacent groups may bind to each other to form a condensed ring, G represents a simple bond or a linking group with a valency of n, and n is an integer of 2 to 8. Furthermore, examples of G in the formula (E-3-2) include those similar to those explained in the column of the bipyridine derivatives.

Specific examples of the phenanthroline derivatives include 4,7-diphenyl-1,10-phenanthroline, 2,9-dimethyl-4,7-diphenyl-1,10-phenanthroline, 9,10-di(1,10-phenanthrolin-2-yl) anthracene, 2,6-di(1,10-phenanthrolin-5-yl)pyridine, 1,3,5-tri(1,10-phenanthrolin-5-yl)benzene, 9,9'-difluoro-bi(1,10-phenanthrolin-5-yl), bathocuproine, 1,3-bis(2-phenyl-1,10-phenanthrolin-9-yl)benzene and the like.

Especially, the case when a phenanthroline derivative is used in the electron transport layer and the electron injection layer will be explained. In order to obtain stable luminescent over a long time, a material that is excellent in thermal stability and thin film formability is desired, and among phenanthroline derivatives, those having substituents in which the substituents themselves have three-dimensional steric structures or those having three-dimensional steric structures by the steric repulsion with the phenanthroline backbone or the adjacent substituents, or those formed by linking plural phenanthroline backbones are preferable. Furthermore, in the case when plural phenanthroline backbones are connected, compounds containing conjugate bonds, substituted or unsubstituted aromatic hydrocarbons or substituted or unsubstituted aromatic heterocycles in the linked units are more preferable.

The borane derivatives are compounds represented by the following formula (E-4), and the details thereof are disclosed in JP 2007-27587 A.

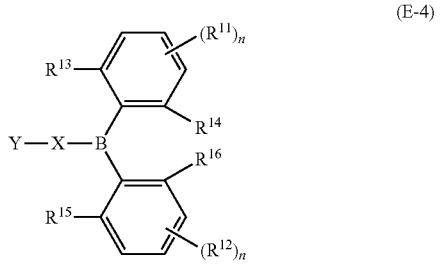

(E-4)

In the formula, $R^{11}$ and $R^{12}$ are each independently at least one of hydrogen atom, an alkyl group, an optionally substituted aryl group, a substituted silyl group, an optionally substituted nitrogen-containing heterocycle group or cyano group, $R^{13}$ to $R^{16}$ are each independently an optionally substituted alkyl group or an optionally substituted aryl group, X is an optionally substituted arylene group, Y is an optionally substituted aryl group, substituted boryl group or optionally substituted carbazole group with a carbon number of 16 or less, and ns are each independently an integer of 0 to 3.

Among the compounds represented by the above-mentioned formula (E-4), compounds represented by the following formula (E-4-1) and compounds represented by the following formulas (E-4-1-1) to (E-4-1-4) are preferable. Specific examples include 9-[4-(4-dimesitylborylnaphthalen-1-yl)phenyl]carbazole, 9-[4-(4-dimesitylborylnaphthalen-1-yl) naphthalen-1-yl]carbazole and the like.

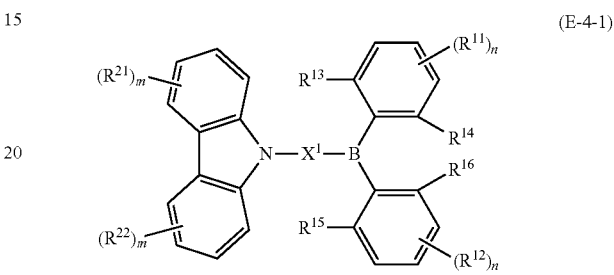

(E-4-1)

In the formula, $R^{11}$ and $R^{12}$ are each independently at least one of hydrogen atom, an alkyl group, an optionally substituted aryl group, a substituted silyl group, an optionally substituted nitrogen-containing heterocycle group or cyano group, $R^{13}$ to $R^{16}$ are each independently an optionally substituted alkyl group or an optionally substituted aryl group, $R^{21}$ and $R^{22}$ are each independently at least one of hydrogen atom, an alkyl group, an optionally substituted aryl group, a substituted silyl group, an optionally substituted nitrogen-containing heterocycle group or cyano group, $X^1$ is an optionally substituted arylene group with a carbon number of 20 or less, ns are each independently an integer of 0 to 3, and ms are each independently an integer of 0 to 4.

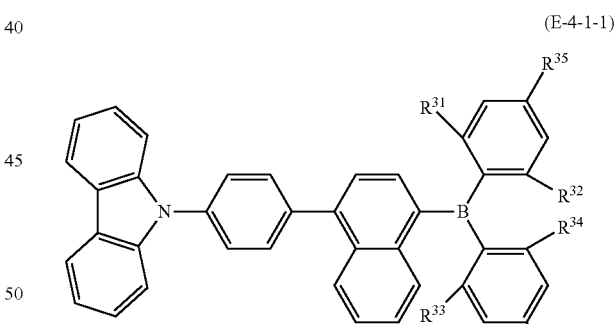

(E-4-1-1)

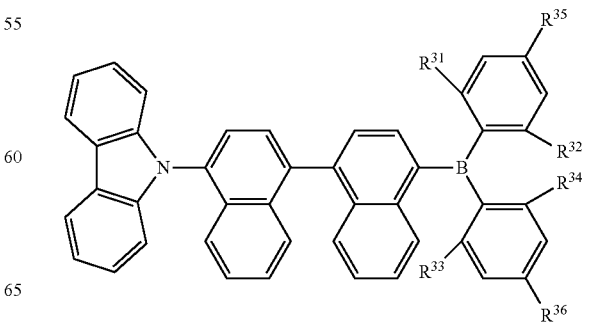

(E-4-1-2)

-continued (E-4-1-3)

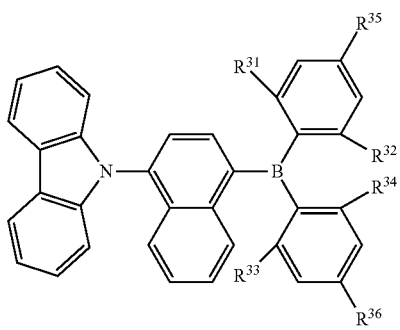

(E-4-2-1)

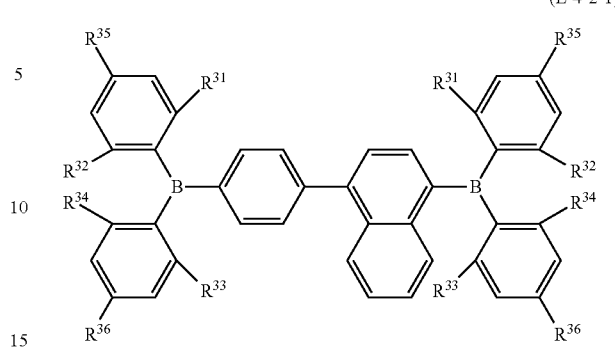

In the formula, $R^{31}$ to $R^{34}$ are each independently any of methyl, isopropyl or phenyl, and $R^{35}$ and $R^{36}$ are each independently any of hydrogen, methyl, isopropyl or phenyl.

Among the compounds represented by the above-mentioned formula (E-4), the compounds represented by the following formula (E-4-3), the compounds represented by the following formula (E-4-3-1) or the compounds represented by the following formula (E-4-3-2) are preferable.

(E-4-1-4)

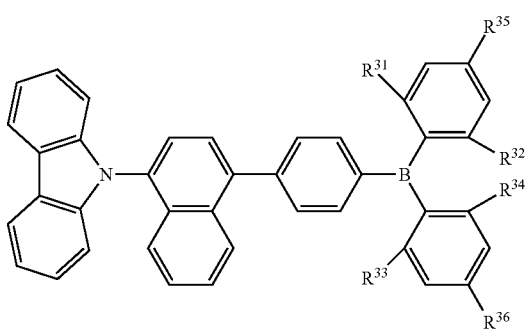

(E-4-3)

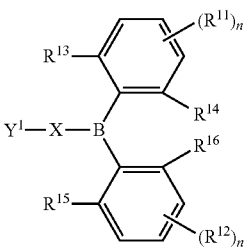

In each formula, $R^{31}$ to $R^{34}$ are each independently any of methyl, isopropyl or phenyl, and $R^{35}$ and $R^{36}$ are each independently any of hydrogen, methyl, isopropyl or phenyl.

Among the compounds represented by the above-mentioned formula (E-4), the compounds represented by the following formula (E-4-2) and the compounds represented by the following formula (E-4-2-1) are preferable.

In the formula, $R^{11}$ and $R^{12}$ are each independently at least one of hydrogen atom, an alkyl group, an optionally substituted aryl group, a substituted silyl group, an optionally substituted nitrogen-containing heterocycle group or cyano group, $R^{13}$ to $R^{16}$ are each independently an optionally substituted alkyl group or an optionally substituted aryl group, $X^1$ is an optionally substituted arylene group with a carbon number of 10 or less, $Y^1$ is an optionally substituted aryl group with a carbon number of 14 or less, and ns are each independently an integer of 0 to 3.

(E-4-2)

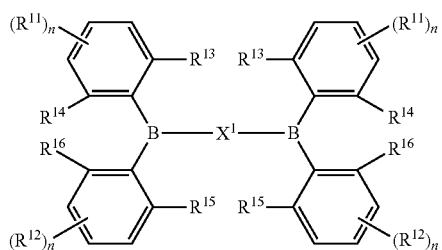

In the formula, $R^{11}$ and $R^{12}$ are each independently at least one of hydrogen atom, an alkyl group, an optionally substituted aryl group, a substituted silyl group, an optionally substituted nitrogen-containing heterocycle group or cyano group, $R^{13}$ to $R^{16}$ are each independently an optionally substituted alkyl group or an optionally substituted aryl group, $X^1$ is an optionally substituted arylene group with a carbon number of 20 or less, and ns are each independently an integer of 0 to 3.

(E-4-3-1)

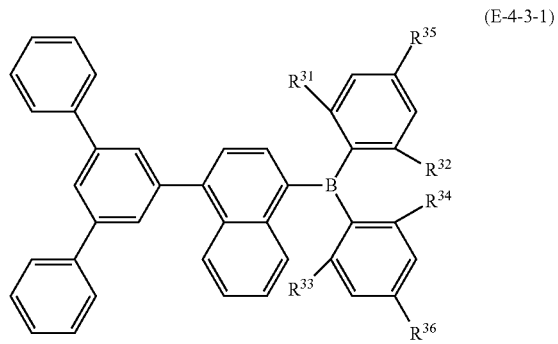

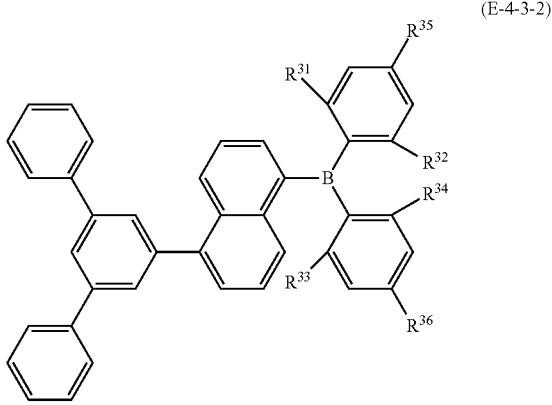

(E-4-3-2)

In each formula, $R^{31}$ to $R^{34}$ are each independently any of methyl, isopropyl or phenyl, and $R^{35}$ and $R^{36}$ are each independently any of hydrogen, methyl, isopropyl or phenyl.

The benzimidazole derivatives are compounds represented by the following formula (E-5).

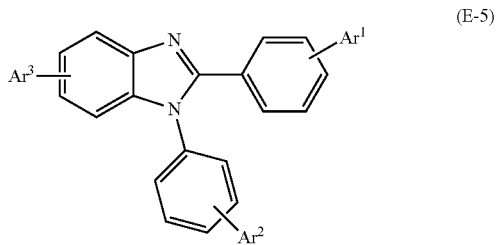

(E-5)

In the formula, $Ar^1$ to $Ar^3$ are each independently hydrogen or an optionally substituted aryl with a carbon number of 6 to 30. Especially, the benzimidazole derivatives wherein $Ar^1$ is an optionally substituted anthryl are preferable.

Specific examples of the aryl with a carbon number of 6 to 30 include phenyl, 1-naphthyl, 2-naphthyl, acenaphthylen-1-yl, acenaphthylen-3-yl, acenaphthylen-4-yl, acenaphthylen-5-yl, fluoren-1-yl, fluoren-2-yl, fluoren-3-yl, fluoren-4-yl, fluoren-9-yl, phenalen-1-yl, phenalen-2-yl, 1-phenanthryl, 2-phenanthryl, 3-phenanthryl, 4-phenanthryl, 9-phenanthryl, 1-anthryl, 2-anthryl, 9-anthryl, fluoranthen-1-yl, fluoranthen-2-yl, fluoranthen-3-yl, fluoranthen-7-yl, fluoranthen-8-yl, triphenylen-1-yl, triphenylen-2-yl, pyren-1-yl, pyren-2-yl, pyren-4-yl, chrysen-1-yl, chrysen-2-yl, chrysen-3-yl, chrysen-4-yl, chrysen-5-yl, chrysen-6-yl, naphthacen-1-yl, naphthacen-2-yl, naphthacen-5-yl, perylen-1-yl, perylen-2-yl, perylen-3-yl, pentacen-1-yl, pentacen-2-yl, pentacen-5-yl and pentacen-6-yl.

Specific examples of the benzimidazole derivatives include 1-phenyl-2-(4-(10-phenylanthracen-9-yl)phenyl)-1H-benzo[d]imidazole, 2-(4-(10-(naphthalen-2-yl)anthracen-9-yl)phenyl)-1-phenyl-1H-benzo[d]imidazole, 2-(3-(10-(naphthalen-2-yl)anthracen-9-yl)phenyl)-1-phenyl-1H-benzo[d]imidazole, 5-(10-(naphthalen-2-yl)anthracen-9-yl)-1,2-diphenyl-1H-benz o[d]imidazole, 1-(4-(10-(naphthalen-2-yl)anthracen-9-yl)phenyl)-2-phenyl-1H-benzo[d] imidazole, 2-(4-(9,10-di(naphthalen-2-yl)anthracen-2-yl) phenyl)-1-phenyl-1H-benzo[d]imidazole, 1-(4-(9,10-di (naphthalen-2-yl) anthracen-2-yl)phenyl)-2-phenyl-1H-benzo[d]imidazole, and 5-(9,10-di(naphthalen-2-yl) anthracen-2-yl)-1,2-diphenyl-1H-benzo[d]imidazole.

The electron transport layer or the electron injection layer may further contain a substance that can reduce the material that forms the electron transport layer or electron injection layer. As this reductive substance, various substances are used as long as they have certain reductivity, and at least one selected from, for example, alkali metals, alkaline earth metals, rare earth metals, oxides of alkali metals, halides of alkali metals, oxides of alkaline earth metals, halides of alkaline earth metals, oxides of rare earth metals, halides of rare earth metals, organic complexes of alkali metals, organic complexes of alkaline earth metals and organic complexes of rare earth metals can be preferably used.

Preferable reductive substances include alkali metals such as Na (work function: 2.36 eV), K (work function: 2.28 eV), Rb (work function: 2.16 eV) or Cs (work function: 1.95 eV), alkaline earth metals such as Ca (work function: 2.9 eV), Sr (work function: 2.0 to 2.5 eV) or Ba (work function: 2.52 eV), and those having a work function of 2.9 eV or less are especially preferable. Among these, more preferable reductive substances are alkali metals K, Rb or Cs, and Rb or Cs is further preferable, and Cs is the most preferable. These alkali metals especially have high reductivity, and by adding these to the material that forms the electron transport layer or electron injection layer in a relatively small amount, the luminance of the luminescent in an organic EL element is improved and the lifetime is extended. Furthermore, as the reductive substance having a work function of 2.9 eV or less, a combination of two or more kinds of these alkali metals is also preferable, and especially, combinations containing Cs such as a combination of Cs and Na, Cs and K, Cs and Rb or Cs and Na and K are preferable. Since the reductive substance contains Cs, the reducibility can be efficiently exerted, and the luminance of the luminescence in an organic EL element is improved and the lifetime is extended by adding to the material that forms the electron transport layer or the electron injection layer.

<Cathode in Organic Electroluminescent Element>

The cathode 108 plays a role in injecting electrons to the luminescent layer 105 through the electron injection layer 107 and the electron transport layer 106.

The material for forming the cathode 108 is not especially limited as long as it is a substance that can efficiently inject the electrons into the organic layer, similar materials to the material that forms the anode 102 can be used. Among these, metals such as tin, indium, calcium, aluminum, silver, copper, nickel, chromium, gold, platinum, iron, zinc, lithium, sodium, potassium, cesium and magnesium or alloys thereof (magnesium-silver alloys, magnesium-indium alloys, aluminum-lithium alloys such as lithium fluoride/aluminum, and the like) and the like are preferable. In order to increase the electron injection efficiency to improve the element property, lithium, sodium, potassium, cesium, calcium, magnesium or alloys containing these metals having a low work function are effective. However, in many cases, these low work function metals are generally unstable in the air. In order to improve this point, for example, a process using an electrode having high stability by doping an organic layer with a trace amount of lithium, cesium or magnesium is known. As other dopants, inorganic salts such as lithium fluoride, cesium fluoride, lithium oxide and cesium oxide can also be used. However the dopants are not limited to these.

Furthermore, in order to protect the electrodes, preferable examples include laminating metals such as platinum, gold, silver, copper, iron, tin, aluminum and indium or alloys using these metals, inorganic substances such as silica, titania and silicon nitride, polyvinyl alcohol, vinyl chloride, hydrocarbon-based polymer compounds and the like. The processes for preparing these electrodes are not especially limited as long as conduction can be obtained, and include resistance heating, electron ray beam, sputtering, ion plating and coating, and the like.

<Binder that May be Used in Respective Layers>

The above-mentioned materials that are used for the hole injection layer, hole transport layer, luminescent layer, electron transport layer and electron injection layer can form the respective layers by themselves, but can also be used by dispersing in a polymer binder, including solvent-soluble resins such as polyvinyl chloride, polycarbonate, polystyrene, poly(N-vinyl carbazole), polymethyl methacrylate, polybutyl methacrylate, polyester, polysulfone, polyphenylene oxide, polybutadiene, hydrocarbon resins, ketone resins, phenoxy resins, polyamide, ethyl cellulose, vinyl acetate resins, ABS resins and polyurethane resins, curable resins such as phenolic resins, xylene resins, petroleum resins, urea resins, melamine resins, unsaturated polyester resins, alkid resins, epoxy resins and silicone resins.

<Method for Preparing Organic Electroluminescent Element>

The respective layers that constitute the organic electroluminescent element can be formed by forming the materials that should constitute the respective layers into thin films by a process such as a deposition process, resistance heating deposition, electron beam deposition, sputtering, a molecular lamination process, a printing process, a spin coating process or a casting process, a coating process, and the like. The film thickness of each layer formed by this way is not especially limited and can be suitably preset according to the property of the material, but is generally in the range of 2 nm to 5000 nm. The film thickness can be generally measured by a quartz crystal oscillator film thickness meter or the like. In the case when a thin film is formed by using a deposition process, the deposition conditions thereof differ depending on the kind of the material, the intended crystal structure and associated structure of the film, and the like. It is preferable that the deposition conditions are suitably preset generally in the ranges of a boat heating temperature of 50 to 400° C., a vacuum degree of $10^{-6}$ to $10^{-3}$ Pa, a deposition velocity of 0.01 to 50 nm/sec, a substrate temperature of −150 to +300° C., a film thickness of 2 nm to 5 μm.

Next, as an example of the process for preparing the organic electroluminescent element, a process for preparing an organic electroluminescent element formed of an anode/a hole injection layer/a hole transport layer/a luminescent layer formed of a host material and a dopant material/an electron transport layer/an electron injection layer/a cathode will be explained. A thin film of an anode material is formed on a suitable substrate by a deposition process or the like to thereby form an anode, and thin films of a hole injection layer and a hole transport layer are formed on this anode. A host material and a dopant material are co-deposited thereon to form a thin film to thereby give a luminescent layer, and an electron transport layer and an electron injection layer are formed on this luminescent layer, and a thin film formed of a substance for a cathode is further formed by a deposition process or the like to give a cathode, thereby the intended organic electroluminescent element can be obtained. In the preparation of the above-mentioned organic electroluminescent element, it is also possible to reverse the order of preparation to prepare the cathode, electron injection layer, electron transport layer, luminescent layer, hole transport layer, hole injection layer and anode in this order.

In the case when a direct current voltage is applied to the organic electroluminescent element obtained in such way, it is sufficient to apply so that the anode has polarity of + and the cathode has polarity of −, and when a voltage of about 2 to 40 V is applied, luminescence can be observed from the side of the transparent or translucent electrode (the anode or cathode, and both). Furthermore, this organic electroluminescent element emits light also in the case when a pulse electrical current or an alternate current is applied. The wave form of the applied current may be arbitrary.

<Example of Application of Organic Electroluminescent Element>

Furthermore, the present invention can also be applied to a display device equipped with an organic electroluminescent element or a lighting device equipped with an organic electroluminescent element.

The display device or the lighting device equipped with the organic electroluminescent element can be produced by a known process such as connecting the organic electroluminescent element according to this exemplary embodiment to a known driving apparatus, and can be driven by suitably using a known driving process such as direct current driving, pulse driving and alternate current driving.

Examples of the display device include panel displays such as color flat panel displays, flexible displays such as flexible color organic electroluminescent (EL) displays, and the like (for example, see JP 10-335066A, JP2003-321546A, JP2004-281086 A and the like). Furthermore, examples of the display formats of the displays may include matrix and/or segment system (s) and the like. Matrix display and segment display may be present in a same panel.

A matrix refers to pixels for display that are two-dimensionally disposed in a grid form, a mosaic form or the like, and letters and images are displayed by an assembly of pixels. The shape and size of the pixels are determined depending on the intended use. For example, square pixels wherein each side is 300 μm or less are generally used for displaying images and letters on personal computers, monitors and television sets, and pixels wherein each side is in the order of millimeters are used in the cases of large-sized displays such as display panels. In the case of monochrome display, it is sufficient to align pixels of a same color, whereas in the case of color display, the display is conducted by aligning pixels of red, green and blue. In this case, a delta type and a stripe type are typically exemplified. Furthermore, the process for driving this matrix may be a line sequential driving process or an active matrix. The line sequential driving process has an advantage that the structure is easy, but in the case when the operation property is taken into consideration, the active matrix is more excellent in some cases. Therefore, it is necessary to use the process depending on the intended use.

In a segment format (type), a pattern is formed so that information that has been determined in advance is displayed, and fixed regions are allowed to emit light. Examples include display of time and temperature in digital clocks and thermometers, display of the operation state on audio devices, electromagnetic cookers and the like, and display on panels of automobiles, and the like.

Examples of the lighting device include lighting devices such as indoor lighting devices, backlights for liquid crystal display devices, and the like (for example, see JP 2003-257621 A, JP 2003-277741 A, JP 2004-119211 A and the like). Backlights are mainly used for the purpose of improving the visibility of display devices that do not emit light by themselves, and are used in liquid crystal display devices, clocks, audio apparatuses, automobile panels, display plates and signs, and the like. Especially, as a backlight for use in a liquid crystal display device, especially a personal computer for which thinning is a problem, a backlight using the luminescent element according to this exemplary embodiment is characterized by its thin shape and light weight, considering that a backlight of a conventional system is difficult to be formed into a thin shape since it includes a fluorescent light and a light guiding plate.

EXAMPLES

Hereinbelow, the present invention will be explained in more detail based on Examples. First, examples of synthesis of anthracene derivatives used in Examples will be explained hereinbelow.

Synthetic Example of Compound Represented by Formula (1-34)

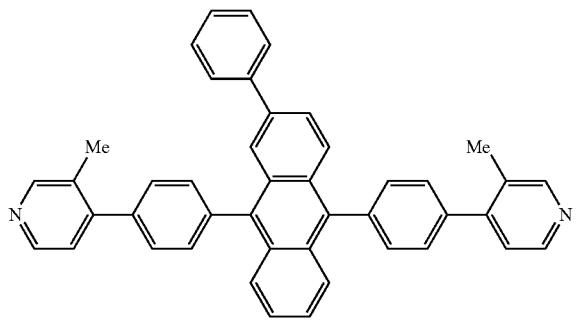

(1-34)

Synthesis of 4-(4-bromophenyl)-3-methylpyridine

A flask containing 4-bromo-3-methylpyridine hydrochloride (30.0 g) and THF (80 ml) was cooled with a dry ice-methanol bath, and a 2M isopropylmagnesium chloride THF solution (79.0 ml) was added dropwise to this solution. After completion of addition, a temperature was gradually raised to around 0° C., and the mixture was cooled again with an ice bath. A 2M isopropylmagnesium chloride THF solution (79.0 ml) was added dropwise thereto and, after completion of addition, the mixture was further stirred at room temperature for 2 hours. Then, the mixture was cooled again with an ice bath, zinc chloride tetramethylethylenediamine (40.0 g) was added and, thereafter, the mixture was stirred at room temperature for 30 minutes. To this solution were added 1-bromo-4-iodobenzene (44.8 g) and Pd(PPh$_3$)$_4$ (5.0 g), and the mixture was stirred at a refluxing temperature for 2 hours and 30 minutes. After the reaction solution was cooled to room temperature, a solution obtained by dissolving ethylenediaminetetraacetic acid tetrasodium salt dihydrate corresponding to approximately 3-fold moles relative to an objective compound in an appropriate amount of water (hereinbelow, abbreviated as EDTA.4Na aqueous solution) and ethyl acetate were added, and the layers were separated. After the solvent was distilled off under reduced pressure, the resulting solid was purified by silica gel column chromatography (developer: toluene/ethyl acetate=3/1 (volumetric ratio)). After the solvent was distilled off under reduced pressure, distillation under reduced pressure (135° C.) was performed to obtain 4-(4-bromophenyl)-3-methylpyridine (18.7 g).

Synthesis of 4,4'-((2-phenylanthracen-9,10-diyl)bis (4,1-phenylene))bis(3-methylpyridine)

9,10-Bis(4,4,5,5-tetramethyl-1,3,2-dioxaborolanyl)-2-phenylanthracene (5.0 g), 4-(4-bromophenyl)-3-methylpyridine (5.9 g), Pd(PPh$_3$)$_4$ (0.6 g), tripotassium phosphate (8.4 g), 1,2,4-trimethylbenzene (33 ml), t-butyl alcohol (6.6 ml) and water (1.3 ml) were placed into a flask, and the mixture was stirred at a refluxing temperature for 8 hours under the nitrogen atmosphere. After completion of heating, the reaction solution was cooled to room temperature, water was added to dissolve the inorganic salt, and an objective crude product was taken by suction filtration. The resulting solid was purified by NH-modified silica gel (DM1020: manufactured by Fuji Silysia Chemical Ltd.) column chromatography (developer: toluene), and purified by active carbon column chromatography (developer: toluene). Further recrystallization from toluene afforded a compound represented by the formula (1-34) "4,4'-((2-phenylanthracen-9,10-diyl)bis(4,1-phenylene))bis(3-methylpyridine)" (1.5 g).

A structure of the objective compound (1-34) was confirmed by NMR measurement.

$^1$H-NMR (CDC$_3$): δ=8.61 (d, 2H), 8.58 (m, 2H), 7.95 (m, 1H), 7.86 (d, 1H), 7.78 (m, 2H), 7.69 (dd, 1H), 7.58-7.64 (m, 10H), 7.31-7.46 (m, 7H), 2.50 (s, 3H), 2.48 (s, 3H).

A glass transition temperature (Tg) of the objective compound (1-34) was 114.3° C.
[Measuring equipment: Diamond DSC (manufactured by PERKIN-ELMER); measuring condition: cooling rate 200° C./Min., temperature raising rate 10° C./Min.]

In addition, measurement of a glass transition temperature of compounds thereafter was performed under the same condition in all cases.

Synthetic Example of Compound Represented by Formula (1-51)

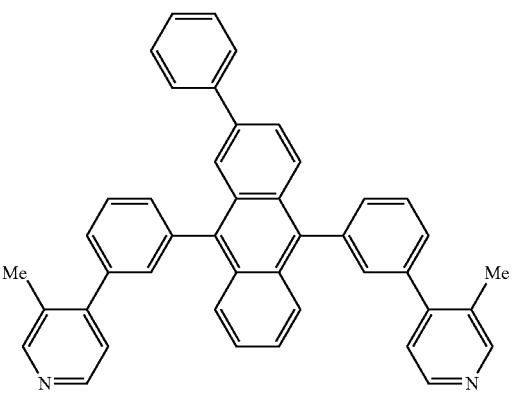

(1-51)

Synthesis of 4-(3-bromophenyl)-3-methylpyridine

A flask containing 4-bromo-3-methylpyridine hydrochloride (20.0 g) and THF (70 ml) was cooled with a dry ice-methanol bath, and a 2M isopropylmagnesium chloride THF solution (53.0 ml) was added dropwise to this solution.

After completion of addition, a temperature was gradually raised to around 0° C., and the mixture was cooled again with an ice bath. A 2M isopropylmagnesium chloride THF solution (53.0 ml) was added dropwise thereto and, after completion of addition, the mixture was further stirred at room temperature for 2 hours. Then, the mixture was cooled again with an ice bath, zinc chloride tetramethylethylenediamine (26.6 g) was added and, thereafter, the mixture was stirred at room temperature for 30 minutes. To this solution were added 1-bromo-3-iodobenzene (29.9 g) and Pd(PPh$_3$)$_4$ (3.3 g), and the mixture was stirred at a refluxing temperature for 2 hours. After the reaction solution was cooled to room temperature, an EDTA.4Na aqueous solution and ethyl acetate were added, and the layers were separated. After the solvent was distilled off under reduced pressure, the resulting solid was purified by silica gel column chromatography (developer: toluene/ethyl acetate=5/1 (volumetric ratio)), and further purified by active carbon column chromatography (developer: toluene) to obtain 4-(3-bromophenyl)-3-methylpyridine (5.0 g).

Synthesis of 4,4'-((2-phenylanthracen-9,10-diyl)bis (3,1-phenylene))bis(3-methylpyridine)

9,10-Bis(4,4,5,5-tetramethyl-1,3,2-dioxaborolanyl)-2-phenylanthracene (2.5 g), 4-(3-bromophenyl)-3-methylpyridine (2.9 g), Pd(PPh$_3$)$_4$ (0.3 g), tripotassium phosphate (4.2 g), 1,2,4-trimethylbenzene (16 ml), t-butyl alcohol (3 ml) and water (1 ml) were placed into a flask, and the mixture was stirred at a refluxing temperature for 5 hours under the nitrogen atmosphere. After completion of heating, the reaction solution was cooled to room temperature, water and toluene were added, and the layers were separated. Then, the reaction mixture was purified by NH-modified silica gel (DM1020: manufactured by Fuji Silysia Chemical Ltd.) column chromatography (developer: toluene), and further recrystallized from toluene to obtain a compound represented by the formula (1-51) "4,4'-((2-phenylanthracen-9, 10-diyl)bis(3,1-phenylene))bis(3-methylpyridine)" (0.3 g).

A structure of the objective compound (1-51) was confirmed by NMR measurement.

$^1$H-NMR(CDC$_3$): δ=8.47-8.55 (m, 4H), 7.95 (m, 1H), 7.84 (d, 1H), 7.70-7.79 (m, 4H), 7.66 (dd, 1H), 7.47-7.61 (m, 8H), 7.27-7.43 (m, 7H), 2.42 (d, 3H), 2.38 (d, 3H).

A glass transition temperature (Tg) of the objective compound (1-51) was 105.1° C.

Synthetic Example of Compound Represented by Formula (1-38)

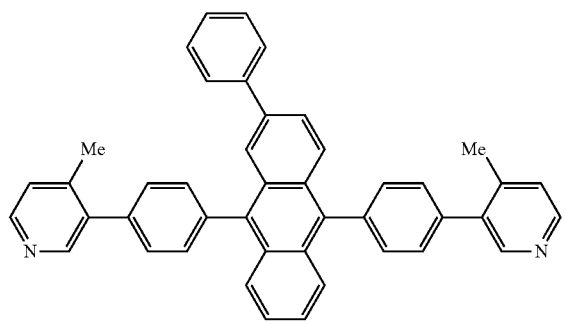

(1-38)

Synthesis of 4-methyl-3-(4,4,5,5-tetramethyl-1,3,2-dioxaborolan-2-yl)pyridine

3-Bromo-4-methyopyridine (50.0 g), bispinacolatodiboron (73.9 g), PdCl$_2$(dppf) (4.8 g), potassium acetate (85.7 g) and anisole (800 ml) were placed in a flask, and the mixture was stirred at a refluxing temperature for 3 hours under the nitrogen atmosphere. After completion of heating, the reaction solution was cooled to room temperature, anisole was distilled off under reduced pressure, toluene was added, and the precipitated inorganic salt was removed by suction filtration. After this filtrate was further passed through active carbon, the solvent was distilled off to obtain 4-methyl-3-(4,4,5,5-tetramethyl-1,3,2-dioxaborolan-2-yl)pyridine quantitatively.

Synthesis of 3-(4-bromophenyl)-4-methylpyridine

4-Methyl-3-(4,4,5,5-tetramethyl-1,3,2-dioxaborolan-2-yl)pyridine (62.6 g), p-dibromobenzene (68.6 g), Pd(PPh$_3$)$_4$ (6.7 g), potassium phosphate (123.0 g) and N-methylpyrrolidone (1000 ml) were placed into a flask, and the mixture was stirred at 120° C. for 1 hour under the nitrogen atmosphere. The reaction solution was cooled to room temperature, N-methylpyrrolidone was distilled off under reduced pressure, toluene was added, and the precipitated inorganic salt was removed by suction filtration. Further, the reaction mixture was purified by silica gel column chromatography (developer: toluene/ethyl acetate=1/1 (volumetric ratio)) to obtain 3-(4-bromophenyl)-4-methylpyridine (17.1 g).

Synthesis of 3,3'-((2-phenylanthracen-9,10-diyl)bis (4,1-phenylene))bis(4-methylpyridine)

9,10-Bis(4,4,5,5-tetramethyl-1,3,2-dioxaborolanyl)-2-phenylanthracene (3.4 g), 3-(4-bromophenyl)-4-methylpyridine (4.0 g), Pd(PPh$_3$)$_4$ (0.04 g), tripotassium phosphate (5.8 g), 1,2,4-trimethylbenzene (20 ml), t-butyl alcohol (4 ml) and water (0.8 ml) were placed into a flask, and the mixture was stirred at a refluxing temperature for 3 hours under the nitrogen atmosphere. After completion of heating, the reaction solution was cooled to room temperature, water and toluene were added, and the layers were separated, followed by purification by silica gel column chromatography (developer: toluene/ethyl acetate mixed solvent). Thereupon, by reference to the method described in "Guideline of Organic Chemical Experiment (1)—Substance Handling Method and Separation Purification Method-" published by Kagakudojin Co., page 94, a ratio of ethyl acetate in a developer was gradually increased to elute an objective substance. The solid obtained by distilling the solvent off under reduced pressure was washed with ethyl acetate, and recrystallized from toluene to obtain a compound represented by the formula (1-38) "3,3'-((2-phenylanthracen-9,10-diyl)bis(4,1-phenylene))bis(4-methylpyridine)" (2.2 g).

A structure of the objective compound (1-38) was confirmed by NMR measurement.

$^1$H-NMR (CDC$_3$): δ=8.67 (m, 2H), 8.53 (m, 2H), 7.97 (m, 1H), 7.88 (d, 1H), 7.81 (m, 2H), 7.69 (dd, 1H), 7.57-7.65 (m, 10H), 7.39-7.45 (m, 4H), 7.34 (t, 1H), 7.24-7.30 (m, 2H), 2.50 (s, 3H), 2.48 (s, 3H).

A glass transition temperature (Tg) of the objective compound (1-38) was 110.9° C.

Synthetic Example of Compound Represented by Formula (1-39)

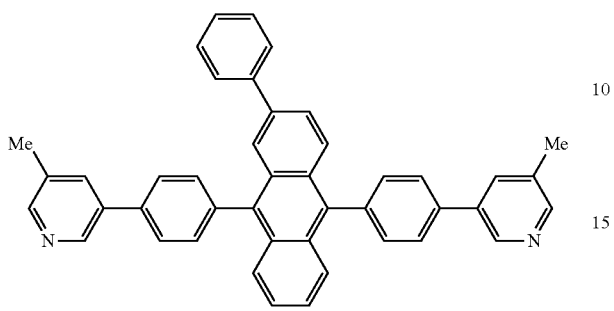
(1-39)

Synthesis of 3-methyl-5-(4,4,5,5-tetramethyl-1,3,2-dioxaborolan-2-yl)

3-Bromo-5-methylpyridine (50.0 g), bispinacolatodiboron (73.9 g), PdCl$_2$(dppf) (4.8 g), potassium acetate (85.7 g) and anisole (800 ml) were placed into a flask, and the mixture was stirred at a refluxing temperature for 3 hours under the nitrogen atmosphere. After completion of heating, the reaction solution was cooled to room temperature, anisole was distilled off under reduced pressure, toluene was added, and the precipitated inorganic salt was removed by suction filtration. After this filtrate was further passed through active carbon, the solvent was distilled off to obtain 3-methyl-5-(4,4,5,5-tetramethyl-1,3,2-dioxaborolan-2-yl) pyridine (60.0 g).

Synthesis of 3-(4-bromophenyl)-5-methylpyridine

3-Methyl-5-(4,4,5,5-tetramethyl-1,3,2-dioxaborolan-2-yl)pyridine (60.0 g), p-dibromobenzene (70.0 g), Pd(PPh$_3$)$_4$ (6.7 g), potassium phosphate (123.0 g) and N-methylpyrrolidone (1000 ml) were placed into a flask, and the mixture was stirred at 120° C. for 1 hour under the nitrogen atmosphere. The reaction solution was cooled to room temperature, N-methylpyrrolidone was distilled off under reduced pressure, toluene was added, and the precipitated inorganic salt was removed by suction filtration. The reaction mixture was further purified by silica gel column chromatography (developer: toluene/ethyl acetate=1:1 (volumetric ratio)) to obtain 3-(4-bromophenyl)-5-methylpyridine (30.9 g).

Synthesis of 5,5'-((2-phenylanthracen-9,10-diyl)bis(4,1-phenylene))bis(3-methylpyridine)

9,10-Bis(4,4,5,5-tetramethyl-1,3,2-dioxaborolanyl)-2-phenylanthracene (3.4 g), 3-(4-bromophenyl)-4-methylpyridine (4.0 g), Pd(PPh$_3$)$_4$ (0.04 g), tripotassium phosphate (5.8 g), 1,2,4-trimethylbenzene (20 ml), t-butyl alcohol (4 ml) and water (0.8 ml) were placed into a flask, and the mixture was stirred at a refluxing temperature for 3 hours under the nitrogen atmosphere. After completion of heating, the reaction solution was cooled to room temperature, water and toluene were added, and the layers were separated. The solvent was distilled off under reduced pressure, and the resulting solid was washed with a toluene/methanol mixed solvent, and recrystallized from o-dichlorobenzene to obtain a compound represented by the formula (1-39) "5,5'-((2-phenylanthracen-9,10-diyl)bis(4,1-phenylene))bis(3-methylpyridine)" (1.0 g).

A structure of the objective compound (1-39) was confirmed by NMR measurement.

$^1$H-NMR (CDC$_3$): δ=8.86 (m, 2H), 8.51 (m, 2H), 7.96 (m, 1H), 7.83-7.90 (m, 7H), 7.75-7.80 (m, 2H), 7.61-7.68 (m, 5H), 7.57 (d, 2H), 7.36-7.43 (m, 4H), 7.32 (t, 1H), 2.49 (s, 3H), 2.48 (s, 3H).

A glass transition temperature (Tg) of the objective compound (1-39) was 116.6° C.

Synthetic Example of Compound Represented by Formula (1-41)

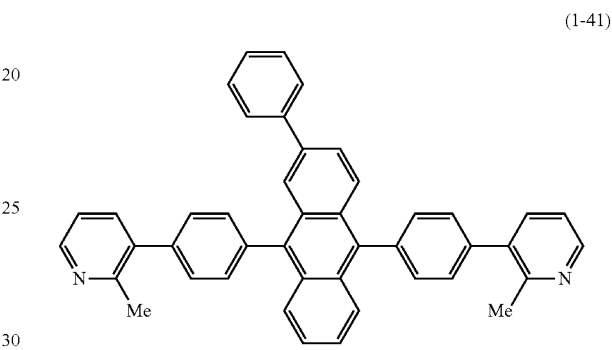
(1-41)

Synthesis of 2-methyl-3-(4,4,5,5-tetramethyl-1,3,2-dioxaborolan-2-yl)pyridine 3-Bromo-2-methylpyridine (100.0 g), bispinacolatodiboron (171.1 g), PdCl$_2$(dppf) (9.5 g), potassium acetate (171.2 g) and cyclopentyl methyl ether (1600 ml) were placed into a flask, and the mixture was stirred at a refluxing temperature for 6 hours and 30 minutes under the nitrogen atmosphere. After completion of heating, the reaction solution was cooled to room temperature, and the inorganic salt was removed by suction filtration. After this filtrate was further passed through active carbon, the solvent was distilled off to obtain 2-methyl-3-(4,4,5,5-tetramethyl-1,3,2-dioxaborolan-2-yl)pyridine (120.0 g).

Synthesis of 3-(4-bromophenyl)-2-methylpyridine

2-Methyl-3-(4,4,5,5-tetramethyl-1,3,2-dioxaborolan-2-yl)pyridine (70.0 g), p-dibromobenzene (113.4 g), Pd(PPh$_3$)$_4$ (16.7 g), potassium phosphate (123.0 g) and N-methylpyrroridone (1000 ml) were placed into a flask, and the mixture was stirred at 120° C. for 1 hour under the nitrogen atmosphere. The reaction solution was cooled to room temperature, N-methylpyrroridone was distilled off under reduced pressure, toluene was added, and the precipitated inorganic salt was removed by suction filtration. Further purification by silica gel column chromatography (developer: toluene/ethyl acetate=1/1 (volumetric ratio)) afforded 3-(4-bromophenyl)-2-methylpyridine (51.0 g).

Synthesis of 3,3'-((2-phenylanthracen-9,10-diyl)bis(4,1-phenylene))bis(2-methylpyridine)

9,10-Bis(4,4,5,5-tetramethyl-1,3,2-dioxaborolanyl)-2-phenylanthracene (3.4 g), 3-(4-bromophenyl)-2-methylpyridine (4.0 g), Pd(PPh$_3$)$_4$ (0.08 g), tripotassium phosphate (5.8 g), 1,2,4-trimethylbenzene (20 ml), t-butyl alcohol (4 ml) and water (0.8 ml) were placed into a flask, and the mixture was stirred at a refluxing temperature for 3 hours under the nitrogen atmosphere. After completion of heating, the reaction solution was cooled to room temperature, and suction-filtered with a Hirsch funnel paved with Celite. The solvent was distilled off under reduced pressure, followed by purification by silica gel column chromatography (developer: toluene/ethyl acetate). Thereupon, a ratio of ethyl acetate in a developer was gradually increased to elute an objective substance. Further recrystallization from toluene afforded a compound represented by the formula (1-41) "3,3'-((2-phenylanthracen-9,10-diyl)bis(4,1-phenylene))bis(2-methylpyridine)" (0.2 g).

A structure of the objective compound (1-41) was confirmed by NMR measurement.

$^1$H-NMR (CDC$_3$): δ=8.59 (m, 2H), 7.97 (m, 1H), 7.84 (d, 1H), 7.81 (m, 2H), 7.75 (d, 2H), 7.69 (dd, 1H), 7.57-7.64 (m, 10H), 7.39-7.45 (m, 4H), 7.34 (t, 1H), 7.28 (m, 2H), 2.73 (s, 3H), 2.71 (s, 3H).

A glass transition temperature (Tg) of the objective compound (1-41) was 107.3° C.

Synthetic Example of Compound Represented by Formula (1-40)

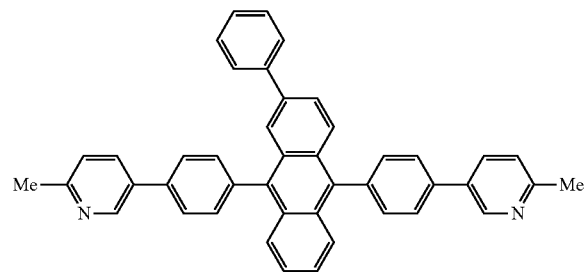

(1-40)

Synthesis of 5,5'-((2-phenylanthracen-9,10-diyl)bis (4,1-phenylene))bis(2-methylpyridine)

9,10-Bis(4,4,5,5-tetramethyl-1,3,2-dioxaborolanyl)-2-phenylanthracene (8.3 g), 5-(4-chlorophenyl)-2-methylpyridine (manufactured by Rieke) (8.0 g), bis(dibenzylideneacetone) palladium (0) (Pd(dba)$_2$) (1.1 g), 2-dicyclohexylphosphino-2',6'-dimethoxybiphenyl (Sphos, manufactured by Aldrich) (1.9 g), tripotassium phosphate (33.4 g), 1,2,4-trimethylbenzene (40 ml), t-butyl alcohol (8 ml) and water (1.6 ml) were placed into a flask, and the mixture was stirred at a refluxing temperature for 1 hour under the nitrogen atmosphere. After completion of heating, the reaction solution was cooled to room temperature, water was added, and the precipitate was taken by suction filtration. The resulting solid was washed with water and, then, ethanol, and recrystallized from chlorobenzene to obtain a compound represented by the formula (1-40) "5,5'-((2-phenylanthracen-9,10-diyl)bis(4,1-phenylene))bis(2-methylpyridine)" (4.3 g).

A structure of the objective compound (1-40) was confirmed by NMR measurement.

$^1$H-NMR (CDC$_3$): δ=8.94 (m, 2H), 7.98 (m, 3H), 7.82-7.87 (m, 5H), 7.79 (m, 2H), 7.61-7.66 (m, 5H), 7.58 (d, 2H), 7.37-7.43 (m, 4H), 7.32 (m, 3H), 2.67 (m, 6H).

A glass transition temperature (Tg) of the objective compound (1-40) was 128.0° C.

Synthetic Example of Compound Represented by Formula (1-35)

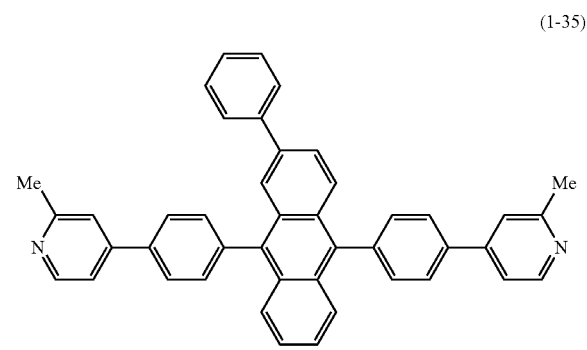 [SMILES: Cc1cc(-c2ccc(-c3c4ccccc4c(-c4ccc(-c5ccnc(C)c5)cc4)c4cc(-c5ccccc5)ccc34)cc2)ccn1]

(1-35)

Synthesis of 2-methyl-4-(4,4,5,5-tetramethyl-1,3,2-dioxaborolan-2-yl)pyridine

4-Bromo-2-methylpyridine (24.8 g), bispinacolatodiboron (36.8 g), PdCl$_2$(dppf) (2.5 g), potassium acetate (42.8 g) and cyclopentyl methyl ether (400 ml) were placed into a flask, and the mixture was stirred at a refluxing temperature for 5 hours under the nitrogen atmosphere. After completion of heating, the reaction solution was cooled to room temperature, and the inorganic salt was removed by suction filtration. The solvent of the filtrate was distilled off, followed by purification by active carbon column chromatography (developer: toluene) to obtain 2-methyl-4-(4,4,5,5-tetramethyl-1,3,2-dioxaborolan-2-yl)pyridine (31.4 g).

Synthesis of 4-(4-bromophenyl)-2-methylpyridine

2-Methyl-4-(4,4,5,5-tetramethyl-1,3,2-dioxaborolan-2-yl)pyridine (9.4 g), 1-bromo-4-iodobenzene (12.2 g), Pd(PPh$_3$)$_4$ (0.9 g), potassium phosphate (18.8 g) and N-methylpyrrolidone (190 ml) were placed in a flask, and the mixture was stirred at a refluxing temperature for 7 hours under the nitrogen atmosphere. The reaction solution was cooled to room temperature, water and toluene were added, the layers were separated, and the solvent of the organic layer was distilled off under reduced pressure. The resulting crude product was purified by silica gel column chromatography (developer: toluene/ethyl acetate) to obtain 4-(4-bromophenyl)-2-methylpyridine (5.9 g). Thereupon, a ratio of ethyl acetate in a developer was gradually increased to elute an objective substance.

Synthesis of 4,4'-((2-phenylanthracen-9,10-diyl)bis (4,1-phenylene))bis(2-methylpyridine)

9,10-Bis(4,4,5,5-tetramethyl-1,3,2-dioxaborolanyl)-2-phenylanthracene (2.0 g), 4-(4-bromophenyl)-2-methylpyridine (2.2 g), Pd(PPh$_3$)$_4$ (0.2 g), tripotassium phosphate (3.4 g), 1,2,4-trimethylbenzene (12 ml), t-butyl alcohol (2.4 ml) and water (0.5 ml) were placed into a flask, and the mixture was stirred at a refluxing temperature for 11 hours under the nitrogen atmosphere. After completion of heating, the reaction solution was cooled to room temperature, an EDTA.4Na aqueous solution was added to dissolve the inorganic salt, and the solid containing an objective substance was taken by suction filtration. Then, this solid was purified by NH-modified silica gel (DM1020: manufactured by Fuji Silysia Chemical Ltd.) column chromatography (developer: chlorobenzene), and recrystallized from chlorobenzene to obtain a compound represented by the formula (1-35) "4,4'-((2-phenylanthracen-9,10-diyl)bis(4,1-phenylene))bis(2-methylpyridine)" (0.2 g).

A structure of the objective compound (1-35) was confirmed by NMR measurement.

$^1$H-NMR (CDC$_3$): δ=8.64 (m, 2H), 7.92 (m, 5H), 7.84 (d, 1H), 7.75 (m, 2H), 7.65 (m, 5H), 7.57 (m, 4H), 7.51 (d, 2H), 7.36-7.43 (m, 4H), 7.33 (t, 1H), 2.70 (m, 6H).

A glass transition temperature (Tg) of the objective compound (1-35) was 119.9° C.

Synthetic Example of Compound Represented by Formula (1-50)

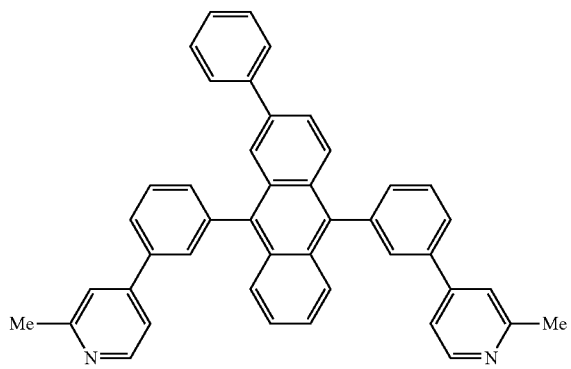

(1-50)

Synthesis of 4-(3-bromophenyl)-2-methylpyridine

2-Methyl-4-(4,4,5,5-tetramethyl-1,3,2-dioxaborolan-2-yl)pyridine (10.0 g), 1-bromo-4-iodobenzene (13.0 g), Pd(PPh$_3$)$_4$ (1.0 g), potassium phosphate (20.0 g) and N-methylpyrrolidone (200 ml) were placed into a flask, and the mixture was stirred at a refluxing temperature for 4 hours and 30 minutes under the nitrogen atmosphere. After the reaction solution was cooled to room temperature, an EDTA.4Na aqueous solution and toluene were added, the layers were separated, and the solvent of the organic layer was distilled off under reduced pressure. The resulting crude product was purified by NH-modified silica gel (DM1020: manufactured by Fuji Silysia Chemical Ltd.) column chromatography (developer: toluene/ethyl acetate) to obtain 4-(3-bromophenyl)-2-methylpyridine (5.8 g). Thereupon, a ratio of ethyl acetate in a developer was gradually increased to elute an objective substance.

Synthesis of 4,4'-((2-phenylanthracen-9,10-diyl)bis(3,1-phenylene))bis(2-methylpyridine)

9,10-Bis(4,4,5,5-tetramethyl-1,3,2-dioxaborolanyl)-2-phenylanthracene (2.5 g), 4-(3-bromophenyl)-2-methylpyridine (2.9 g), Pd(PPh$_3$)$_4$ (0.2 g), tripotassium phosphate (4.2 g), 1,2,4-trimethylbenzene (15 ml), t-butyl alcohol (3.0 ml) and water (0.6 ml) were placed into a flask, and the mixture was stirred at a refluxing temperature for 4 hours under the nitrogen atmosphere. After completion of heating, the reaction solution was cooled to room temperature, an EDTA.4Na aqueous solution and toluene were added, the layers were separated, and the solvent of the organic layer was distilled off under reduced pressure. The resulting oily substance was purified by NH-modified silica gel (DM1020: manufactured by Fuji Silysia Chemical Ltd.) column chromatography (developer: toluene/ethyl acetate) to obtain a compound represented by the formula (1-50) "4,4'-((2-phenylanthracen-9,10-diyl)bis(3,1-phenylene))bis(2-methylpyridine)" (0.8 g). Thereupon, a ratio of ethyl acetate in a developer was gradually increased to elute an objective substance.

A structure of the objective compound (1-50) was confirmed by NMR measurement.

$^1$H-NMR (CDC$_3$): δ=8.56 (t, 2H), 7.93 (m, 1H), 7.72-7.89 (m, 9H), 7.66 (dd, 1H), 7.62 (m, 2H), 7.55 (d, 2H), 7.48 (m, 2H), 7.36-7.45 (m, 6H), 7.32 (t, 1H), 2.62 (s, 3H), 2.61 (s, 3H).

A glass transition temperature (Tg) of the objective compound (1-50) was 102.5° C.

Synthetic Example of Compound Represented by Formula (1-6)

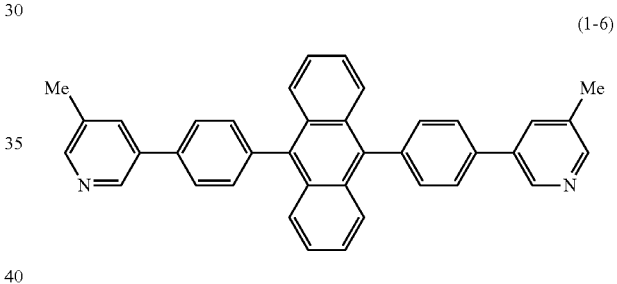

(1-6)

Synthesis of 3-methyl-5-(4-(4,4,5,5-tetramethyl-1,3,2-dioxaborolan-2-yl)phenyl)pyridine 3-(4-Bromophenyl)-5-methylpyridine (29.8 g), bispinacolatodiboron (36.6 g), PdCl$_2$(dppf) (2.9 g), potassium acetate (21.4 g) and cyclopentyl methyl ether (250 ml) were placed into a flask, and the mixture was stirred at a refluxing temperature for 15 hours under the nitrogen atmosphere. After the reaction solution was cooled to room temperature, water and toluene were added, and the layers were separated. The solid obtained by distilling the solvent off under reduced pressure was purified by active carbon column chromatography (developer: toluene) to obtain 3-methyl-5-(4-(4,4,5,5-tetramethyl-1,3,2-dioxaborolan-2-yl)phenyl) pyridine (31.2 g).

Synthesis of 9,10-bis(4-(5-methylpyridin-3-yl)phenyl) anthracene 9,10-Bromoanthracene (2.0 g), 3-methyl-5-(4-(4,4,5,5-tetramethyl-1,3,2-dioxaborolan-2-yl)phenyl)pyridine (4.2 g), Pd(PPh$_3$)$_4$ (0.2 g), tripotassium phosphate (5.0 g), toluene (17 ml), ethanol (4 ml) and water (2 ml) were placed into a flask, and the mixture was stirred at a refluxing temperature for 18 hours under the nitrogen atmosphere. After the reaction solution was cooled to room temperature, the solid which was precipitated by adding water was taken by suction filtration. The resulting solid was further washed with water, washed with methanol, dissolved in chlorobenzene, and purified by NH-modified silica gel (DM1020: manufactured by Fuji Silysia Chemical Ltd.) column chromatography (developer: toluene). The crude product was further purified by active carbon column chromatography (developer: chlorobenzene) to obtain a compound represented by the formula (1-6) "9,10-bis(4-(5-methylpyridin-3-yl)phenyl) anthracene" (0.8 g).

A structure of the objective compound (1-6) was confirmed by NMR measurement.

$^1$H-NMR (CDC$_3$): δ=8.61 (m, 2H), 8.23 (d, 4H), 7.99 (m, 1H), 7.87 (d, 1H), 7.75-7.83 (m, 4H), 7.61-7.67 (m, 7H), 7.57 (d, 2H), 7.33-7.41 (m, 4H), 7.30 (t, 1H), 2.43 (m, 6H).

Synthetic Example of Compound Represented by Formula (1-36)

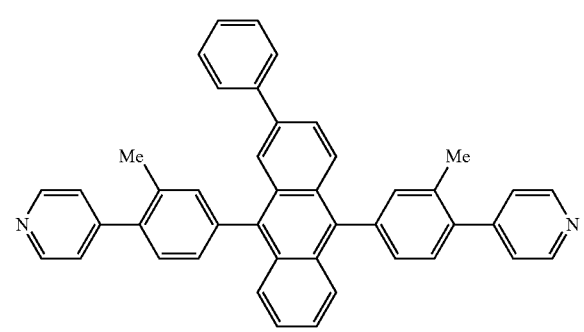

(1-36)

Synthesis of 4-(4-bromo-2-methylphenyl)pyridine

4-Pyridineboronic acid (4.0 g), 4-bromo-1-iodo-2-methylbenzene (11.6 g), Pd(PPh$_3$)$_4$ (1.1 g), potassium phosphate (13.8 g), toluene (65 ml), ethanol (15 ml) and water (3 ml) were placed into a flask, and the mixture was stirred at a refluxing temperature for 9 hours under the nitrogen atmosphere. After the reaction solution was cooled to room temperature, water and ethyl acetate were added, and the layers were separated. After the solvent was distilled off under reduced pressure, the resulting solid was purified by silica gel column chromatography (developer: toluene/ethyl acetate=3/1 (volumetric ratio)) to obtain 4-(4-bromo-2-methylphenyl)pyridine (6.5 g).

Synthesis of 4,4'-((2-phenylanthracen-9,10-diyl)bis(2-methyl-4,1-phenylene))dipyridine 9,10-Bis(4,4,5,5-tetramethyl-1,3,2-dioxaborolanyl)-2-phenylanthracene (2.5 g), 4-(4-bromo-2-methylphenyl)pyridine (2.9 g), Pd(PPh$_3$)$_4$ (0.2 g), tripotassium phosphate (4.2 g), 1,2,4-trimethylbenzene (14 ml), t-butyl alcohol (3 ml) and water (0.5 ml) were placed into a flask, and the mixture was stirred at a refluxing temperature for 5 hours under the nitrogen atmosphere. After completion of heating, water and toluene were added, the layers were separated, and the solid obtained by distilling the solvent off under reduced pressure was purified by NH-modified silica gel (DM1020: manufactured by Fuji Silysia Chemical Ltd.) column chromatography (developer: toluene). The crude product was further purified by active carbon column chromatography (developer: toluene), and recrystallized from a heptane/toluene mixed solvent to obtain a compound represented by the formula (1-36) "4,4'-((2-phenylanthracen-9,10-diyl)bis(2-methyl-4,1-phenyl ene))dipyridine" (0.5 g).

A structure of the objective compound (1-36) was confirmed by NMR measurement. $^1$H-NMR (CDC$_3$): δ=8.75 (m, 4H), 7.98 (m, 1H), 7.88 (d, 1H), 7.80 (m, 2H), 7.66 (dd, 1H), 7.60 (d, 2H), 7.38-7.50 (m, 14H), 7.36 (t, 1H), 2.44 (m, 6H).

A glass transition temperature (Tg) of the objective compound (1-36) was 145.0° C.

Synthetic Example of Compound Represented by Formula (1-44)

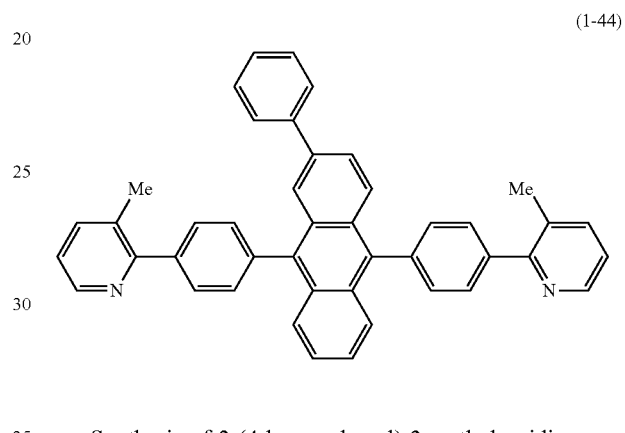

(1-44)

Synthesis of 2-(4-bromophenyl)-3-methylpyridine

A flask containing 2-bromo-3-methylpyridine (62.4 g) and THF (200 ml) was cooled with an ice bath, and a 2M isopropylmagnesium chloride THF solution (200.0 ml) was added dropwise to this solution. After completion of addition, a temperature was raised to a refluxing temperature, and the solution was stirred for 1 hour. Then, the solution was cooled again with an ice bath, zinc chloride tetramethylethylenediamine (110.0 g) was added and, thereafter, the solution was stirred at room temperature for 30 minutes. To this solution were added 1-bromo-4-iodobenzene (103.0 g) and Pd(PPh$_3$)$_4$ (4.2 g), and the solution was stirred at a refluxing temperature for 1 hour. After the reaction solution was cooled to room temperature, an EDTA.4Na aqueous solution and ethyl acetate were added, and the layers were separated. After the solvent was distilled off under reduced pressure, the resulting solid was purified by silica gel column chromatography (developer: toluene/ethyl acetate=9/1 (volumetric ratio)) to obtain 2-(4-bromophenyl)-3-methylpyridine (67.0 g).

Synthesis of 2,2'-((2-phenylanthracen-9,10-diyl)bis(4,1-phenylene))bis(3-methylpyridine)

9,10-Bis(4,4,5,5-tetramethyl-1,3,2-dioxaborolanyl)-2-phenylanthracene (3.5 g), 2-(4-bromophenyl)-3-methylpyridine (3.8 g), Pd(PPh$_3$)$_4$ (0.2 g), tripotassium phosphate (5.9 g), 1,2,4-trimethylbenzene (20 ml), t-butyl alcohol (5 ml) and water (1 ml) were placed into a flask, and the mixture was stirred at a refluxing temperature for 5 hours under the nitrogen atmosphere. After completion of heating, the reaction solution was cooled to room temperature, water and toluene were added, and the layers were separated. After the solvent was distilled off under reduced pressure, the resulting solid was purified by silica gel column chromatography (developer: toluene/ethyl acetate=9/1 (volumetric ratio)), and further recrystallized from a heptane/toluene mixed solvent to obtain a compound represented by the formula (1-44) "2,2'-((2-phenylanthracen-9,10-diyl)bis(4,1-phenylene))bis(3-methylpyridine)" (0.3 g).

A structure of the objective compound (1-44) was confirmed by NMR measurement.

$^1$H-NMR (CDC$_3$): δ=8.63 (m, 2H), 8.03 (m, 1H), 7.91 (d, 1H), 7.76-7.87 (m, 6H), 7.57-7.71 (m, 9H), 7.35-7.44 (m, 4H), 7.32 (t, 1H), 7.26 (m, 2H), 2.57 (s, 3H), 2.55 (s, 3H).

A glass transition temperature (Tg) of the objective compound (1-44) was 110.4° C.

Synthetic Example of Compound Represented by Formula (1-45)

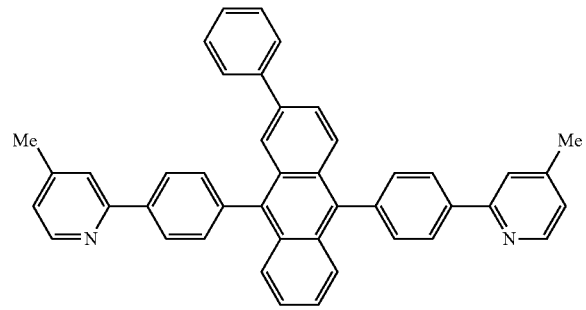

(1-45)

Synthesis of 2-(4-bromophenyl)-4-methylpyridine

A flask containing 2-bromo-4-methylpyridine (62.4 g) and THF (200 ml) was cooled with an ice bath, and a 2M isopropylmagnesium chloride THF solution (200.0 ml) was added dropwise to this solution. After completion of addition, a temperature was raised to room temperature, and the solution was stirred for 3 hours. Then, the solution was cooled again with an ice bath, zinc chloride tetramethylethylenediamine (110.0 g) was added and, thereafter, the solution was stirred at room temperature for 30 minutes. To this solution were added 1-bromo-4-iodobenzene (103.0 g) and Pd(PPh$_3$)$_4$ (4.2 g), and the solution was stirred at a refluxing temperature for 1 hour. After the reaction solution was cooled to room temperature, an EDTA.4Na aqueous solution and ethyl acetate were added, and the layers were separated. After the solvent was distilled off under reduced pressure, the resulting solid was purified by silica gel column chromatography (developer: toluene/ethyl acetate=9/1 (volumetric ratio)), and further recrystallized from heptane to obtain 2-(4-bromophenyl)-4-methylpyridine (56.5 g).

Synthesis of 2,2'-((2-phenylanthracen-9,10-diyl)bis(4,1-phenylene))bis(4-methylpyridine)

9,10-Bis(4,4,5,5-tetramethyl-1,3,2-dioxaborolanyl)-2-phenylanthracene (4.1 g), 2-(4-bromophenyl)-4-methylpyridine (4.4 g), Pd(PPh$_3$)$_4$ (0.3 g), tripotassium phosphate (6.8 g), 1,2,4-trimethylbenzene (20 ml), t-butyl alcohol (5 ml) and water (1 ml) were placed into a flask, and the mixture was stirred at a refluxing temperature for 7 hours and 30 minutes under the nitrogen atmosphere. After completion of heating, the reaction solution was cooled to room temperature, water and toluene were added, and the layers were separated. After the solvent was distilled off under reduced pressure, the resulting solid was purified by silica gel column chromatography (developer: toluene/ethyl acetate=9/1 (volumetric ratio)), and further recrystallized from toluene to obtain a compound represented by the formula (1-45) "2,2'-((2-phenylanthracen-9,10-diyl)bis(4,1-phenylene))bis(4-methylpyridine)" (2.2 g).

A structure of the objective compound (1-45) was confirmed by NMR measurement.

$^1$H-NMR (CDC$_3$): δ=8.63 (d, 2H), 8.24 (dd, 4H), 7.99 (m, 1H), 7.87 (d, 1H), 7.74-7.82 (m, 2H), 7.73 (s, 2H), 7.63 (m, 5H), 7.56 (d, 2H), 7.33-7.41 (m, 4H), 7.29 (t, 1H), 7.13 (m, 2H), 2.48 (m, 6H).

A glass transition temperature (Tg) of the objective compound (1-45) was 125.0° C.

Synthetic Example of Compound Represented by the Formula (1-151)

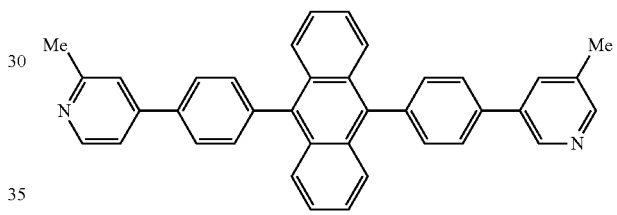

(1-151)

Synthesis of 3-(4-(anthracen-9-yl)phenyl)-5-methylpyridine

9-Bromoanthracene (10.3 g), 3-methyl-5-(4-(4,4,5,5-tetramethyl-1,3,2-dioxaborolan-2-yl)phenyl)pyridine (11.8 g), Pd(PPh$_3$)$_4$ (1.4 g), tripotassium phosphate (17.0 g), 1,2,4-trimethylbenzene (40 ml), t-butyl alcohol (10 ml) and water (2 ml) were placed into a flask, and the mixture was stirred at a refluxing temperature for 11 hours under the nitrogen atmosphere. After the reaction solution was cooled to room temperature, water and toluene were added, and the layers were separated. After the solvent was distilled off under reduced pressure, the resulting solid was purified by silica gel column chromatography (developer: toluene/ethyl acetate=4/1 (volumetric ratio)) to obtain 3-(4-(anthracen-9-yl)phenyl)-5-methylpyridine (10.5 g).

Synthesis of 3-(4-(10-bromoanthracen-9-yl)phenyl)-5-methylpyridine

A flask containing 3-(4-(anthracen-9-yl)phenyl)-5-methylpyridine (10.5 g), N-brominated succinic acid imide (6.4 g), iodine (0.05 g) and tetrahydrofuran (50 ml) was stirred at room temperature for 16 hours under the nitrogen atmosphere. An aqueous sodium thiosulfate solution was added to stop the reaction, the mixture was stirred for a little while, thereafter, toluene was added, and the layers were separated. After the solvent was distilled off under reduced pressure, the resulting solid was purified by silica gel column chromatography (developer: toluene/ethyl acetate=4/1 (volumetric ratio)) to obtain 3-(4-(10-bromoanthracen-9-yl)phenyl)-5-methylpyridine (7.8 g).

Synthesis of 2-methyl-4-(4-(4,4,5,5-tetramethyl-1,3,2-dioxaborolan-2-yl)phenyl)pyridine 4-(4-Bromophenyl)-2-methylpyridine (4.5 g), bispinacolatodiboron (5.6 g), PdCl$_2$(dppf) (0.5 g), potassium acetate (5.9 g) and cyclopentyl methyl ether (50 ml) were placed into a flask, and the mixture was stirred at a refluxing temperature for 3 hours and 30 minutes under the nitrogen atmosphere. The reaction solution was cooled to room temperature, and filtered with a Hirsch funnel paved with Celite, and the solvent of the filtrate was distilled off under reduced pressure. The resulting solid was purified by active carbon column chromatography (developer: toluene) to obtain 2-methyl-4-(4-(4,4,5,5-tetramethyl-1,3,2-dioxaborolan-2-yl)phenyl)pyridine (5.0 g).

Synthesis of 2-methyl-4-(4-(10-(4-(5-methylpyridin-3-yl)phenyl)anthracen-9-yl)phenyl)pyridine 3-(4-(10-Bromoanthracen-9-yl)phenyl)-5-methylpyridine (2.3 g), 2-methyl-4-(4-(4,4,5,5-tetramethyl-1,3,2-dioxaborolan-2-yl)phenyl)pyridine (1.9 g), Pd(PPh$_3$)$_4$ (0.2 g), tripotassium phosphate (2.3 g), 1,2,4-trimethylbenzene (15 ml) and t-butyl alcohol (3 ml) were placed into a flask, and the mixture was stirred at a refluxing temperature for 14 hours under the nitrogen atmosphere. After completion of heating, the reaction solution was cooled to room temperature, water was added, and insolubles were filtered by suction filtration. After the solvent was distilled off under reduced pressure, the resulting solid was purified by NH-modified silica gel (DM1020: manufactured by Fuji Silysia Chemical Ltd.) column chromatography (developer: toluene). The crude product was further recrystallized from chlorobenzene to obtain a compound represented by the formula (1-151) "2-methyl-4-(4-(10-(4-(5-methylpyridin-3-yl)phenyl)anthracen-9-yl)phenyl)pyridine" (1.3 g).

A structure of the objective compound (1-151) was confirmed by NMR measurement.

$^1$H-NMR (CDC$_3$): δ=8.85 (m, 1H), 8.63 (d, 1H), 8.51 (m, 1H), 7.86-7.91 (m, 3H), 7.84 (d, 2H), 7.73-7.80 (m, 4H), 7.61 (t, 4H), 7.56 (s, 1H), 7.50 (d, 1H), 7.39 (m, 4H), 2.70 (s, 3H), 2.48 (s, 3H).

Synthetic Example of Compound Represented by Formula (1-164)

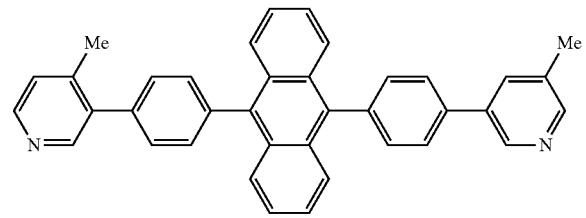

(1-164)

Synthesis of 4-methyl-3-(4-(10-(4-(5-methylpyridin-3-yl)phenyl) anthracen-9-yl)phenyl)pyridine 3-(4-(10-Bromoanthracen-9-yl)phenyl)-5-methylpyridine (3.3 g), 4-methyl-3-(4-(4,4,5,5-tetramethyl-1,3,2-dioxaborolan-2-yl)phenyl)pyridine (3.6 g), Pd(PPh$_3$)$_4$ (0.2 g), tripotassium phosphate (3.0 g), 1,2,4-trimethylbenzene (20 ml), t-butyl alcohol (5 ml) and water (1 ml) were placed into a flask, and the mixture was stirred at a refluxing temperature for 14 hours under the nitrogen atmosphere. After completion of heating, the reaction solution was cooled to room temperature, water and toluene were added, and the layers were separated. After the solvent was distilled off under reduced pressure, the resulting solid was purified by silica gel column chromatography (developer: toluene/ethyl acetate=3/2 (volumetric ratio)). The crude product was further recrystallized from chlorobenzene and, then, anisole to obtain a compound represented by the formula (1-164) "4-methyl-3-(4-(10-(4-(5-methylpyridin-3-yl)phenyl) anthracen-9-yl)phenyl)pyridine" (0.9 g).

A structure of the objective compound (1-164) was confirmed by NMR measurement.

$^1$H-NMR (CDC$_3$): δ=8.85 (m, 1H), 8.66 (s, 1H), 8.52 (d, 1H), 8.51 (m, 1H), 7.88 (m, 1H), 7.84 (d, 2H), 7.75-7.81 (m, 4H), 7.61 (d, 2H), 7.59 (s, 4H), 7.40 (m, 4H), 7.28 (d, 1H), 2.50 (s, 3H), 2.48 (s, 3H).

Synthetic Example of Compound Represented by Formula (1-236)

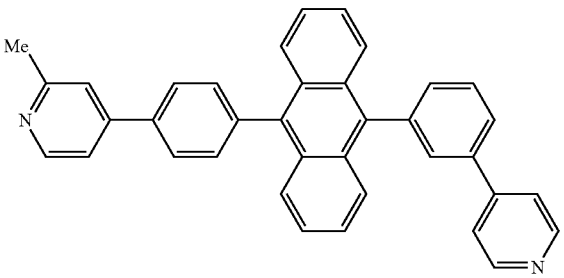

(1-236)

Synthesis of 2-methyl-4-(4-(10-(3-(pyridin-4-yl) phenyl)anthracen-9-yl)phenyl)pyridine 4-(3-(10-Bromoanthracen-9-yl)phenyl)pyridine (2.0 g), 2-methyl-4-(4-(4,4,5,5-tetramethyl-1,3,2-dioxaborolan-2-yl) phenyl)pyridine (1.7 g), Pd(PPh$_3$)$_4$ (0.2 g), tripotassium phosphate (2.1 g), 1,2,4-trimethylbenzene (20 ml) and t-butyl alcohol (5 ml) were placed into a flask, and the mixture was stirred at a refluxing temperature for 13 hours under the nitrogen atmosphere. After completion of heating, the reaction solution was cooled to room temperature, water and toluene were added, and the layers were separated. After the solvent was distilled off under reduced pressure, the resulting solid was purified by silica gel column chromatography (developer: toluene/ethyl acetate). Thereupon, a ratio of ethyl acetate in a developer was gradually increased to elute an objective substance. The crude product was further purified by NH-modified silica gel (DM1020: manufactured by Fuji Silysia Chemical Ltd.) column chromatography (developer: toluene) to obtain a compound represented by the formula (1-236) "2-methyl-4-(4-(10-(3-(pyridin-4-yl) phenyl) anthracen-9-yl)phenyl)pyridine" (1.5 g).

A structure of the objective compound (1-236) was confirmed by NMR measurement.

$^1$H-NMR (CDC$_3$): δ=8.67 (m, 2H), 8.63 (d, 1H), 7.89 (d, 2H), 7.86 (d, 1H), 7.80 (m, 1H), 7.72-7.78 (m, 5H), 7.58-7.65 (m, 5H), 7.56 (s, 1H), 7.49 (d, 1H), 7.38 (m, 4H), 2.70 (s, 3H).

Synthetic Example of Compound Represented by Formula (1-249)

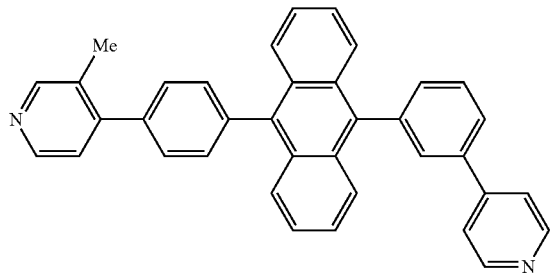

(1-249)

Synthesis of 4-methyl-3-(4-(10-(3-(pyridin-4-yl) phenyl) anthracen-9-yl)phenyl)pyridine 4-(3-(10-Bromoanthracen-9-yl)phenyl)pyridine (2.5 g), 4-methyl-3-(4-(4,4,5,5-tetramethyl-1,3,2-dioxaborolan-2-yl)phenyl)pyridine (2.2 g), Pd(PPh$_3$)$_4$ (0.2 g), tripotassium phosphate (2.6 g), 1,2,4-trimethylbenzene (16 ml), t-butyl alcohol (3 ml) and water (1 ml) were placed into a flask, and the mixture was stirred at a refluxing temperature for 15 hours under the nitrogen atmosphere. After completion of heating, the reaction solution was cooled to room temperature, water and toluene were added, and the layers were separated. After the solvent was distilled off under reduced pressure, the resulting solid was purified by silica gel column chromatography (developer: toluene/ethyl acetate). Thereupon, a ratio of ethyl acetate in a developer was gradually increased to elute an objective substance. The solid obtained by distilling the solvent off under reduced pressure was washed with acetone to obtain a compound represented by the formula (1-249) "4-methyl-3-(4-(10-(3-(pyridin-4-yl)phenyl) anthracen-9-yl)phenyl)pyridine" (1.0 g).

A structure of the objective compound (1-249) was confirmed by NMR measurement.

$^1$H-NMR (CDC$_3$): δ=8.67 (m, 3H), 8.53 (m, 1H), 7.87 (d, 1H), 7.72-7.83 (m, 6H), 7.57-7.63 (m, 6H), 7.35-7.43 (m, 5H), 7.28 (d, 1H), 2.50 (s, 3H).

Synthetic Example of Compound Represented by Formula (1-262)

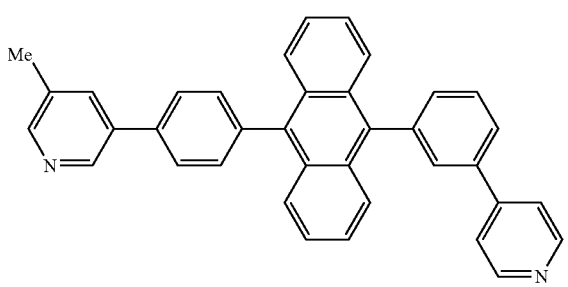

(1-262)

Synthesis of 3-methyl-5-(4-(10-(3-(pyridin-4-yl) phenyl)anthracen-9-yl)phenyl)pyridine 4-(3-(10-Bromoanthracen-9-yl)phenyl)pyridine (2.9 g), 3-methyl-5-(4-(4,4,5,5-tetramethyl-1,3,2-dioxaborolan-2-yl)phenyl)pyridine (2.5 g), Pd(PPh$_3$)$_4$ (0.2 g), tripotassium phosphate (3.0 g), 1,2,4-trimethylbenzene (20 ml), t-butyl alcohol (5 ml) and water (1 ml) were placed into a flask, and the mixture was stirred at a refluxing temperature for 9 hours under the nitrogen atmosphere. After completion of heating, the reaction solution was cooled to room temperature, water and toluene were added, and the layers were separated. After the solvent was distilled off under reduced pressure, the resulting solid was purified by silica gel column chromatography (developer: toluene/ethyl acetate=3/2 (volumetric ratio)) to obtain a compound represented by the formula (1-262) "3-methyl-5-(4-(10-(3-(pyridin-4-yl)phenyl)anthracen-9-yl)phenyl)pyridine" (1.2 g).

A structure of the objective compound (1-262) was confirmed by NMR measurement.

$^1$H-NMR (CDC$_3$): δ=8.85 (m, 1H), 8.68 (m, 2H), 8.51 (m, 1H), 7.83-7.90 (m, 4H), 7.72-7.82 (m, 6H), 7.60 (m, 5H), 7.38 (m, 4H), 2.49 (s, 3H).

Synthetic Example of Compound Represented by the Formula (1-46)

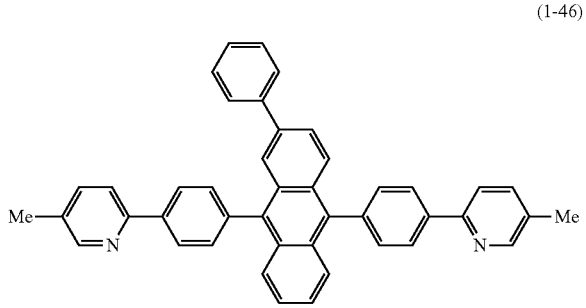 [SMILES: Cc1ccc(-c2ccc(-c3c4ccccc4c(-c4ccc(-c5ccc(C)cn5)cc4)c4cc(-c5ccccc5)ccc34)cc2)nc1]

(1-46)

Synthesis of 2-(4-bromophenyl)-5-methylpyridine

A flask containing 2-bromo-5-methylpyridine (24.9 g) and THF (50 ml) was cooled with an ice bath, and a 2M isopropylmagnesium chloride THF solution (80.0 ml) was added dropwise to this solution. After completion of addition, a temperature was raised to room temperature, and the solution was stirred for 3 hours. Then, the solution was cooled again with an ice bath, zinc chloride tetramethylethylenediamine (43.8 g) was added and, thereafter, the solution was stirred at room temperature for 30 minutes. To this solution were added 1-bromo-4-iodobenzene (41.0 g) and Pd(PPh$_3$)$_4$ (1.7 g), and the solution was stirred at a refluxing temperature for 3 hours and 30 minutes. After the reaction solution was cooled to room temperature, an EDTA.4Na aqueous solution and ethyl acetate were added, and the layers were separated. After the solvent was distilled off under reduced pressure, the resulting solid was purified by silica gel column chromatography (developer: toluene/ethyl acetate=9/1 (volumetric ratio)) to obtain 2-(4-bromophenyl)-5-methylpyridine (21.5 g).

Synthesis of 6,6'-((2-phenylanthracen-9,10-diyl)bis (4,1-phenylene))bis(3-methylpyridine)

9,10-Bis(4,4,5,5-tetramethyl-1,3,2-dioxaborolanyl)-2-phenylanthracene (4.1 g), 2-(4-bromophenyl)-5-methylpyridine (4.4 g), Pd(PPh$_3$)$_4$ (0.3 g), tripotassium phosphate (6.8 g), 1,2,4-trimethylbenzene (20 ml), t-butyl alcohol (5 ml) and water (1 ml) were placed into a flask, and the mixture was stirred at a refluxing temperature for 7 hours and 30 minutes under the nitrogen atmosphere. After completion of heating, the reaction solution was cooled to room temperature, water and toluene were added, and the layers were separated. After the solvent was distilled off under reduced pressure, the resulting solid was purified by silica gel column chromatography (developer: toluene/ethyl acetate=9/1 (volumetric ratio)), and further recrystallized from chlorobenzene to obtain a compound represented by the formula (1-46) "6,6'-((2-phenylanthracen-9,10-diyl)bis(4,1-phenylene))bis(3-methylpyridine)" (1.0 g).

A structure of the objective compound (1-46) was confirmed by NMR measurement.

$^1$H-NMR (CDC$_3$): δ=8.61 (m, 2H), 8.24 (d, 4H), 7.99 (m, 1H), 7.87 (d, 1H), 7.75-7.83 (m, 4H), 7.61-7.68 (m, 7H), 7.57 (d, 2H), 7.32-7.41 (m, 4H), 7.30 (t, 1H), 2.43 (s, 6H).

A glass transition temperature (Tg) of the objective compound (1-46) was 135.5° C.

Synthetic Example of Compound Represented by Formula (1-68)

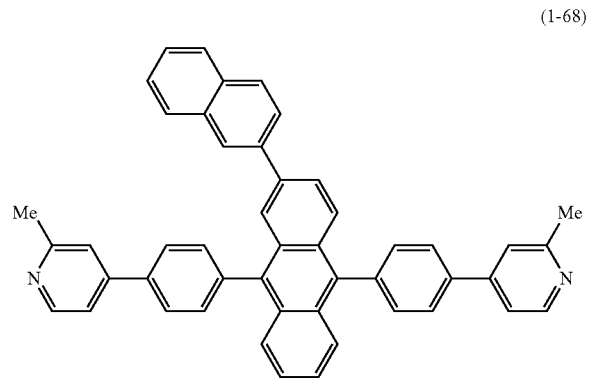 [SMILES: Cc1cc(-c2ccc(-c3c4ccccc4c(-c4ccc(-c5ccnc(C)c5)cc4)c4cc(-c5ccc6ccccc6c5)ccc34)cc2)ccn1]

(1-68)

Synthesis of 2-methyl-4-(4-(4,4,5,5-tetramethyl-1,3,2-dioxaborolan-2-yl)phenyl)pyridine 4-(4-Chlorophenyl)-2-methylpyridine (Rieke Metals, Inc.) (80.0 g), bispinacolatodiboron (104.7 g), potassium acetate (325.7 g), bis(dibenzylideneacetone) palladium (0) (Pd(dba)$_2$) (13.6 g), tricyclohexylphosphine (13.2 g) and anisole (800 ml) were placed into a flask, and the mixture was stirred at 115° C. for 11 hours under the nitrogen atmosphere. The reaction solution was cooled to room temperature, water and toluene were added, the layers were separated, and the solvent of the organic layer was distilled off under reduced pressure. The resulting crude product was purified by active carbon column chromatography (developer: toluene) to obtain 2-methyl-4-(4-(4,4,5,5-tetramethyl-1,3,2-dioxaborolan-2-yl)phenyl)pyridine (127.0 g).

Synthesis of 4,4'-((2-(naphthalen-2-yl) anthracen-9,10-diyl)bis(4,1-phenylene))bis(2-methylpyridine)

9,10-Dibromo-2-(naphthalen-2-yl) anthracene (7.0 g), 2-methyl-4-(4-(4,4,5,5-tetramethyl-1,3,2-dioxaborolan-2-yl)phenyl)pyridine (13.4 g), bis(dibenzylideneacetone) palladium (0) (Pd(dba)$_2$) (0.1 g), tricyclohexylphosphine (0.2 g), tripotassium phosphate (16.1 g) and 1,2,4-trimethylbenzene (105 ml) were placed into a flask, and the mixture was stirred at 130° C. for 8 hours under the nitrogen atmosphere. After completion of heating, the reaction solution was cooled to room temperature, water and methanol were added to dissolve the inorganic salt, and the solid containing an objective substance was taken by suction filtration. The resulting solid was washed with methanol, ethyl acetate and orthodichlorobenzene, and purified by active carbon column chromatography (developer: orthodichlorobenzene). The solvent was distilled off under reduced pressure, and the resulting solid was washed with orthodichlorobenzene two times to obtain a compound represented by the formula (1-68) "4,4'-((2-(naphthalen-2-yl) anthracen-9,10-diyl)bis(4,1-phenylene))bis(2-methylpyridine)" (5.1 g).

A structure of the objective compound (1-68) was confirmed by NMR measurement.

$^1$H-NMR (CDC$_3$): δ=8.64 (m, 2H), 8.04 (m, 1H), 8.01 (m, 1H), 7.92 (d, 4H), 7.73-7.90 (m, 7H), 7.63-7.71 (m, 5H), 7.57 (m, 2H), 7.42-7.53 (m, 4H), 7.39 (m, 2H), 2.69 (m, 6H).

A glass transition temperature (Tg) of the objective compound (1-68) was 123.8° C.

Synthetic Example of Compound Represented by Formula (1-72)

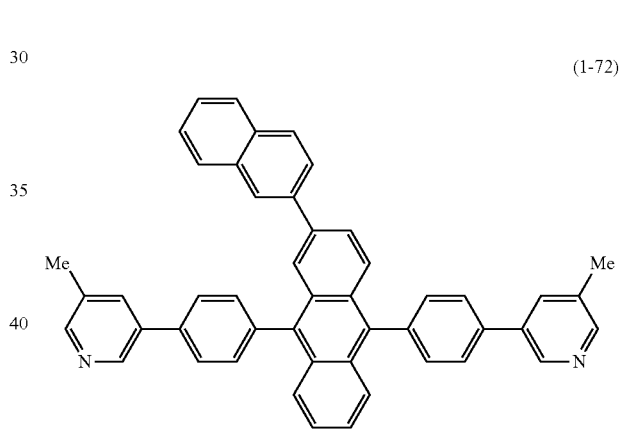

(1-72)

Synthesis of 5,5'-((2-(naphthalen-2-yl) anthracen-9,10-diyl)bis(4,1-phenylene))bis(3-methylpyridine)

2,2'-(2-(Naphthalen-2-yl) anthracen-9,10-diyl)bis(4,4,5,5-tetramethyl-1,3,2-dioxaborolane) (6.3 g), 3-(4-bromophenyl)-5-methylpyridine (6.7 g), Pd(PPh$_3$)$_4$ (0.4 g), tripotassium phosphate (12.0 g), 1,2,4-trimethylbenzene (63 ml) and t-butyl alcohol (13 ml) were placed into a flask, and the mixture was stirred at 100° C. for 3 hours under the nitrogen atmosphere. After completion of heating, the reaction solution was cooled to room temperature, water and toluene were added, the layers were separated, and the solvent of the organic layer was distilled off under reduced pressure. The resulting solid was washed with methanol and, then, ethyl acetate, and purified by active carbon column chromatography (developer: chlorobenzene). The solvent was distilled off under reduced pressure, and the resulting solid was washed with ethyl acetate three times to obtain a compound represented by the formula (1-72) "5,5'-((2-(naphthalen-2-yl) anthracen-9,10-diyl)bis(4,1-phenylene))bis(3-methylpyridine)" (4.2 g).

A structure of the objective compound (1-72) was confirmed by NMR measurement.

$^1$H-NMR (CDC$_3$): δ=8.87 (m, 2H), 8.50 (dd, 2H), 8.07 (m, 1H), 8.02 (m, 1H), 7.75-7.91 (m, 13H), 7.62-7.72 (m, 5H), 7.37-7.49 (m, 4H), 2.48 (m, 6H).

A glass transition temperature (Tg) of the objective compound (1-72) was 120.6° C.

Synthetic Example of Compound Represented by Formula (1-71)

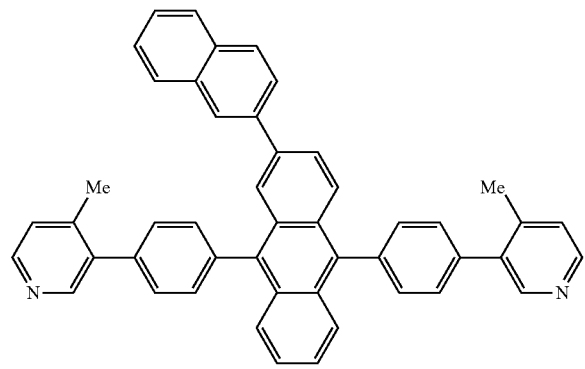

(1-71)

Synthesis of 3,3'-((2-(naphthalen-2-yl) anthracen-9, 10-diyl)bis(4,1-phenylene))bis(4-methylpyridine)

2,2'-(2-(Naphthalen-2-yl) anthracen-9,10-diyl)bis(4,4,5,5-tetramethyl-1,3,2-dioxaborolane) (5.9 g), 3-(4-bromophenyl)-4-methylpyridine (6.3 g), Pd(PPh$_3$)$_4$ (0.4 g), tripotassium phosphate (11.2 g), 1,2,4-trimethylbenzene (59 ml) and isopropyl alcohol (12 ml) were placed into a flask, and the mixture was stirred at 93° C. for 2 hours under the nitrogen atmosphere. After completion of heating, the reaction solution was cooled to room temperature, water and toluene were added, the layers were separated, and the solvent of the organic layer was distilled off under reduced pressure. The resulting solid was purified by silica gel column chromatography (developer: toluene/ethyl acetate). Thereupon, a ratio of ethyl acetate in a developer was gradually increased to elute an objective substance. The solvent was distilled off under reduced pressure, and the resulting solid was recrystallized from an acetone/toluene mixed solvent to obtain a compound represented by the formula (1-71) "3,3'-((2-(naphthalen-2-yl) anthracen-9,10-diyl)bis(4,1-phenylene))bis(4-methylpyridine)" (2.0 g).

A structure of the objective compound (1-71) was confirmed by NMR measurement.

$^1$H-NMR (CDC$_3$): δ=8.68 (d, 2H), 8.53 (t, 2H), 8.09 (m, 1H), 8.03 (m, 1H), 7.92 (d, 1H), 7.89 (d, 1H), 7.80-7.87 (m, 5H), 7.72 (dd, 1H), 7.60-7.68 (m, 8H), 7.41-7.52 (m, 4H), 7.29 (t, 21-1), 2.50 (m, 6H).

A glass transition temperature (Tg) of the objective compound (1-71) was 117.4° C.

Synthetic Example of Compound Represented by Formula (1-110)

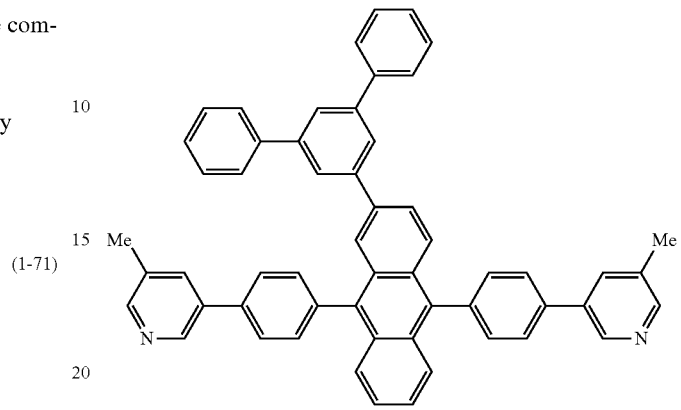

(1-110)

Synthesis of 5,5'-((2-([1,1':3',1''-terphenylyl]-5'-yl) anthracen-9,10-diyl)bis(4,1-phenylene))bis(3-methylpyridine)

2,2'-(2-([1,1':3',1''-Terphenylyl]-5'-yl)anthracen-9,10-diyl)bis(4,4,5,5-tetramethyl-1,3,2-dioxaborolane) (2.9 g), 3-(4-bromophenyl)-5-methylpyridine (2.6 g), Pd(PPh$_3$)$_4$ (0.2 g), tripotassium phosphate (3.7 g), 1,2,4-trimethylbenzene (25 ml), t-butyl alcohol (5 ml) and water (1 ml) were placed into a flask, and the mixture was stirred at a refluxing temperature for 15 hours under the nitrogen atmosphere. After completion of heating, the reaction solution was cooled to room temperature, water and toluene were added, the layers were separated, and the solvent of the organic layer was distilled off under reduced pressure. The resulting solid was purified by silica gel column chromatography (developer: toluene/ethyl acetate). Thereupon, a ratio of ethyl acetate in a developer was gradually increased to elute an objective substance. Then, the crude product was purified by active carbon column chromatography (developer: toluene). The solvent was distilled off under reduced pressure, and the resulting solid was washed with ethyl acetate to obtain a compound represented by the formula (1-110) "5,5'-((2-([1,1':3',1''-terphenylyl]-5'-yl)anthracen-9,10-diyl) bis(4,1-phenylene))bis(3-methylpyridine)" (0.4 g).

A structure of the objective compound (1-110) was confirmed by NMR measurement.

$^1$H-NMR (CDC$_3$): δ=8.86 (dd, 2H), 8.51 (m, 2H), 8.05 (m, 1H), 7.78-7.91 (m, 9H), 7.74 (m, 4H), 7.60-7.69 (m, 8H), 7.35-7.47 (m, H), 2.48 (m, 6H).

By appropriately changing raw material compounds, other anthracene derivatives of the present invention can be synthesized by methods in accordance with the above-mentioned synthesis examples.

Hereinbelow, in order to explain the present invention in further detail, respective Examples will be shown, but the present invention is not limited by them.

Electroluminescent elements relating to Examples 1 to 8 and Comparative Examples 1 to 4, Examples 9 to 11 and Comparative Example 5 and, further, Example 12 were manufactured, a voltage (V) and an external quantum efficiency (%) which are property at 1000 cd/m² emission were measured, respectively, and then, a time during which luminance of 80% (1200 cd/m²) or more is held when elements are driven at a constant current at a current density when luminance of 1500 cd/m² is obtained, was measured. Hereinbelow, Examples and Comparative Examples will be explained in detail.

In addition, as a quantum efficiency of a luminescent element, there are an internal quantum efficiency and an external quantum efficiency, and the internal quantum efficiency shows a ratio that external energy which is injected into a luminescent layer of a luminescent element as an electron (or a hole) is purely converted into a photon. On the other hand, the external quantum efficiency is calculated based on an amount of this photon which is released to the outside of a luminescent element, and since a part of photons generated in a luminescent layer are continuously absorbed or reflected inside a luminescent element, and are not released to the outside of a luminescent element, the external quantum efficiency becomes lower than the internal quantum efficiency.

A method of measuring the external quantum efficiency is as follows: A current at which luminance of an element becomes 1000 cd/m² was applied to make the element emit light, using a voltage/current generator R6144 manufactured by Advantest Corporation. Using a spectral emission luminance meter SR-3AR manufactured by TOPCON Corporation, spectral emission luminance of a visible light region was measured from a direction perpendicular to a light-emitting surface. A value obtained by dividing a value of spectral emission luminance of each measured wavelength component by wavelength energy and multiplying the resultant with π on the assumption that a light-emitting surface is a complete diffusion surface is the photon number at each wavelength. Then, the photon number was integrated in an observed entire wavelength region, and was adopted as the entire number of photons released from the element. A value obtained by dividing an applied current value by an elementary charge is adopted as the number of carriers injected into the element, and a value obtained by dividing the entire number of photons released from the element by the number of carriers injected into the element is an external quantum efficiency.

A material constitution of each layer in the manufactured electroluminescent elements relating to Examples 1 to 8 and Comparative Examples 1 to 4 is shown in the following Table 1. In addition, an electron transport layer was formed with a mixture of a compound listed in the following Table and 8-quinolinollithium (Liq).

TABLE 1

| | Hole injection layer 1 | Hole injection layer 2 | Hole transport layer | Luminescent layer (20 nm) | | Electron transport layer | Cathode |
|---|---|---|---|---|---|---|---|
| | (60 nm) | (10 nm) | (10 nm) | Host | Dopant | (30 nm) | (1 nm/100 nm) |
| Example 1 | HT-1 | HAT-CN | NPB | BH1 | BD1 | Compound (1-38) | Liq/Al |
| Example 2 | HT-1 | HAT-CN | NPB | BH1 | BD1 | Compound (1-39) | Liq/Al |
| Comparative Example 1 | HT-1 | HAT-CN | NPB | BH1 | BD1 | Compound (A) | Liq/Al |
| Example 3 | HT-1 | HAT-CN | NPB | BH1 | BD1 | Compound (1-38) | Liq/Mg + Ag |
| Example 4 | HT-1 | HAT-CN | NPB | BH1 | BD1 | Compound (1-39) | Liq/Mg + Ag |
| Example 5 | HT-1 | HAT-CN | NPB | BH1 | BD1 | Compound (1-40) | Liq/Mg + Ag |
| Comparative Example 2 | HT-1 | HAT-CN | NPB | BH1 | BD1 | Compound (A) | Liq/Mg + Ag |
| Example 6 | HT-1 | HAT-CN | NPB | BH1 | BD1 | Compound (1-35) | Liq/Mg + Ag |
| Example 7 | HT-1 | HAT-CN | NPB | BH1 | BD1 | Compound (1-34) | Liq/Mg + Ag |
| Comparative Example 3 | HT-1 | HAT-CN | NPB | BH1 | BD1 | Compound (B) | Liq/Mg + Ag |
| Example 8 | HT-1 | HAT-CN | NPB | BH1 | BD1 | Compound (1-51) | Liq/Al |
| Comparative Example 4 | HT-1 | HAT-CN | NPB | BH1 | BD1 | Compound (C) | Liq/Al |

* An electron transport layer was formed with a mixture of a compound listed in the Table and Liq.

Furthermore, a material constitution of each layer in the manufactured electroluminescent elements relating to Examples 9 to 11 and Comparative Example 5 is shown in the following Table 2. Comparative Example 2 is described together as Comparative Example of Examples 9 and 10. In addition, an electron transport layer was formed with a mixture of a compound listed in the following Table and 8-quinolinollithium (Liq).

TABLE 2

| | Hole injection layer 1 (60 nm) | Hole injection layer 2 (10 nm) | Hole transport layer (10 nm) | Luminescent layer (20 nm) Host | Luminescent layer (20 nm) Dopant | Electron transport layer (30 nm) | Cathode (1 nm/100 nm) |
|---|---|---|---|---|---|---|---|
| Example 9 | HT-1 | HAT-CN | NPB | BH1 | BD1 | Compound (1-6) | Liq/Mg + Ag |
| Example 10 | HT-1 | HAT-CN | NPB | BH1 | BD1 | Compound (1-164) | Liq/Mg + Ag |
| Comparative Example 2 | HT-1 | HAT-CN | NPB | BH1 | BD1 | Compound (A) | Liq/Mg + Ag |
| Example 11 | HT-1 | HAT-CN | NPB | BH1 | BD1 | Compound (1-262) | Liq/Mg + Ag |
| Comparative Example 5 | HT-1 | HAT-CN | NPB | BH1 | BD1 | Compound (D) | Liq/Mg + Ag |

\* An electron transport layer was formed with a mixture of a compound listed in the Table and Liq.

A material constitution of each layer in the manufactured electroluminescent element relating to Example 12 is shown in the following Table 3. Comparative Example 3 is described together as Comparative Example of Example 12. In addition, an electron transport layer was formed with a mixture of a compound listed in the following Table and 8-quinolinollithium (Liq).

TABLE 3

| | Hole injection layer 1 (60 nm) | Hole injection layer 2 (10 nm) | Hole transport layer (10 nm) | Luminescent layer (20 nm) Host | Luminescent layer (20 nm) Dopant | Electron transport layer (30 nm) | Cathode (1 nm/100 nm) |
|---|---|---|---|---|---|---|---|
| Example 12 | HT-1 | HAT-CN | NPB | BH1 | BD1 | Compound (1-68) | Liq/Mg + Ag |
| Comparative Example 3 | HT-1 | HAT-CN | NPB | BH1 | BD1 | Compound (B) | Liq/Mg + Ag |

\* An electron transport layer was formed with a mixture of a compound listed in the Table and Liq.

In Tables 1 to 3, "HT-1" is $N^4,N^{4'}$-diphenyl-$N^4,N^{4'}$-bis-(9-phenyl-9H-carbazol-3-yl)-biphenyl-4,4'-diamine, "HAT-CN" is 1,4,5,8,9,12-hexaaza-triphenylene-2,3,6,7,10,11-hexacarbonitrile, "NPB" is $N^4,N^{4'}$-dinaphthalen-1-yl-$N^4$,$N^{4'}$-diphenyl-biphenyl-4,4'-diamine, "BH1" is 9-phenyl-10-(4-phenyl-naphthalen-1-yl)-anthracene, "BD1" is 7,7-dimethyl-$N^5,N^9$-diphenyl-$N^5,N^9$-bis-(4-trimethylsilanyl-phenyl)-7H-benzo[c]fluorene-5,9-diamine, and "Liq" is 8-quinolinollithium. Chemical structures thereof are shown hereinbelow together with compounds (A) to (C) and (D) used as Comparative Example.

HT-1

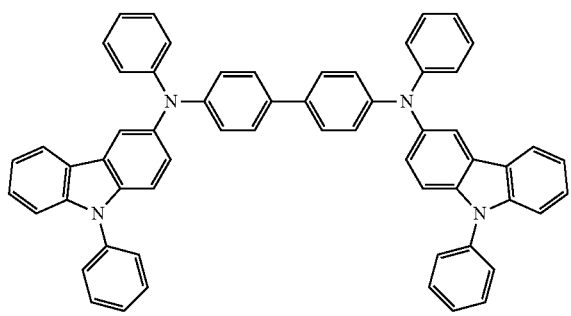

-continued

HAT-CN

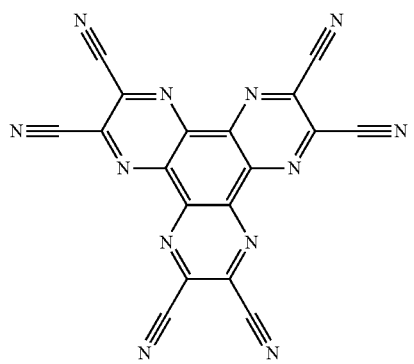

NPB

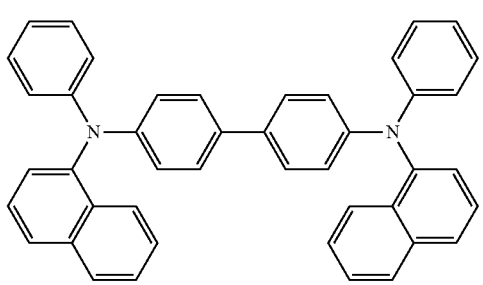

-continued

Liq
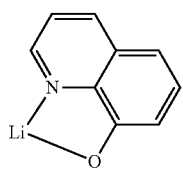

BH1
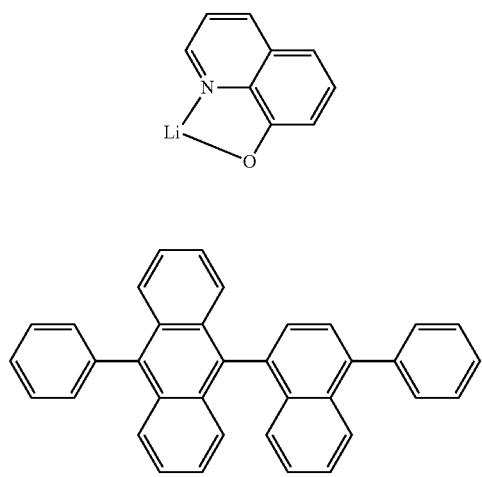

BD1
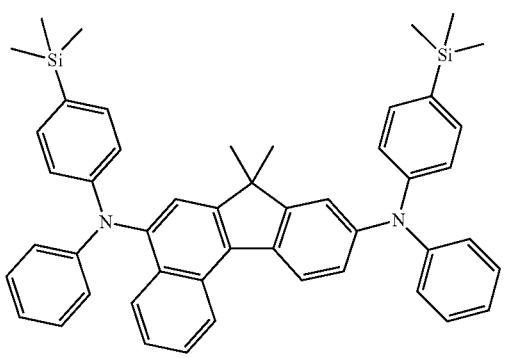

Compound (A)
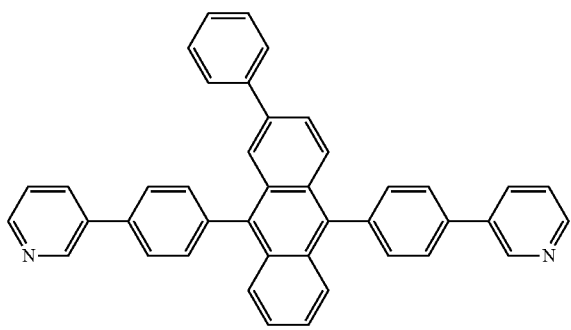

Compound (B)
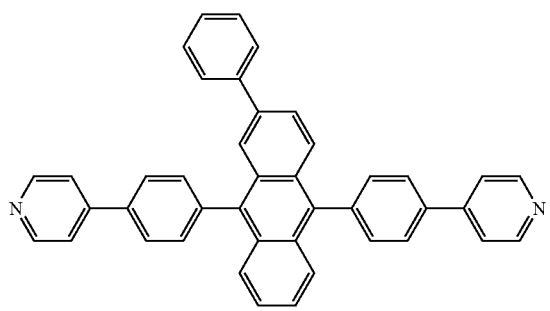

-continued

Compound (C)
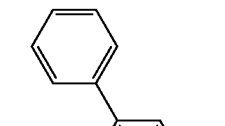
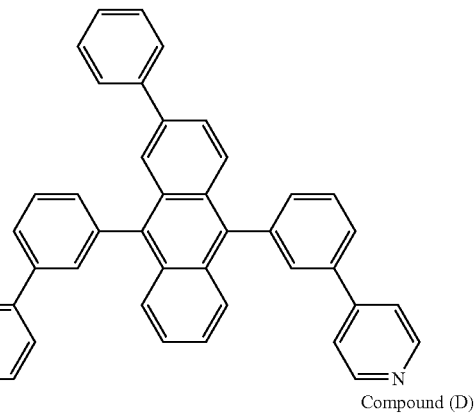

Compound (D)
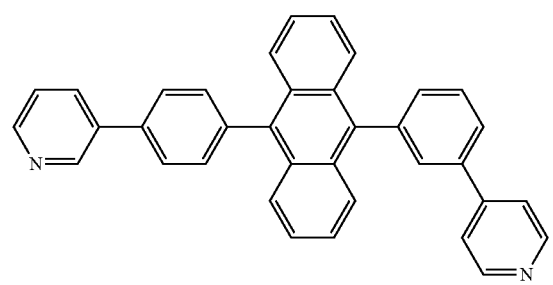

Example 1

Element Using Compound (1-38) in Electron Transport Material

A 26 mm×28 mm×0.7 mm glass substrate (manufactured by Opto Science, Inc.) obtained by polishing ITO which had been made into a film having the thickness of 180 nm by sputtering to 150 nm was used as a transparent support substrate. This transparent support substrate was fixed on a substrate holder of a commercially available deposition apparatus (manufactured by Sinku Kiko Co., Ltd.), a deposition boat made of molybdenum containing HT-1, a deposition boat made of molybdenum containing HAT-CN, a deposition boat made of molybdenum containing NPB, a deposition boat made of molybdenum containing BH1, a deposition boat made of molybdenum containing BD1, a deposition boat made of molybdenum containing the compound (1-38) of the present invention, a deposition boat made of molybdenum containing Liq, and a deposition boat made of tungsten containing aluminum were loaded.

The following respective layers were sequentially formed on an ITO film of the transparent support substrate. A hole injection layer consisting of two layers was formed by decompressing a vacuum tank to $5\times10^{-4}$ Pa, first heating the deposition boat containing HT-1 to deposit HT-1 to the film thickness of 60 nm and, further, heating the deposition boat containing HAT-CN to deposit HAT-CN to the film thickness of 10 nm and then, a hole transport layer was formed by heating the deposition boat containing NPB to deposit NPB to the film thickness of 10 nm. Then, a luminescent layer was formed by heating the deposition boat containing BH1 and the deposition boat containing BD1 simultaneously to deposit them to the film thickness of 20 nm. A deposition rate was regulated so that the weight ratio of BH1 and BD1 became approximately 95 vs 5. Then, an electron transport layer was formed by heating the deposition boat containing the compound (1-38) and the deposition boat containing Liq simultaneously to deposit them to the film thickness of 30 nm. A deposition rate was regulated so that the weight ratio of the compound (1-38) and Liq became approximately 1 vs 1. A deposition rate of each layer was 0.01 to 1 nm/sec.

Thereafter, the deposition boat containing Liq was heated to deposit Liq at a deposition rate of 0.01 to 0.1 nm/sec so that the film thickness became 1 nm. Then, a cathode was formed by heating the deposition boat containing aluminum to deposit aluminum at a deposition rate of 0.01 to 2 nm/sec so that the film thickness became 100 nm, to obtain an organic EL element.

When property at 1000 $cd/m^2$ emission was measured using an ITO electrode as an anode, and a Liq/aluminum electrode as a cathode, a driving voltage was 3.7 V, and an external quantum efficiency was 6.3%. A constant current driving test was performed at a current density at which luminance of 1500 $cd/m^2$ is obtained and, as a result, a time during which luminance of 80% (1200 $cd/m^2$) or more of initial luminance is held, was 500 hours.

Example 2

Element Using Compound (1-39) in Electron Transport Material

According to the same manner as that of Example 1 except that the compound (1-38) was changed to a compound (1-39), an organic EL element was obtained. When the same test was performed, a driving voltage was 4.0 V, an external quantum efficiency was 5.8%, and a time during which luminance of 80% or more of initial luminance is held, was 500 hours.

Comparative Example 1

Element Using Compound (A) in Electron Transport Material

According to the same manner as that of Example 1 except that the compound (1-38) was changed to a compound (A) of Comparative Example, an organic EL element was obtained. When the same test was performed, a driving voltage was 3.7 V, an external quantum efficiency was 5.1%, and a time during which luminance of 80% or more of initial luminance is held, was 300 hours.

Example 3

Element Using Compound (1-38) in Electron Transport Material

According to the same manner as that of Example 1 except that a method of forming a cathode was changed, an organic EL element was obtained. A cathode was formed by heating the deposition boat containing Liq to deposit Liq at a deposition rate of 0.01 to 0.1 nm/sec so that the film thickness became 1 nm and, thereafter, simultaneously heating a boat containing magnesium and a boat containing silver which had been separately prepared, to deposit them so that the film thickness became 100 nm. Thereupon, regulation was performed so that the atomic number ratio of magnesium and silver became 10 vs 1, and a deposition rate became 0.1 to 10 nm/sec.

When the same test as that of Example 1 was performed, a driving voltage was 3.7 V, an external quantum efficiency was 5.5%, and a time during which luminance of 80% or more of initial luminance is held, was 400 hours.

Example 4

Element Using Compound (1-39) in Electron Transport Material

According to the same manner as that of Example 3 except that the compound (1-38) was changed to a compound (1-39), an organic EL element was obtained. When the same test was performed, a driving voltage was 3.9 V, an external quantum efficiency was 5.5%, and a time during which luminance of 80% or more of initial luminance is held, was 500 hours.

Example 5

Element Using Compound (1-40) in Electron Transport Material

According to the same manner as that of Example 3 except that the compound (1-38) was changed to a compound (1-40), an organic EL element was obtained. When the same test was performed, a driving voltage was 3.4V, an external quantum efficiency was 5.9%, and a time during which luminance of 80% or more of initial luminance is held, was 350 hours.

Comparative Example 2

Element Using Compound (A) in Electron Transport Material

According to the same manner as that of Example 3 except that the compound (1-38) was changed to a compound (A) of Comparative Example, an organic EL element was obtained. When the same test was performed, a driving voltage was 3.6 V, an external quantum efficiency was 4.9%, and a time during which luminance of 80% or more of initial luminance is held, was 400 hours.

Example 6

Element Using Compound (1-35) in Electron Transport Material

According to the same manner as that of Example 3 except that the compound (1-38) was changed to a compound (1-35), an organic EL element was obtained. When the same test was performed, a driving voltage was 3.6 V, an external quantum efficiency was 5.6%, and a time during which luminance of 80% or more of initial luminance is held, was 300 hours.

Example 7

Element Using Compound (1-34) in Electron Transport Material

According to the same manner as that of Example 3 except that the compound (1-38) was changed to a compound (1-34), an organic EL element was obtained. When the same test was performed, a driving voltage was 3.6 V, an external quantum efficiency was 5.6%, and a time during which luminance of 80% or more of initial luminance is held, was 300 hours.

Comparative Example 3

Element Using Compound (B) in Electron Transport Material

According to the same manner as that of Example 3 except that the compound (1-38) was changed to a compound (B) of Comparative Example, an organic EL element was obtained. When the same test was performed, a driving voltage was 3.8 V, an external quantum efficiency was 4.3%, and a time during which luminance of 80% or more of initial luminance is held, was 220 hours.

Example 8

Element Using Compound (1-51) in Electron Transport Material

According to the same manner as that of Example 1 except that the compound (1-38) was changed to a compound (1-51), an organic EL element was obtained. When the same test was performed, a driving voltage was 3.8 V, an external quantum efficiency was 5.7%, and a time during which luminance of 80% or more of initial luminance is held, was 450 hours.

Comparative Example 4

Element Using Compound (C) in Electron Transport Material

According to the same manner as that of Example 1 except that the compound (1-38) was changed to a compound (C) of Comparative Example, an organic EL element was obtained. When the same test was performed, a driving voltage was 3.9 V, an external quantum efficiency was 5.8%, and a time during which luminance of 80% or more of initial luminance is held, was 380 hours.

Example 9

Element Using Compound (1-6) in Electron Transport Material

According to the same manner as that of Example 3 except that the compound (1-38) was changed to a compound (1-6), an organic EL element was obtained. When the same test was performed, a driving voltage was 3.7 V, an external quantum efficiency was 5.3%, and a time during which luminance of 80% or more of initial luminance is held, was 500 hours.

Example 10

Element Using Compound (1-164) in Electron Transport Material

According to the same manner as that of Example 3 except that the compound (1-38) was changed to a compound (1-164), an organic EL element was obtained. When the same test was performed, a driving voltage was 3.7 V, an external quantum efficiency was 5.6%, and a time during which luminance of 80% or more of initial luminance is held, was 400 hours.

Example 11

Element Using Compound (1-262) in Electron Transport Material

According to the same manner as that of Example 3 except that the compound (1-38) was changed to a compound (1-262), an organic EL element was obtained. When the same test was performed, a driving voltage was 3.6 V, an external quantum efficiency was 5.5%, and a time during which luminance of 80% or more of initial luminance is held, was 350 hours.

Comparative Example 5

Element Using Compound (D) in Electron Transport Material

According to the same manner as that of Example 3 except that the compound (1-38) was changed to a compound (D) of Comparative Example, an organic EL element was obtained. When the same test was performed, a driving voltage was 3.6 V, an external quantum efficiency was 5.0%, and a time during which luminance of 80% or more of initial luminance is held, was 350 hours.

Example 12

Element Using Compound (1-68) in Electron Transport Material

According to the same manner as that of Example 3 except that the compound (1-38) was changed to a compound (1-68), an organic EL element was obtained. When the same test was performed, a driving voltage was 4.6 V, an external quantum efficiency was 4.2%, and a time during which luminance of 80% or more of initial luminance is held, was 350 hours.

The following Table 4 summarizes test results of the above-mentioned electroluminescent elements relating to Examples 1 to 8 and Comparative Example 1 to 4.

TABLE 4

| | Electron transport layer material | Cathode material | Driving voltage (V) | External quantum efficiency (%) | Device life (hour) |
|---|---|---|---|---|---|
| Example 1 | Compound (1-38) | Liq/Al | 3.7 | 6.3 | 500 |
| Example 2 | Compound (1-39) | Liq/Al | 4.0 | 5.8 | 500 |
| Comparative Example 1 | Compound (A) | Liq/Al | 3.7 | 5.1 | 300 |
| Example 3 | Compound (1-38) | Liq/Mg + Ag | 3.7 | 5.5 | 400 |
| Example 4 | Compound (1-39) | Liq/Mg + Ag | 3.9 | 5.5 | 500 |
| Example 5 | Compound (1-40) | Liq/Mg + Ag | 3.4 | 5.9 | 350 |
| Comparative Example 2 | Compound (A) | Liq/Mg + Ag | 3.6 | 4.9 | 400 |
| Example 6 | Compound (1-35) | Liq/Mg + Ag | 3.6 | 5.6 | 300 |

TABLE 4-continued

| | Electron transport layer material | Cathode material | Driving voltage (V) | External quantum efficiency (%) | Device life (hour) |
|---|---|---|---|---|---|
| Example 7 | Compound (1-34) | Liq/Mg + Ag | 3.6 | 5.6 | 300 |
| Comparative Example 3 | Compound (B) | Liq/Mg + Ag | 3.8 | 4.3 | 220 |
| Example 8 | Compound (1-51) | Liq/Al | 3.8 | 5.7 | 450 |
| Comparative Example 4 | Compound (C) | Liq/Al | 3.9 | 5.8 | 380 |

* An electron transport layer was formed with a mixture of a compound listed in the Table and Liq.

The following Table 5 summarizes test results of the above-mentioned electroluminescent elements relating to Examples 9 to 11 and Comparative Examples 2 and 5.

TABLE 5

| | Electron transport layer material | Cathode Material | Driving voltage (V) | External quantum efficiency (%) | Device life (hour) |
|---|---|---|---|---|---|
| Example 9 | Compound (1-6) | Liq/Mg + Ag | 3.7 | 5.3 | 500 |
| Example 10 | Compound (1-164) | Liq/Mg + Ag | 3.7 | 5.6 | 400 |
| Comparative Example 2 | Compound (A) | Liq/Mg + Ag | 3.6 | 4.9 | 400 |
| Example 11 | Compound (1-262) | Liq/Mg + Ag | 3.6 | 5.5 | 350 |
| Comparative Example 5 | Compound (D) | Liq/Mg + Ag | 3.6 | 5.0 | 350 |

* An electron transport layer was formed with a mixture of a compound listed in the Table and Liq.

The following Table 6 summarizes test results of the above-mentioned electroluminescent elements relating to Example 12 and Comparative Example 3.

TABLE 6

| | Electron transport layer material | Cathode Material | Driving voltage (V) | External quantum efficiency (%) | Device life (hour) |
|---|---|---|---|---|---|
| Example 12 | Compound (1-68) | Liq/Mg + Ag | 4.6 | 4.2 | 350 |
| Comparative Example 3 | Compound (B) | Liq/Mg + Ag | 3.8 | 4.3 | 220 |

* An electron transport layer was formed with a mixture of a compound listed in the Table and Liq.

INDUSTRIAL APPLICABILITY

According to a preferable aspect of the present invention, particularly, an organic electroluminescent element which improves a life of a luminescent element, and is also excellent in balance between a driving voltage, as well as a display device equipped with the same and a lighting device equipped with the same can be provided.

REFERENCE SIGNS LIST

100 Organic electroluminescent element
101 Substrate
102 Anode
103 Hole injection layer
104 Hole transport layer
105 Luminescent layer
106 Electron transport layer
107 Electron injection layer
108 Cathode

The invention claimed is:
1. An anthracene derivative represented by the following formula (1):

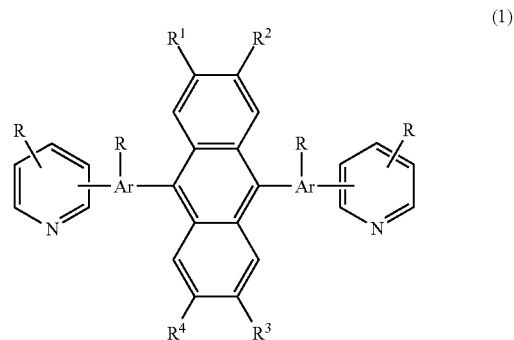

(1)

wherein
Ars are each independently divalent or trivalent benzene or naphthalene,
Rs are each independently hydrogen or an alkyl having a carbon number of 1 to 6, with which Ar or pyridine is substituted, and not all Rs are hydrogen simultaneously, and
$R^1$, $R^2$, $R^3$ and $R^4$ are each independently hydrogen, an alkyl having a carbon number of 1 to 6, a cycloalkyl having a carbon number of 3 to 6 or an aryl having a carbon number of 6 to 20.
2. The anthracene derivative according to claim 1, wherein
moieties consisting of Ar and pyridine are each independently a group represented by any of the following formula (Py-1) to formula (Py-12):

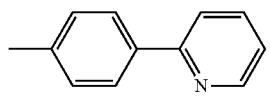

(Py-1)

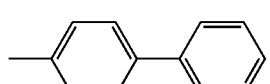

(Py-2)

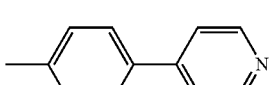

(Py-3)

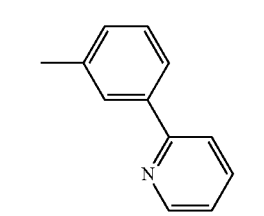

(Py-4)

-continued

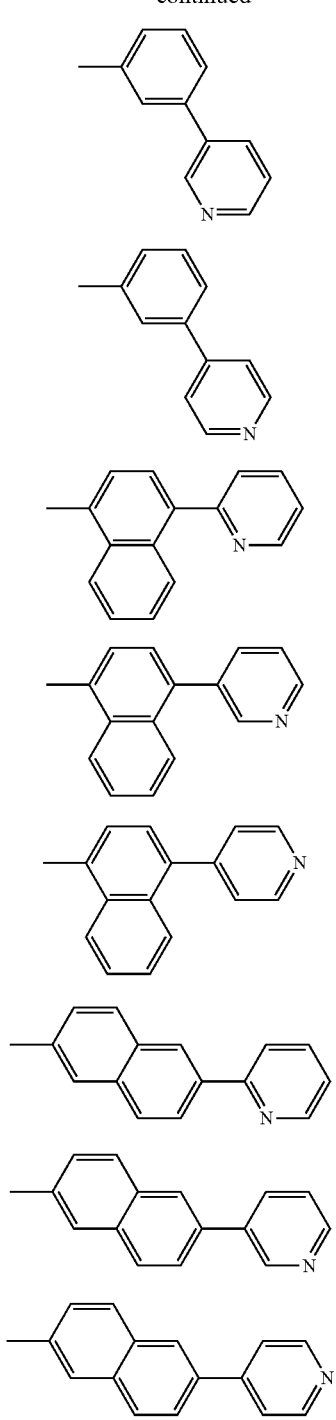

wherein
Rs are each independently hydrogen or an alkyl having a carbon number of 1 to 4, with which a group represented by any of the formula (Py-1) to formula (Py-12) is substituted, and not all Rs are hydrogen simultaneously, and
$R^1$ is hydrogen, an alkyl having a carbon number of 1 to 6 or an aryl having a carbon number of 6 to 20, and $R^2$, $R^3$ and $R^4$ are hydrogen.

3. The anthracene derivative according to claim 2, wherein
moieties consisting of Ar and pyridine are both a group represented by any of the formula (Py-1) to formula (Py-9),
two Rs binding to Ar are both hydrogen and two Rs binding to pyridine are both an alkyl having a carbon number of 1 to 4, or two Rs binding to Ar are both an alkyl having a carbon number of 1 to 4 and two Rs binding to pyridine are both hydrogen, and
$R^1$ is hydrogen, an alkyl having a carbon number of 1 to 4, phenyl, biphenylyl, terphenylyl or naphthyl, and $R^2$, $R^3$ and $R^4$ are hydrogen.

4. The anthracene derivative according to claim 2, wherein
moieties consisting of Ar and pyridine are both a group represented by any of the formula (Py-1) to formula (Py-9),
two Rs binding to Ar are both hydrogen, and one of two Rs binding to pyridine is an alkyl having a carbon number of 1 to 4 and the other is hydrogen, and
$R^1$ is hydrogen, an alkyl having a carbon number of 1 to 4, phenyl, biphenylyl, terphenylyl or naphthyl, and $R^2$, $R^3$ and $R^4$ are hydrogen.

5. The anthracene derivative according to claim 2, wherein
moieties consisting of Ar and pyridine are both a group represented by any of the formula (Py-1) to formula (Py-6),
two Rs binding to Ar are both hydrogen, and two Rs binding to pyridine are both an alkyl having a carbon number of 1 to 4, and
$R^1$ is hydrogen, phenyl, terphenylyl or naphthyl, and $R^2$, $R^3$ and $R^4$ are hydrogen.

6. The anthracene derivative according to claim 2, wherein
moieties consisting of Ar and pyridine are both a group represented by any of the formula (Py-1) to formula (Py-6),
two Rs binding to Ar are both an alkyl group having a carbon number of 1 to 4, and two Rs binding to pyridine are both hydrogen, and
$R^1$ is hydrogen or phenyl, and $R^2$, $R^3$ and $R^4$ are hydrogen.

7. The anthracene derivative according to claim 2, wherein
moieties consisting of Ar and pyridine are both a group represented by any of the formula (Py-1) to formula (Py-6),
two Rs binding to Ar are both hydrogen, and one of two Rs binding to pyridine is an alkyl having a carbon number of 1 to 4 and the other is hydrogen, and
$R^1$ is hydrogen or phenyl, and $R^2$, $R^3$ and $R^4$ are hydrogen.

8. The anthracene derivative according to claim 1, which is represented by the following formula (1-34), formula (1-35), formula (1-38), formula (1-39), formula (1-40), formula (1-41), formula (1-50) or formula (1-51)

(1-34)

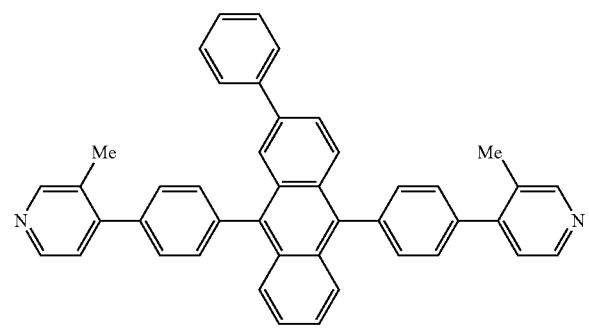

(1-35)
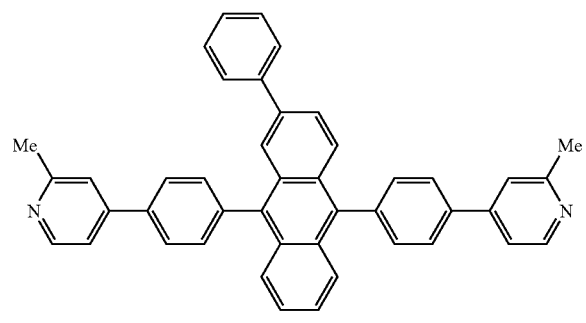
(1-41)
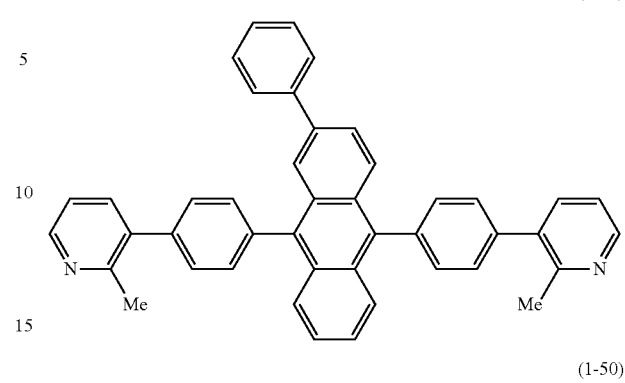
(1-38)
(1-50)
(1-39)
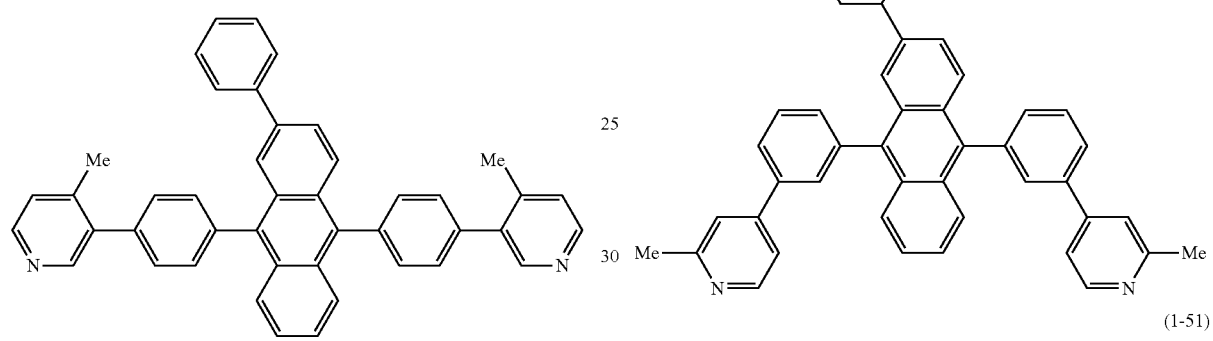
(1-51)
9. The anthracene derivative according to claim 1, which is represented by the following formula (1-6), formula (1-36), formula (1-44), formula (1-45), formula (1-151), formula (1-164), formula (1-236), formula (1-249) or formula (1-262)
(1-40)
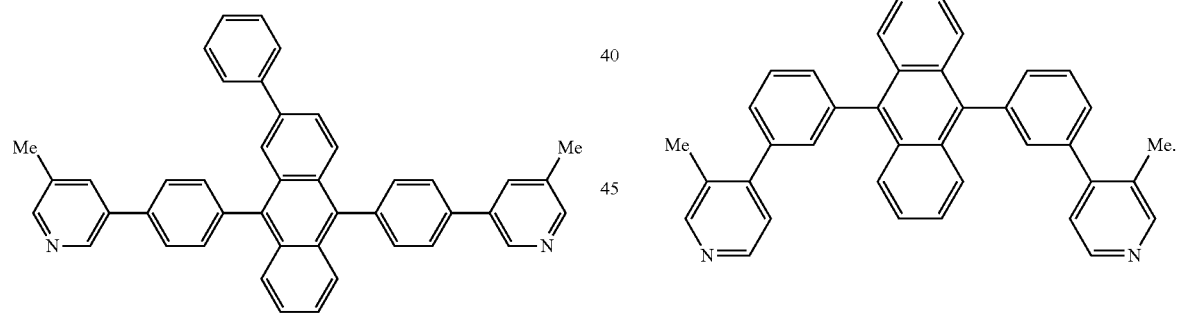
(1-6)
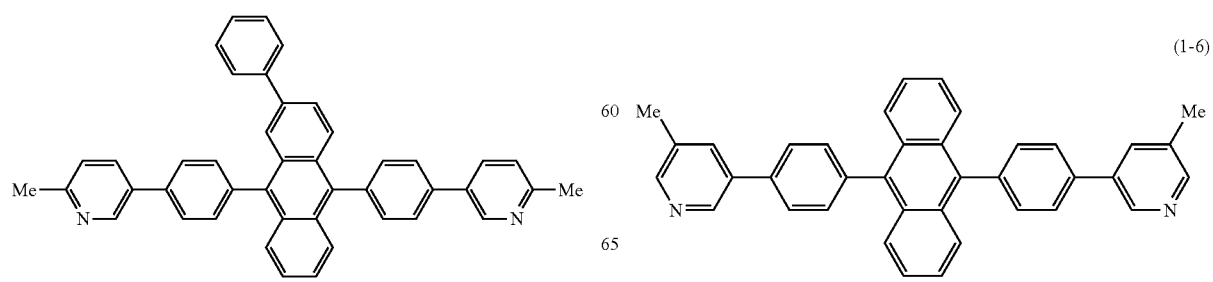

(1-36)
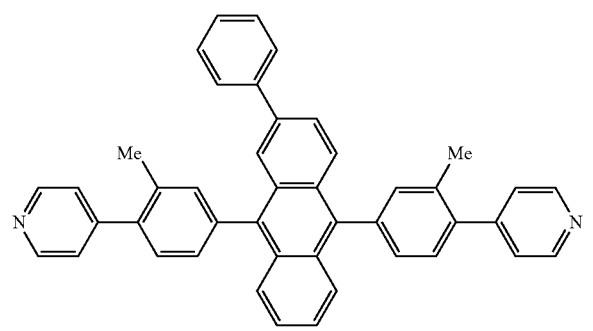
(1-44)
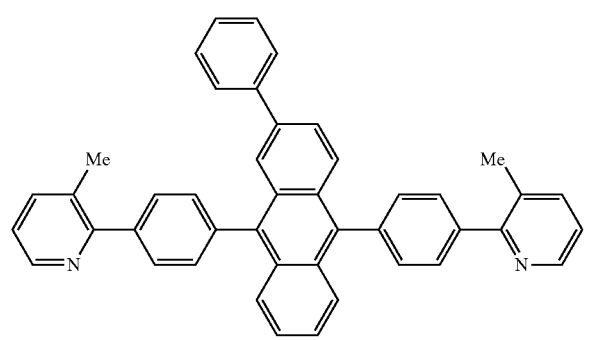
(1-45)
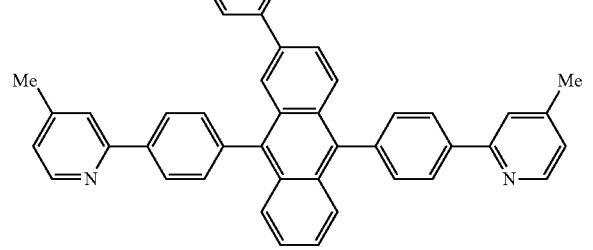
(1-151)
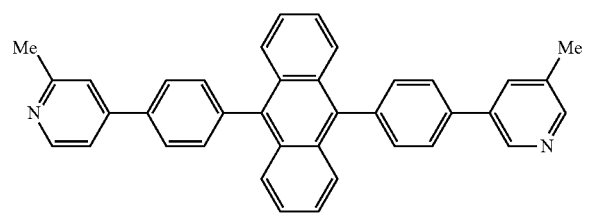
(1-164)
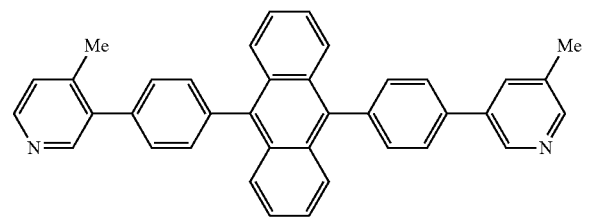
(1-236)
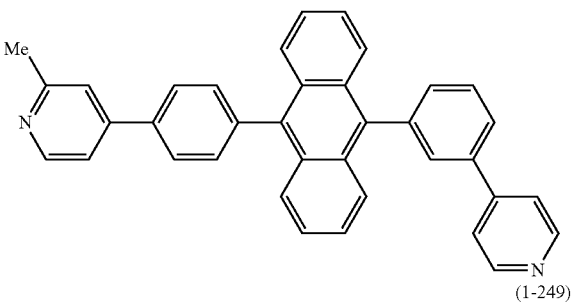
(1-249)
(1-262)
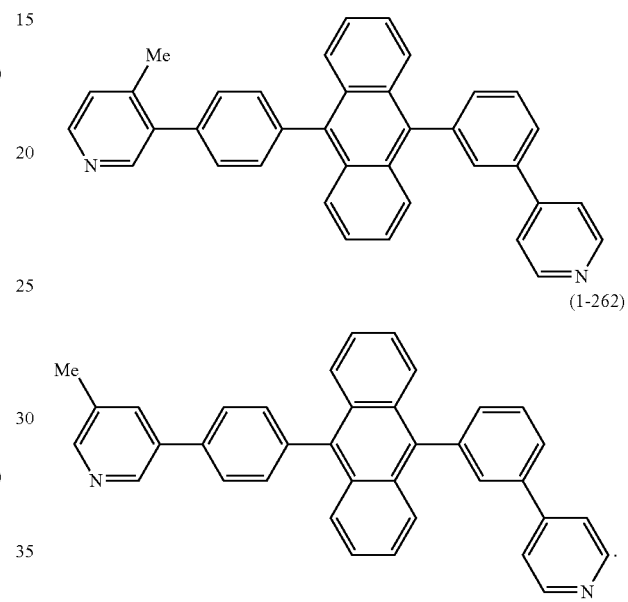
10. The anthracene derivative according to claim 1, which is represented by the following formula (1-46), formula (1-68), formula (1-71), formula (1-72) or formula (1-110)
(1-46)
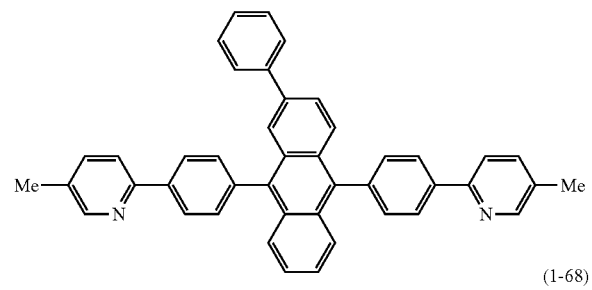
(1-68)
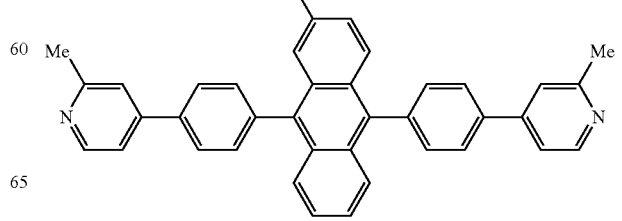

-continued (1-71)
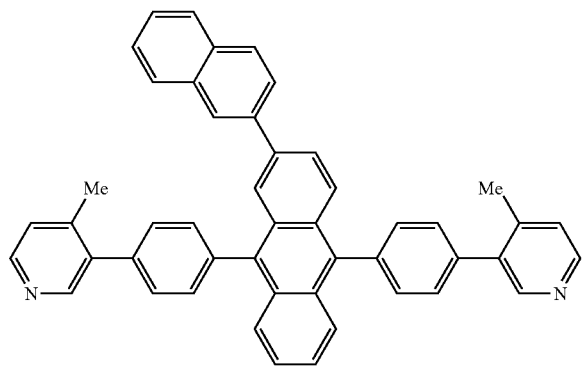

(1-72)
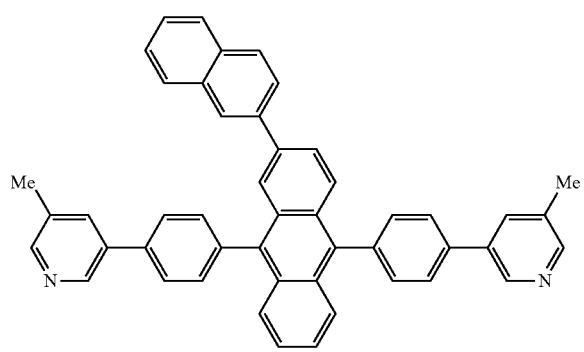

(1-110)
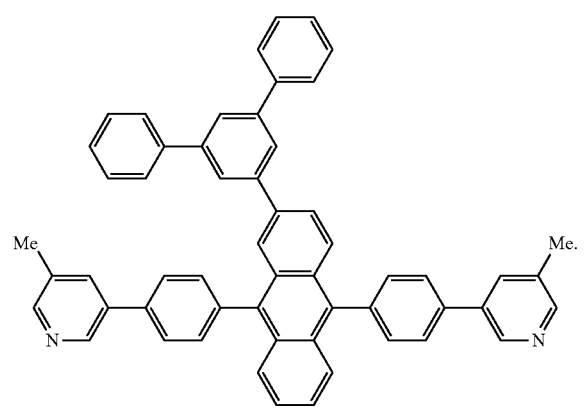

11. An electron transport material containing the anthracene derivative according to claim 1.

12. An organic electroluminescent element having a pair of electrodes consisting of an anode and a cathode, a luminescent layer arranged between the pair of electrodes, and an electron transport layer and/or an electron injection layer, which are arranged between the cathode and the luminescent layer, and contain the electron transport material according to claim 11.

13. The organic electroluminescent element according to claim 12, wherein at least one of the electron transport layer and the electron injection layer further contains at least one selected from the group consisting of a quinolinol metal complex, a pyridine derivative, a bipyridine derivative, a phenanthroline derivative, a borane derivative and a benzimidazole derivative.

14. The organic electroluminescent element according to claim 12, wherein at least one of the electron transport layer and the electron injection layer further contains at least one selected from the group consisting of an alkali metal, an alkaline earth metal, a rare earth metal, an oxide of an alkali metal, a halide of an alkali metal, an oxide of an alkaline earth metal, a halide of an alkaline earth metal, an oxide of a rare earth metal, a halide of a rare earth metal, an organic complex of an alkali metal, an organic complex of an alkaline earth metal and an organic complex of a rare earth metal.

15. A display device equipped with the organic electroluminescent element according to claim 12.

16. A lighting device equipped with the organic electroluminescent element according to claim 12.

* * * * *